United States Patent [19]

Kehrbach et al.

[11] Patent Number: 5,679,699
[45] Date of Patent: Oct. 21, 1997

[54] (PHENYLALKYLAMINOALKYLOXY)-HETEROARYL-COMPOUNDS, PROCESSES AND INTERMEDIATES FOR THEIR PRODUCTION AND PHARMACEUTICAL COMPOSITIONS CONTAINING THEM

[75] Inventors: Wolfgang Kehrbach; Michael Mlinaric, both of Hanover; Dieter Ziegler, Hemmingen; Reinhard Brueckner, Hanover; Willi Bielenberg, Alfeld/Leine, all of Germany

[73] Assignee: Kali-Chemie Pharma GmbH, Hanover, Germany

[21] Appl. No.: 576,699

[22] Filed: Dec. 21, 1995

Related U.S. Application Data

[60] Division of Ser. No. 476,118, Jun. 7, 1995, Pat. No. 5,547,967, which is a continuation-in-part of Ser. No. 352,353, Dec. 8, 1994, abandoned.

[30] Foreign Application Priority Data

Dec. 8, 1993 [DE] Germany ............... 43 41 749.3
Apr. 10, 1995 [DE] Germany ............... 195 13 503.2

[51] Int. Cl.$^6$ ............... A61K 31/415; C07D 231/20; C07D 403/12
[52] U.S. Cl. ............... 514/403; 514/407; 548/370.1; 548/364.1
[58] Field of Search ............... 548/370.1, 364.1; 514/407, 403

[56] References Cited

U.S. PATENT DOCUMENTS

| | | | |
|---|---|---|---|
| 3,920,691 | 11/1975 | Wasson et al. | 260/310 R |
| 4,330,544 | 5/1982 | Jarreau et al. | 424/248.56 |
| 4,410,525 | 10/1983 | Jarreau et al. | 424/248.57 |
| 4,455,428 | 6/1984 | Diehr et al. | 548/187 |
| 4,528,379 | 7/1985 | Cölln et al. | 546/209 |
| 4,695,566 | 9/1987 | Heinneman et al. | 514/234 |
| 5,090,991 | 2/1992 | Föster et al. | 71/90 |
| 5,101,034 | 3/1992 | Schmidt et al. | 548/136 |
| 5,366,987 | 11/1994 | Lee et al. | 514/378 |

FOREIGN PATENT DOCUMENTS

| | | |
|---|---|---|
| 007019 | 6/1979 | European Pat. Off. . |
| 0007019 | 1/1980 | European Pat. Off. . |
| 9310099 | 5/1993 | WIPO . |

*Primary Examiner*—Johann Richter
*Assistant Examiner*—Laura R. Cross
*Attorney, Agent, or Firm*—Evenson, McKeown, Edwards & Lenahan P.L.L.C.

[57] ABSTRACT

3-(Phenylalkylaminoalkyloxy)-heteroaryl compounds having heart rate lowering and/or anti-ischemic effects, methods for their preparation and pharmaceutical compositions containing them are described. The compounds correspond to the general formula I $$R^2\text{-phenyl}(R^3)-(CH_2)_n-A-O-CHR^4-N(R^5)-N-\text{phenyl}(R^6,R^7) \quad I$$

or to the general formula XXXI $$\text{A=B(R}^4)-C(=)-O-Q-N(R^1)-(CH_2)_n-\text{phenyl}(R^2,R^3) \quad XXXI$$

in which the substituents have the meanings given in the specification.

6 Claims, No Drawings

(PHENYLALKYLAMINOALKYLOXY)-HETEROARYL-COMPOUNDS, PROCESSES AND INTERMEDIATES FOR THEIR PRODUCTION AND PHARMACEUTICAL COMPOSITIONS CONTAINING THEM

CROSS REFERENCE TO RELATED APPLICATION

This application is a division of co-pending application Ser. No. 08/476,118, filed Jun. 7, 1995, now U.S. Pat. No. 5,547,967, which in turn is and a continuation-in-part of our application Ser. No. 08/352,353, filed Dec. 8, 1994 now abandoned.

BACKGROUND OF THE INVENTION

The present invention relates to novel phenylalkylaminoalkyl compounds which carry a heteroaryl substituent on the alkyl radical, to salts thereof, to pharmaceutical compositions containing them and to processes and intermediates for their production.

European Patent Application No. EP 007,019 discloses 3-hydroxycarbonylmethoxy-5-phenylpyrazole compounds and esters and amides thereof having the property of lowering blood lipids levels. European Patent Application No. EP 170,861 discloses 3-(aminoalkylaminocarbonylmethoxy)-5-phenylpyrazole compounds having antiarrhythmic effects, in particular the property of raising the stimulus threshold for initiation of cardiac arrhythmias.

SUMMARY OF THE INVENTION

It is the object of the present invention to provide new aminoalkyloxyheteroaryl compounds having valuable pharmacological properties.

A further object of the invention is to develop novel active pharmaceutical substances which can be used to lower the heart rate.

Another object of the invention is to provide active pharmaceutical substances which are useful to treat ischaemic heart conditions.

It has now been found that the novel 5-phenylpyrazole compounds according to the invention, which carry a phenylalkylaminoalkyloxy radical in the 3-position, have valuable cardioactive pharmacological properties and exhibit pronounced heart rate lowering effects together with a favorable activity profile. Because of their activity profile, the compounds of the invention are useful as active substances which are effective in lowering heart rate for treating ischaemic conditions.

It has also now been found that the novel aminoalkyloxyheteroaryl compounds substituted on the amino group by a phenylalkyl residue possess valuable pharmacological properties that affect the heart and exhibit an activity profile that is suitable for treatment of ischemic cardiac conditions.

The invention therefore relates to compounds corresponding to the general formula I

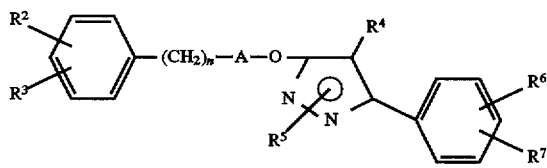

in which n is an integer from 1 to 5,

A represents a group of the formula a

in which $R^1$ represents hydrogen or a lower alkyl group and Q represents a $(CH_2)_m$ group in which m is 2 to 8 and which may optionally be substituted in the α position to the oxygen atom by 1 or 2 lower alkyl groups, or Q represents a 2-hydroxypropylene chain, or A represents a group of the formula b

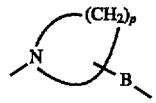

in which p is 4 to 6 and B represents a $(CH_2)_r$ group in which r is 1 to 3 and which may optionally be substituted in the α position to the oxygen atom by 1 or 2 lower alkyl groups;

$R^2$ represents hydrogen, halogen, lower alkyl, lower alkoxy, hydroxyl, trifluoromethyl or nitro, or if A contains no OH group and $R^3$, $R^6$ and $R^7$ are not hydroxyl, $R^2$ may alternatively represent lower alkanoyloxy, and $R^3$ represents hydrogen, halogen, lower alkyl, lower alkoxy or hydroxyl, or if A contains no OH group and $R^2$, $R^6$ and $R^7$ are not hydroxyl, $R^3$ may alternatively represent lower alkanoyloxy, or $R^2$ and $R^3$ are attached to two adjacent carbon atoms and together represent an alkylenedioxy group containing 1 or 2 carbon atoms;

$R^4$ represents hydrogen or lower alkyl, $R^5$ is disposed in the 1 or 2 position and represents hydrogen, lower alkyl or a phenyl-lower alkyl group, $R^6$ represents hydrogen, lower alkyl, lower alkoxy, hydroxyl, halogen, trifluoromethyl or nitro, or if A contains no OH group and $R^2$, $R^3$ and $R^7$ are not hydroxyl, $R^6$ alternatively may represent lower alkanoyloxy, and $R^7$ denotes hydrogen, lower alkyl, lower alkoxy, hydroxyl or halogen, or if A contains no OH group and $R^2$, $R^3$ and $R^6$ are not hydroxyl, $R^7$ may alternatively represent lower alkanoyloxy, or $R^6$ and $R^7$ are attached to two adjacent carbon atoms and together form an alkylenedioxy group containing 1 or 2 carbon atoms, and their acid addition salts.

If in the compounds of formula I, the substituents $R^2$, $R^3$, $R^6$ and $R^7$ of the phenyl rings represent or contain lower alkyl groups, these groups may be straight chain or branched and may contain 1 to 4, preferably 1 or 2, carbon atoms and represent in particular methyl, methoxy or acetoxy. If the substituents represent halogen, they may suitably be fluorine, chlorine or bromine, preferably fluorine or chlorine.

If A represents a group of formula a, $R^1$ is preferably lower alkyl, especially methyl, or hydrogen, and Q represents a preferably unsubstituted alkylene chain $(CH_2)_m$ in which m is 2 to 8, preferably 2 to 6, in particular 2, 3 or 4. If A represents a group of formula b, it preferably will contain a 6-member ring, i.e. p is preferably 5, and B preferably represents an unsubstituted alkylene chain containing 1 to 3 carbon atoms, in particular the methylene group.

The substituents $R^2$ and $R^3$ preferably represent hydrogen, hydroxy or lower alkoxy groups, especially methoxy. The substituents $R^6$ and $R^7$ preferably represent hydrogen, hydroxy or lower alkoxy, especially methoxy, or $R^6$ also may optionally be nitro.

$R^4$ preferably represents hydrogen. If $R^4$ represents lower alkyl, it is preferably methyl. If $R^5$ is a lower alkyl group or phenyl-lower alkyl group, it is preferably disposed on the nitrogen atom of the pyrazole ring which is adjacent to the oxygen atom. $R^5$ preferably represents hydrogen or alternatively a phenyl-lower alkyl group. If $R^5$ represents lower alkyl, it preferably denotes methyl or ethyl. If $R^5$ represents a phenyl-lower alkyl group, the alkylene chain thereof may contain 1 to 3 carbon atoms, and the group preferably represents benzyl.

In accordance with the invention, the compounds of formula I and their acid addition salts are obtained in a known manner in that a) to prepare a compound corresponding to the formula Ia

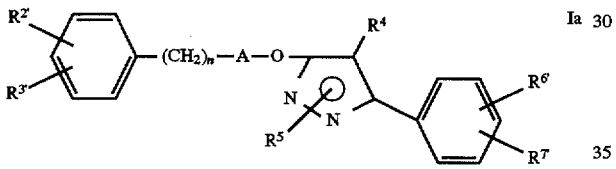

in which $R^4$, $R^5$, A and n have the above meanings, and $R^{2'}$, $R^{3'}$, $R^{6'}$ and $R^{7'}$ have the meanings given above for $R^2$, $R^3$, $R^6$ and $R^7$ with the exception of lower alkanoyloxy, a compound corresponding to the formula II

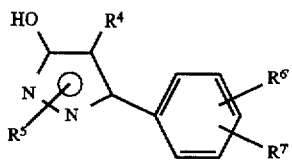

in which $R^4$, $R^5$, $R^{6'}$ and $R^{7'}$ have the above meanings, but in which any free hydroxyl groups are provided with a hydroxyl-protecting group, is reacted with a compound corresponding to the formula III

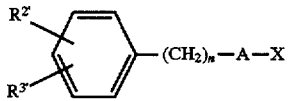

in which $R^{2'}$, $R^{3'}$, n and A have the above meanings, but in which any free hydroxyl groups are provided with a hydroxyl-protecting group, and X represents a leaving group which can be eliminated, and subsequently any hydroxyl-protecting groups are removed, or b) to prepare a compound corresponding to the formula Ib

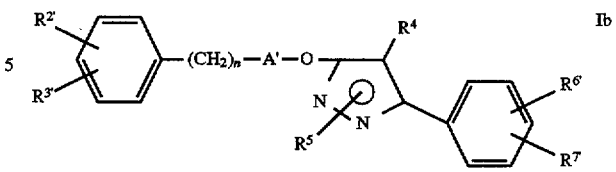

in which $R^{2'}$, $R^{3'}$, $R^4$, $R^5$, $R^{6'}$, $R^{7'}$ and n have the above meanings and A' has the meaning given above for A with the exception of a radical containing an OH group, a compound corresponding to formula II is reacted with triphenylphosphine in the presence of an azodicarboxylic ester of the formula XVIII $$R^{10}OOC-N=N-COOR^{11} \quad \text{XVIII}$$

in which $R^{10}$ and $R^{11}$ each denote lower alkyl, and the reaction product is reacted with a compound of the formula IV

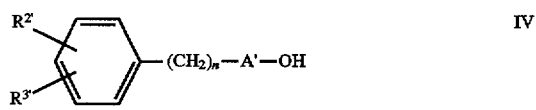

in which $R^{2'}$, $R^{3'}$, n and A' have the above meanings, except that any free NH group in the radical A' is provided with an amino-protecting group and any free hydroxyl groups are provided with hydroxyl-protecting groups, and subsequently any amino- or hydroxyl-protecting groups are removed, or c) to prepare a compound corresponding to the formula Ic

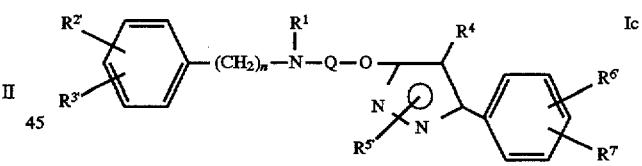

in which $R^1$, $R^{2'}$, $R^{3'}$, $R^4$, $R^{6'}$, $R^{7'}$, Q and n have the above meanings and $R^{5'}$ has the meaning given above for $R^5$, except that if the chain length m of the radical Q is 3, $R^{5'}$ represents a phenyl-lower alkyl group or lower alkyl group which is arranged on the nitrogen atom of the pyrazole ring which is adjacent to the oxygen atom, a compound corresponding to the formula V

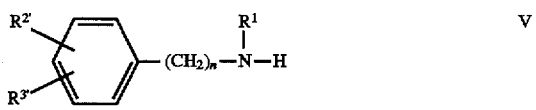

in which $R^1$, $R^{2'}$, $R^{3'}$ and n have the above meanings, but in which any free hydroxyl groups are provided with a hydroxyl-protecting group, is reacted with a compound corresponding to the formula VI

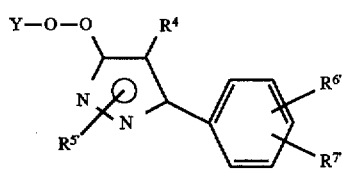

in which $R^4$, $R^{5'}$, $R^{6'}$, $R^{7'}$ and Q have the above meanings, but in which any free hydroxyl groups are each provided with a hydroxyl-protecting group, and Y represents a leaving group which can be eliminated by aminolysis, and subsequently any hydroxyl-protecting groups are removed, or d) to prepare a compound corresponding to the formula Ia, a compound corresponding to the formula VII

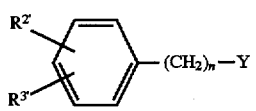

in which $R^{2'}$, $R^{3'}$, n and Y have the above meanings, but in which any free hydroxyl groups are provided with a hydroxyl-protecting group, is reacted with a compound corresponding to the formula VIII

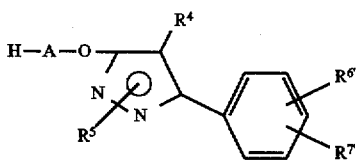

in which $R^4$, $R^5$, $R^{6'}$, $R^{7'}$ and A have the above meanings, but in which any free hydroxyl groups are provided with a hydroxyl-protecting group, and subsequently any hydroxyl-protecting groups are removed, or e) to prepare a compound corresponding to the formula Id

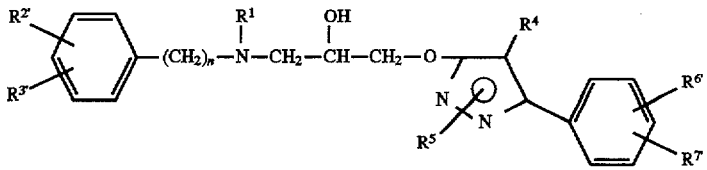

in which $R^1$, $R^{2'}$, $R^{3'}$, $R^4$, $R^5$, $R^{6'}$, $R^{7'}$ and n have the above meanings, a compound corresponding to the formula IX

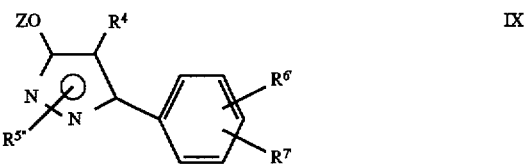

in which $R^4$, $R^{6'}$ and $R^{7'}$ have the above meanings, but in which any free hydroxyl groups are provided with a hydroxyl-protecting group, Z denotes hydrogen or the 2,3-epoxypropyl radical and $R^{5''}$ denotes a phenyl-lower alkyl group or lower alkyl group which is arranged on the nitrogen atom of the pyrazole ring which is adjacent the oxygen atom, or if Z is hydrogen, $R^{5''}$ has the meaning given above for $R^5$, is reacted with a compound corresponding to the formula X

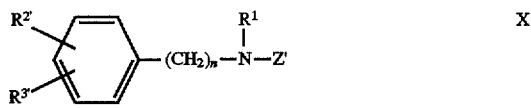

in which $R^1$, $R^{2'}$, $R^{3'}$ and n have the above meanings, but in which any free hydroxyl groups are provided with a hydroxyl-protecting group, and Z' represents the 2,3-epoxypropyl radical if Z denotes hydrogen, or Z' is hydrogen if Z denotes the 2,3-epoxypropyl radical, and subsequently any hydroxyl-protecting groups are removed, or f) to prepare a compound corresponding to the formula Ie

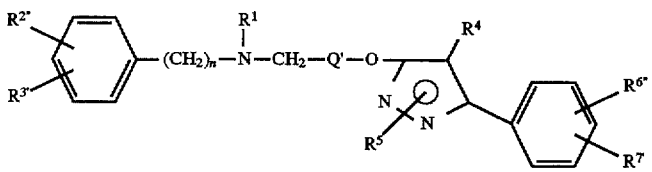

in which $R^1$, $R^{3'}$, $R^4$, $R^5$, $R^{7'}$ and n have the above meanings, $R^{2'}$ and $R^{6'}$ have the meanings given for $R^2$ and $R^6$, respectively, with the exception of nitro and lower alkanoyloxy, and Q' represents a $(CH_2)_{m'}$ group in which m' is 1 to 7 and which is optionally substituted in the α position to the oxygen atom by 1 or 2 lower alkyl groups, a compound corresponding to the formula XI

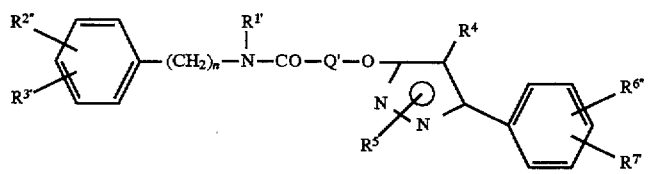

in which $R^{2''}$, $R^{3'}$, $R^4$, $R^5$, $R^{6''}$, $R^{7'}$, n and Q' have the above meanings, but in which any free hydroxyl groups are provided with a hydroxyl-protecting group, and $R^{1'}$ represents lower alkyl or an amino-protecting group, is reduced and subsequently any amino- and/or hydroxyl-protecting groups are removed, or g) to prepare a compound corresponding to the formula If

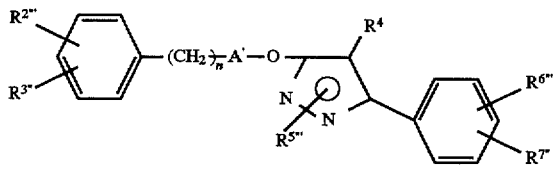

in which $R^4$, n and A' have the above meanings, $R^{5'''}$ has the meaning given for $R^5$ except that if the radical A' contains an NH group, $R^{5'''}$ is not benzyl, and in which $R^{2'''}$, $R^{3'''}$, $R^{6'''}$ and $R^{7''}$ have the meanings given for $R^2$, $R^3$, $R^6$ and $R^7$ with the exception of hydroxyl, but where at least one of the substituents $R^{2'''}$, $R^{3'''}$, $R^{6'''}$ and $R^{7''}$ represents lower alkanoyloxy, in a compound corresponding to the formula XII

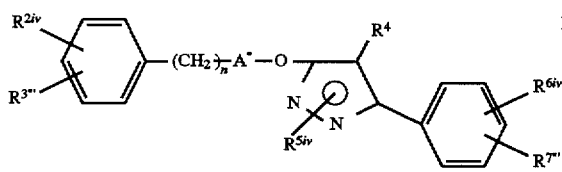

in which n and $R^4$ have the above meanings, $R^{2IV}$, $R^{3''''}$, $R^{6IV}$ and $R^{7'''}$ have the meanings given above for $R^2$, $R^3$, $R^6$ and $R^7$ with the exception of lower alkanoyloxy, but in which at least one of the substituents $R^{2IV}$, $R^{3''''}$, $R^{6IV}$ and $R^{7'''}$ is hydroxy, $R^{5IV}$ represents lower alkyl or a phenyl-lower alkyl group, and A" has the meaning given above for A', but in which any NH group present in the radical A" is protected by a benzyl protective group, the free hydroxyl groups $R^{2IV}$, $R^{3''''}$, $R^{6'''}$ and/or $R^{7'''}$ are acylated, and subsequently any benzyl protective group is removed, and if desired, in resulting compounds of formula I in which $R^2$, $R^3$, $R^6$ and/or $R^7$ represents methoxy, the methyl group is split off to leave a hydroxy group, and/or, if desired, in resulting compounds of formula I in which $R^5$ represents benzyl, the benzyl group is eliminated therefrom, and, if desired, free compounds of formula I are converted to their acid addition salts or the acid addition salts are converted to the free compounds of the formula I.

The reaction of compounds of formula II with compounds of formula III in accordance with process variant a) can take place in a known manner under the usual conditions for the formation of pyrazole ether compounds by alkylation of pyrazolols. Suitable leaving groups X in the compounds of the formula III are preferably halogens such as chlorine, bromine or iodine or else organic sulfonic acid radicals, for example radicals of lower alkanesulfonic acids such as methanesulfonic acid or of aromatic sulfonic acids such as benzenesulfonic acid or benzenesulfonic acids substituted by lower alkyl or halogen, for example toluenesulfonic acids or bromosulfonic acids. In general, approximately equivalent quantities of compounds of formulas II and III are used. If $R^5$ denotes a lower alkyl or phenyl-lower alkyl group, an excess of compound of formula III may also be used, but if $R^5$ denotes hydrogen, it is advantageous in order to avoid secondary reactions to use an excess of the compound of formula II or to protect the free NH function of the pyrazole ring with an amino-protecting group which can subsequently be removed. The reaction is advantageously carried out under basic conditions in an organic solvent which is inert under the reaction conditions. Examples of suitable inert organic solvents include dimethylformamide, tetramethylurea, acetone or alternatively, depending on the nature of the base added as an acid-binding agent, ethers, especially cyclic ethers such as tetrahydrofuran, lower alcohols, or aromatic hydrocarbons such as benzene or toluene, or mixtures of the foregoing solvents. The reaction is advantageously carried out in the presence of an at least equivalent quantity of an acid-binding base. Suitable bases include, e.g. inorganic or organic alkali metal compounds. Examples of suitable bases include alkali metal carbonates or else alkali metal hydroxides, alkali metal hydrides such as sodium hydride, or lower alkali metal alcoholates such as, for example, potassium tert-butylate or sodium methylate, or alkali metal amides such as, for example, lithium amide or lithium diisopropylamide. If desired, catalytic quantities of an iodide salt, for example an alkali metal iodide or ammonium iodide, such as potassium iodide or tert-butylammonium iodide, can be added in order to accelerate the reaction. The reaction can be carried out at temperatures between room temperature and the boiling temperature of the reaction mixture. The reaction is advantageously carried out using, for example, an inorganic base such as potassium carbonate or sodium hydride in an inert solvent such as dimethylformamide, preferably at a temperature between 80° and 120° C. If desired the reaction can also be carried out in a two-phase system in the presence of a phase transfer catalyst, for example benzyl tri-lower alkyl ammonium chloride. Any hydroxyl group in the group A can be protected during the reaction by a hydroxyl-protecting group which can easily be subsequently removed.

The preparation of compounds of formula I b in accordance with process variant b) can take place under the usual conditions for Mitsunobu reactions. For example, the reaction can be carried out in an inert, anhydrous, aprotic organic solvent, in particular a cyclic ether such as tetrahydrofuran or dioxane and/or an aromatic hydrocarbon such as benzene or toluene.

The reactions of compounds of formula V with compounds of formula VI and of compounds of formula VII with compounds of formula VIII in accordance with the process variants c) and d) can be performed by the usual methods for alkylating amines. Suitable radicals Y, which can be eliminated by aminolysis from the compounds of formulas VI and VII, include halogens such as chlorine, bromine or iodine, preferably bromine or chlorine, or alternatively an organic sulfonic acid radical, for example the radical of a lower alkanesulfonic acid such as, for example, methanesulfonic acid or of an aromatic sulfonic acid such as benzenesulfonic acid or benzenesulfonic acid which is substituted by lower alkyl or by halogen, for example toluenesulfonic acids or bromobenzenesulfonic acids. The reaction can be carried out under basic conditions in an organic solvent which is inert under the reaction conditions. For example, the solvents, bases and reaction conditions given above for the process variant a) may be used. Any hydroxyl group in the chain Q or in the group A is advantageously protected during the reaction, as described for process variant a), by a hydroxyl-protecting group which can easily be removed again. Advantageously, the reaction is performed at a temperature between room temperature and the boiling temperature of the reaction mixture and, depending on the reaction conditions, may require from about ¼ hour to 6 hours. The reaction is advantageously carried out, for example, in an inert solvent such as dimethylformamide in the presence of an inorganic base such as potassium carbonate at a temperature of between 80° and 120° C. The process variants c) and d) are particularly suitable for preparing compounds of formula I in which $R^5$ represents a phenyl-lower alkyl or lower alkyl group which is attached to the nitrogen atom adjacent the oxygen atom in the pyrazole ring.

The reaction of compounds of formula IX with compounds of formula X in accordance with process variant e) can be carried out in a known manner by conventional methods for reacting alcohols or amines with epoxides. Thus a compound of formula IX is reacted with a compound of formula X under basic conditions in an organic solvent which is inert under the reaction conditions. The solvents and bases listed above for process variants a), c) and d) can be used. The reaction temperature may lie within the range from 60° to 120° C. Depending on the reaction conditions, the duration of the reaction may be between 4 and 12 hours. The reaction is advantageously carried out, for example, in an inert solvent such as dimethylformamide in the presence of an inorganic base such as potassium carbonate at temperatures of around 100° C.

The reduction of compounds of formula XI in accordance with process variant f) can be carried out by conventional methods for reducing amides. Suitable reducing agents include complex metal hydrides capable of amide reduction, especially aluminum hydrides such as lithium aluminum hydride. The reaction should be carried out in a sufficiently anhydrous solvent which is inert under the reaction conditions. Examples of suitable solvents include cyclic ethers such as tetrahydrofuran or dioxane or open-chain ethers such as ethylene glycol dimethyl ether or diethylene glycol dimethyl ether, optionally in admixture with aromatic hydrocarbons such as benzene or toluene. Depending on the nature of the reducing agent used, the reaction can be carried out at elevated temperature, for example at the boiling point of the reaction mixture. For example, it is advantageous to carry out the reaction with lithium aluminum hydride at the boiling temperature of the reaction mixture. The reaction time may be between 1 and 10 hours.

The acylation of compounds of formula XII in accordance with process variant g) may be carried out by conventional methods for forming phenol esters by reacting a compound of formula XII with a reactive derivative of a corresponding lower carboxylic acid, for example a lower carboxylic acid halide or anhydride.

If the group A" in a compound of formula XII contains a benzyl-protected NH function, this benzyl protective group can subsequently be removed again by known methods for cleaving benzylamines. In conjunction therewith, any benzyl group $R^5$ will likewise be eliminated at the same time. A reductive elimination, for example, is advantageous. This can be carried out using formic acid as a reducing agent in the presence of a palladium catalyst or by hydrogenolysis using hydrogen as reducing agent in the presence of a palladium catalyst.

If the radicals $R^{2'}$, $R^{3'}$, $R^{6'}$ and $R^7$ represent free hydroxyl substituents, they must be protected in a known manner during the above-described reactions in accordance with process variants a)–f) and during the preparation of the starting materials, by protecting groups which can easily be removed again. Suitable, removable protective groups for hydroxyl groups are known from E. McOmie, *Protective Groups in Organic Chemistry*, Plenum Press, 1971. For example, a hydroxyl group can suitably be protected by esters, for example acetates, readily eliminatable carbonates such as benzyl carbonates and readily eliminatable ethers such as tetrahydropyranyl ethers or benzyl ethers. In each case protective groups must be chosen which are not attacked during the reactions carried out and which can subsequently be removed under conditions under which the products formed are not attacked. Preferably, ether protective groups such as benzyl ethers are used. Hence, in the reaction of starting compounds of formula II with starting compounds of formula III in which at least one of the radicals $R^{2'}$, $R^{3'}$, $R^{6'}$ and $R^7$ represents a hydroxyl group which is protected by benzyl ether formation, the compounds initially obtained correspond to the formula XXVIII

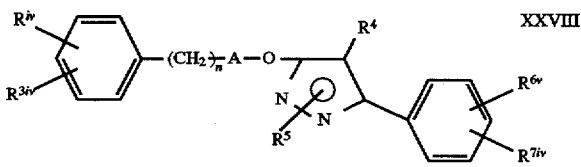

in which $R^4$, $R^5$, A and n have the above meanings, and $R^{2V}$, $R^{3IV}$, $R^{6V}$ and $R^{7IV}$ have the meanings given for $R^{2'}$, $R^{3'}$, $R^{6'}$ and $R^{7'}$ or denote benzyloxy, but where at least one of $R^{2V}$, $R^{3IV}$, $R^{6V}$ and $R^{7IV}$ is benzyloxy. The compounds of formula XXVIII are novel and represent valuable intermediates for the preparation of pharmacologically active compounds, for example compounds of formula I, and also themselves possess cardioactive pharmacological properties similar to the properties of the compounds of formula I.

If $R^5$ represents hydrogen and/or if A contains a free NH group, the free NH groups may be protected in a known manner, if desired, by protective groups which can easily be removed again. This may be advantageous, for example during the reaction of a compounds of formula V with a compound of formula VI, if the chain length m of the radical Q is 3. Suitable protective groups for NH groups, which can easily be eliminated again after the reaction, are known for example from E. McOmie, *Protective Groups in Organic Chemistry*, Plenum Press, 1971. For example, to protect an NH function in the pyrazole ring, the benzyl and the trityl group or the tetrahydropyranyl group are suitable. In each case a protective group must be selected which is not attacked during the reactions carried out and which can subsequently be removed under conditions under which the products formed are not attacked. Preferably, the benzyl group is used as the protective group.

In compounds of formula I in which the substituents $R^2$, $R^3$, $R^6$ and/or $R^7$ denote methoxy, it is possible, if desired, to subsequently convert the methoxy group to a hydroxy group. Methoxy groups can be cleaved to form hydroxyl groups in a known manner using methods suitable for cleaving methoxyaryl ethers. For example, ether cleavage can be effected by treatment with hydrogen iodide or hydrogen bromide in a solvent which is inert under the reaction conditions, for example acetic anhydride or acetic acid, or with iodotrimethylsilane or boron tribromide in a halogenated hydrocarbon such as dichloromethane. Any lower alkanoyloxy groups are similarly cleaved under the conditions of the ether cleavage.

From compounds of formula I, in which $R^5$ represents a benzyl group, it is possible to subsequently eliminate this benzyl group by known methods for benzylamine cleavage in order to obtain corresponding compounds of formula I in which $R^5$ is hydrogen. The benzyl group can be eliminated by reductive or hydrogenolytic cleavage, for example under conditions given in process variant g) for removing a benzyl protective group.

The compounds of formula I can be isolated from the reaction mixture and purified in a known manner. Acid addition salts can be converted in a conventional manner to the corresponding free bases, which can be converted in a known manner, if desired, into pharmacologically acceptable acid addition salts.

Examples of suitable pharmacologically acceptable acid addition salts of the compounds of formula I include their salts with inorganic acids, for example hydrohalic acids, especially hydrochloric acid, sulfuric acid or phosphoric acids, or with organic acids, for example lower aliphatic monocarboxylic or dicarboxylic acids such as maleic acid, fumaric acid, lactic acid, tartaric acid or acetic acid, or sulfonic acids, for example lower alkanesulfonic acids, such as methanesulfonic acid, or benzenesulfonic acids which are optionally substituted in the benzene ring by halogen or by lower alkyl, such as p-toluenesulfonic acid, or cyclohexylaminesulfonic acid.

If A in the compounds of formula I represents the group b) or a group a) in which Q denotes a hydroxypropylene chain, the compounds contain an asymmetric center and may exist in two optically active forms or as a racemate. The present invention includes both the racemic mixtures and the optical isomers of the compounds of formula I. The optically active compounds can be obtained from the racemic mixtures in a known manner by conventional separation methods, for example by chromatographic separation on chiral separating materials or by fractional crystallization of suitable salts with optically active acids. Enantiomerically pure compounds can also be prepared by synthesis from corresponding enantiomerically pure starting compounds. For example, sterically pure isomers of the starting compounds of formulas III, IV and VIII can be converted into sterically pure compounds of formula I by the above-described process variants a), b) and d).

The starting compounds of formula II are known or can be prepared by known methods. It is known that the compounds of formula II exist in more than one tautomeric form and that, in addition to the enol form of the 5-phenylpyrazol-3-ols represented by the formula II, the corresponding keto form of the 5-phenylpyrazol-3-ones also exists. In general, the compounds exist as mixtures of the different tautomeric forms whose composition may vary depending on the nature of the substituents. Both forms and their mixtures can be used for preparing compounds of formula I according to the invention. Thus, as used in the present application, the phrase "compounds of formula II" is intended to embrace all of the tautomeric forms of such compounds.

Compounds of formula II can be obtained by known methods for preparing 5-phenylpyrazolin-3-ones, for example by cyclizing condensation of an optionally substituted hydrazine of the formula XIX $$NH_2-NHR^5 \qquad XIX$$

in which $R^5$ has the above meaning, with a benzoylacetic ester of the formula XX

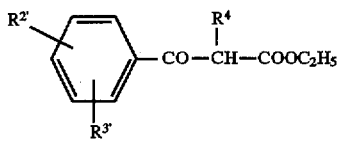

in which $R^{2'}$, $R^{3'}$ and $R^4$ have the above meanings, or with phenylpropionic esters corresponding to the formula XXI

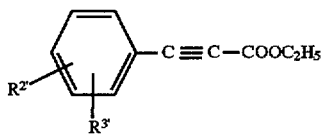

in which $R^{2'}$ and $R^{3'}$ have the above meanings. The reaction is carried out in an organic solvent which is inert under the reaction conditions. If $R^5$ denotes lower alkyl or a phenyl-lower alkyl group, the reaction produces mixtures of isomeric compounds in which $R^5$ is in the 1 or 2 position. The ratio of 1-substituted to 2-substituted compounds may vary depending on the nature of the starting materials and the solvent used. Isomer mixtures of 1-substituted and 2-substituted compounds may be separated in a known manner by fractional crystallization or by chromatography.

In compounds of the formula II in which $R^5$ denotes hydrogen, it is possible, if desired, to subsequently introduce a benzyl group $R^5$ in a known manner by reacting the compounds with a benzyl halide, preferably benzyl bromide, in an organic solvent which is inert under the reaction conditions, for example an aromatic hydrocarbon such as toluene, in the presence of a base, for example pyridine or preferably collidine. In the course of the benzylation, isomer mixtures of compounds benzylated in the 1-position and in the 2-position of the pyrazole ring may arise. These can be separated in a known manner, for example by fractional crystallization or by chromatography.

Compounds of formula III are known or can be prepared by, or analogously to, known methods. For example, compounds of the formula IIIa

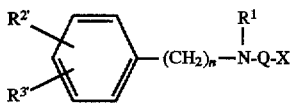 IIIa in which $R^1$, $R^{2'}$, $R^{3'}$, n, Q and X have the above meanings, can be obtained by reacting amines of formula V with compounds of formula XXX

 XXX in which Q and Y have the above meanings, with Y preferably denoting halogen, especially chlorine or bromine, and in which T represents hydroxy or a leaving group X, and, if desired, subsequently converting the group T in a known manner into a different leaving group X. The reaction can be carried out by conventional methods for aminoalkylation, for example under the conditions given above for reacting compounds of formula V with compounds of formula VI. In order to avoid secondary reactions it is advantageous to use an excess of the compound of formula XXX. If T in the compound of formula XXX represents a leaving group X, it is advantageous if the two leaving groups in the compound of formula XXX have different reactivities in order to avoid simultaneous reaction of both leaving groups with compounds of formula V. Where the amines of the formula V have been reacted with haloalcohols of the formula XXX, the hydroxyl group in the reaction product can subsequently be exchanged in a known manner for a radical X. Hence the hydroxyl compounds can be reacted, for example, with thionyl chloride in order to introduce a halogen radical X or with phosphorus halides in a known manner. Sulfonic acid radicals X can be introduced in a known manner by acylating the hydroxyl compounds with a corresponding sulfonyl halide.

Compounds corresponding to the formula IIIb

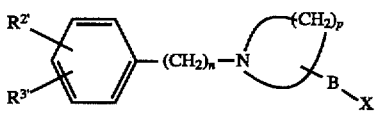 IIIb in which $R^{2'}$, $R^{3'}$, n, p, B and X have the above meanings can be obtained, for example, by reacting compounds of formula VII with compounds of the formula XXII

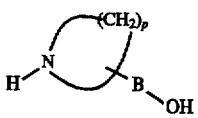 XXII in which p and B have the above meanings, and in the resulting compounds of formula XXIII

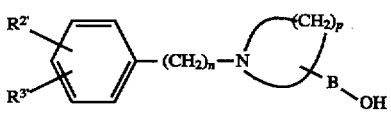 XXIII in which $R^{2'}$, $R^{3'}$, n, p and B have the above meanings, exchanging the hydroxyl group in a known manner for a radical X. The compounds of formula VII can be reacted with the amines of formula XXII by conventional aminoalkylation methods, for example under the conditions given for the process variants c) and d).

The compounds of formula IV can be obtained by reacting compounds of formula VII with aminoalcohols of formula XXIV

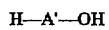 XXIV in which A' has the above meaning under conventional conditions for aminoalkylation.

Compounds of formula V are known or can be prepared by, or analogously to, known methods. For example, compounds of formula V can be obtained starting from corresponding acids of formula XIV

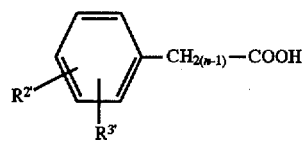 XIV in which $R^{2'}$, $R^{3'}$ and n have the above meanings. For instance, reactive acid derivatives of the acids of formula XIV can be reacted with amines of formula XIII

 XIII in which $R^1$ has the above meaning, to yield corresponding amides which can be subsequently reduced to give compounds of formula V. The reduction can take place, for example, under the conditions given for reducing the compounds of formula XI in accordance with process variant f).

Acids of formula XIV are known or can be obtained in a known manner.

Compounds of formula VI can be obtained in a known manner by reacting corresponding compounds of formula II with compounds of formula XXIX

 XXIX in which X and Q have the above meanings and T' represents a group Y, which can be eliminated by aminolysis, or hydroxy, and if desired, then converting the group T' into a group Y which can be eliminated by aminolysis. The reaction can take place under the conditions given for reacting compounds of formula II with compounds of formula III in accordance with process variant a). In order to avoid secondary reactions it is advantageous to use an excess of the compound of formula XXIX. If the radical T' in the compound of formula XXIX represents a leaving group Y, it is advantageous if the two leaving groups in the compound of formula XXIX have different reactivities. Where compounds of formula XXIX are employed in which T' denotes hydroxyl, the hydroxyl group in the resulting compounds can subsequently be converted in a known manner into a group Y. This can be done, for example, in the manner described above for preparing compounds of formula III.

Compounds of the formula VIII can be obtained by reacting compounds of the formula II with compounds of the formula XXV

 XXV in which A and X have the above meanings, and D is a protective group, which can be eliminated by solvolysis or hydrogenolysis, and then eliminating the protective group from the resulting reaction product of the formula (XXVI)

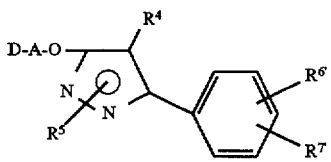

XXVI in which $R^4$, $R^5$, $R^{6'}$, $R^{7'}$, A and D have the above meanings. The reaction of compounds of formula II with the compounds of formula XXV can take place in a manner known per se, for example under the conditions given for reacting compounds of formula II with compounds of formula III in accordance with process variant a). Suitable protective groups D include, for example, radicals which can be eliminated by hydrogenolysis, e.g. benzyl, which can be eliminated by catalytic hydrogenation in the presence of a palladium catalyst.

Compounds of formula XXV are known or can be obtained in a known manner, for example in a manner analogous to the preparation of compounds of formula III. Thus compounds of the formula XXVa

XXVa in which $R^1$, Q, D and X have the above meanings, can be obtained by introducing an amino-protecting group D into amines of the formula XIII and then reacting the protected amines with compounds of formula XII, and compounds of the formula XXVb

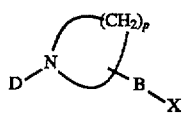

XXVb in which D, p, B and X have the above meanings, can be obtained by introducing an amino-protecting group D into an amino alcohol of the formula XXII and then converting the hydroxyl group into a radical X.

Compounds of formula IX in which Z represents hydrogen correspond to compounds of formula II. Compounds of formula IX in which Z represents a 2,3-epoxypropyl radical can be obtained in a known manner by reacting corresponding compounds of formula II with epichlorohydrin. The reaction can take place under the conditions given for reacting compounds of formula II with compounds of formula III. It is advantageous to use an excess of epichlorohydrin.

Compounds of formula X in which Z' represents hydrogen, constitute compounds of formula V. Compounds of formula X in which Z' represents the 2,3-epoxypropyl radical can be obtained in a known manner by reacting corresponding compounds of formula V with epichlorohydrin. The reaction can take place, for example, under the reaction conditions described for reacting compounds of formula V with compounds of formula VI. It is advantageous to use an excess of epichlorohydrin.

The starting compounds of formula XI are novel compounds which represent valuable intermediates for the preparation of pharmacologically active compounds, for example the compounds of the formula Ie.

Compounds of formula XI can be obtained by conventional methods for forming amides, e.g. by reacting an amine of formula V with an acid of formula XV

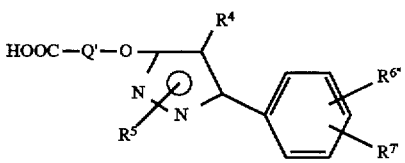

XV in which $R^4$, $R^5$, $R^{6''}$, $R^{7'}$ and Q' have the above meanings, or with a reactive acid derivative thereof, under conventional conditions for aminoacylation. Hence the amines of formula V can be reacted with reactive derivatives of acids of formula XV, desirably in a solvent which is inert under the reaction conditions, and in the presence of an acid-binding reagent. Suitable reactive derivatives of the acids of formula XV include, in particular, acid halides, symmetrical or mixed acid anhydrides, and esters. Suitable solvents include halogenated hydrocarbons such as dichloromethane, chloroform, dichloroethane or carbon tetrachloride; aromatic hydrocarbons such as benzene, toluene or chlorobenzene; cyclic ethers such as tetrahydrofuran or dioxane; dimethylformamide or mixtures of these solvents. Suitable acid-binding reagents are organic or inorganic bases. Examples of suitable organic bases include tertiary organic amines, especially tertiary lower alkyl amines such as triethylamine, tripropylamines or N-lower alkylpiperidines. Examples of suitable inorganic bases include, in particular, alkali metal carbonates or alkali metal bicarbonates. If the acylating agent employed is the acid itself or else an ester, the reaction of compound of formula V with the acid of formula XV can advantageously be carried out in the presence of a dehydrating reagent, for example a coupling reagent which is known from peptide chemistry to be suitable for forming amides. Notable examples of such reagents, which also promote the acylation by reacting in situ with the acid to form a reactive acid derivative, include in particular alkyl-, preferably cycloalkylcarbodiimides such as dicyclohexylcarbodiimide, carbonylimidazole or N-lower alkyl-2-halopyridinium salts, in particular halides or tosylates, preferably N-methyl-2-chloropyridinium iodide (=Mukaiyama's reagent). The reaction in the presence of such a coupling reagent can advantageously be carried out at temperatures of from −30° C. to +50° C. under neutral reaction conditions in solvents such as halogenated hydrocarbons and/or aromatic hydrocarbons.

If the starting compounds employed are derivatives of acids of formula XV in which $R^5$ is hydrogen, then under the aforementioned amidation reaction conditions these can initially be partially converted, especially if Q' represents a methylene group, into corresponding cyclic compounds of the formula XVa

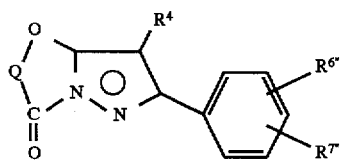

XVa in which $R^4$, $R^{6''}$, $R^{7'}$ and Q' have the above meanings, which compounds then react further with the amines of formula V.

The acids of the formula XV can be obtained by known methods by reacting corresponding compounds of formula II with a halocarboxylic ester of formula XVIa Hal—Q'—COOR$^{12}$   XVIa or with a halocarbonitrile of formula XVIb Hal—Q'—CN                                    XVIb in which Q' has the above meaning, Hal represents halogen, especially chlorine or bromine, and $R^{12}$ denotes lower alkyl, and then hydrolyzing the resulting esters or nitriles to the acids of formula XV. The reaction of a compound of formula II with a compound of formula XVIa or XVIb can be carried out under basic conditions by known methods for alkylating the oxygen atom in the 3-position of 5-phenylpyrazolin-3-ones, for example under the conditions given for process variant a). The reaction is advantageously carried out in dimethylformamide in the presence of potassium carbonate. The subsequent hydrolysis to yield an acid of formula XV preferably takes place under alkaline conditions. The acids of formula XV can be converted into corresponding reactive acid derivatives by known methods. In some cases they can be condensed to give corresponding cyclic compounds of formula XVa. Since cyclic compounds of formula XVa can be reacted further with amines of formula V, in the same way as the reactive derivatives of the acids of formula XV, it is not necessary to separate any mixtures of derivatives of the acids of the formula XV and compounds of the formula XVa.

Compounds of formula XI can also be obtained by reacting a compound of formula XXVII

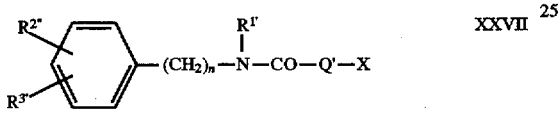

in which $R^1$, $R^{2''}$, $R^{3'}$, n, Q' and X have the above meanings with a corresponding compound of formula II. The reaction can take place in a known manner, for example under the conditions indicated in process variant a) for reacting a compounds of formula II with a compound of formula III.

Compounds of formula XXVII can be obtained by reacting an amine of formula Va

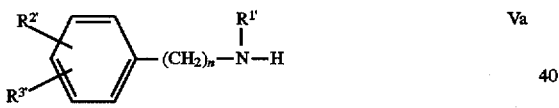

in which $R^{1'}$, $R^{2'}$, $R^{3'}$ and n have the above meanings, with a reactive derivative of an acid of formula XVII

X—Q'—COOH                                    XVII in which Q' and X have the above meanings, by conventional methods of aminoacylation. The reaction can take place, for example, under the conditions given for reacting an amine compound of formula V with a reactive derivative of an acid of formula XV. As reactive derivatives of the acids of formula XVII it is preferred to employ their halides.

With the exception of those compounds in which A" contains an NH group protected by a benzyl group, the compounds of formula XII represent corresponding compounds of formula I.

The remaining compounds of formula XIIa

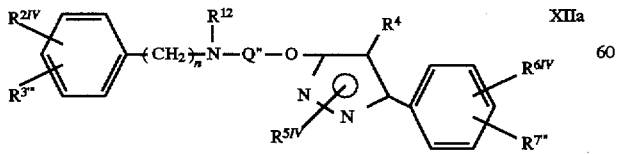

in which $R^{2IV}$, $R^{3'''}$, $R^4$, $R^{5IV}$, $R^{6IV}$, $R^{7''}$ and n have the above meanings, $R^{12}$ denotes benzyl and Q" represents a $(CH_2)_m$ group in which m denotes 2 to 8 and which may optionally be substituted in the α position to the oxygen atom by 1 or 2 lower alkyl groups, can be obtained by reacting corresponding compounds of formula IIIc

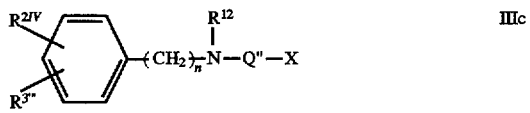

in which $R^{2IV}$, $R^{3'''}$, $R^{12}$, n, Q" and X have the above meanings under the conditions given above for the process variant a). Compounds of formula IIIc can be obtained by the methods described for preparing compounds of formula IIIa. For example, corresponding acids of formula XIV can be reacted with benzylamine to give benzylamides which can subsequently be reduced to give amines which can then be reacted with corresponding compounds of formula XXX to give compounds of formula IIIc.

The invention also relates to novel compounds corresponding to the formula XXXI

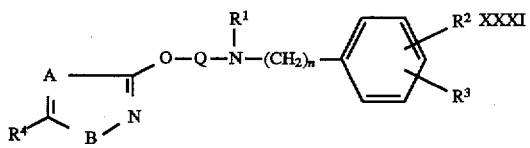

wherein $R^1$ represents hydrogen or a lower alkyl group, $R^2$ represents hydrogen, halogen, lower alkyl, lower alkoxy, hydroxy or, if Q and $R^4$ do not contain an OH group and $R^3$ is not a hydroxy, also a lower alkanoyloxy, and $R^3$ represents hydrogen, halogen, lower alkyl, lower alkoxy, hydroxy or, if Q and $R^4$ do not contain an OH group and $R^2$ is not a hydroxy, also lower alkanoyloxy or, if $R^2$ is hydrogen, also trifluoromethyl, nitro, amino, lower alkylamino, lower alkylsulfonylamino, or a lower alkanoylamino, whereby however $R^3$ does not mean nitro if $R^6$ is amino, lower alkylamino, or a lower alkanoylamino, and does not mean lower alkanoylamino if $R^6$ is amino or a lower alkylamino, or $R^2$ and $R^3$ are bonded to two adjacent carbon atoms and together form an alkylenedioxy group with 1–2 carbon atoms, $R^4$ represents thienyl or an optionally substituted phenyl group corresponding to the formula c

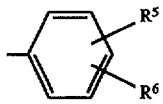

wherein $R^5$ is hydrogen, halogen, lower alkyl, lower alkoxy, hydroxy or, if Q does not contain an OH group, and $R^2$, $R^3$, and $R^6$ are not hydroxy, also a lower alkanoyloxy, and $R^6$ represents hydrogen, halogen, lower alkyl, lower alkoxy, hydroxy or, if Q does not contain an OH group, and $R^2$, $R^3$, and $R^5$ are not hydroxy, also a lower alkanoyloxy, or if $R^5$ is hydrogen, also a trifluoromethyl, nitro, amino, lower alkylamino, or a lower alkanoylamino, A represents nitrogen or an $R^7$-C group in which $R^7$ is hydrogen or a lower alkyl group, B represents oxygen or, if A is nitrogen, also sulfur, n is an integer from 1 to 5, and Q represents a $(CH_2)_m$ group where m is an integer from 2 to 8 and which may optionally be substituted by a lower alkyl, or represents the 2-hydroxypropylene chain, or a physiologically acceptable acid addition salt thereof.

To the extent that the substituents $R^2$, $R^3$, $R^5$, and $R^6$ of the phenyl rings represent or contain lower alkyl groups in the compounds of formula XXXI, they can be straight or branched and in particular contain 1 to 4 carbon atoms, preferably 1 carbon atom, and constitute methyl or methoxy in particular. To the extent that the substituents represent halogen, fluorine, chlorine, or bromine are preferred, particularly preferably fluorine or chlorine.

Substituents $R^2$ and $R^3$ are preferably located in the 3-and/or 4-position and preferably constitute a lower alkoxy group, especially methoxy.

Substituent $R^4$ preferably represents an optionally substituted phenyl group. Any substituents $R^5$ and $R^6$ in this phenyl group are preferably located in the 2- and/or 3-position. A phenyl group $R^4$ is preferably unsubstituted or monosubstituted, i.e. $R^6$ is preferably hydrogen, while $R^5$ is preferably hydrogen, lower alkoxy, or even halogen, lower alkyl, or hydroxy.

The Q group preferably represents a preferably unsubstituted alkylene chain $(CH_2)_m$ in which m represents 2-8. The $(CH_2)_m$ group can preferably contain 2-6, especially 3 or 5 and particularly preferably 3 carbon atoms.

Substituent $R^1$ preferably represents a lower alkyl group, especially methyl.

According to the invention, the novel compounds of formula XXXI and their acid addition salts are obtained by, in known fashion a) to prepare a compound corresponding to formula XXXIa

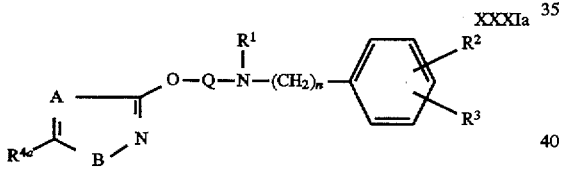

XXXIa wherein $R^1$, $R^2$, $R^3$, A, B, Q, and n have the meanings given above, and $R^{4a}$ has the meaning given for $R^4$ with the exception of residues containing NH, a compound corresponding to the formula XXXII

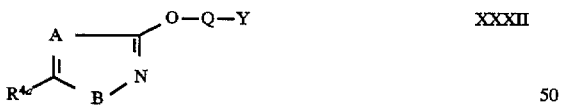

XXXII wherein $R^{4a}$, A, B, and Q have the above meanings, and Y represents an aminolytically clearable volatile group, is reacted with a compound corresponding to the formula XXXIIIa

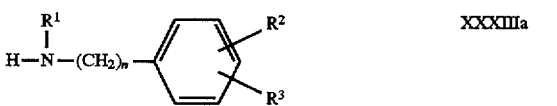

XXXIIIa where $R^1$, $R^2$, $R^3$, and n have the above meanings, with the proviso that any free hydroxy and/or amino groups $R^2$ and/or $R^3$ are provided with a protective group, and then any hydroxy-protective and/or amino-protective groups are split off again, or b) to prepare a compound corresponding to formula XXXIb

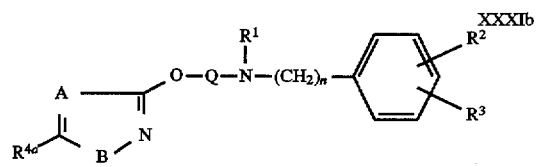

XXXIb wherein $R^1$, $R^2$, $R^3$, A, B, Q, and n have the above meanings, and $R^{4b}$ has the meaning given for $R^4$ with the exception of residues containing hydroxy and/or NH, a compound corresponding to the formula XXXIVa

XXXIVa wherein $R^{4b}$, A, and B have the above meanings, is reacted with a compound of the formula XXXV

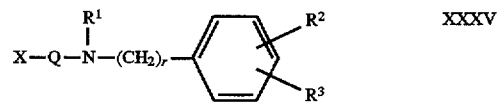

XXXV wherein $R^1$, $R^2$, $R^3$, n, and Q have the above meanings, with the proviso that any free hydroxy and/or amino groups are provided with a protective group, and X represents a cleavable volatile group, and then any hydroxy-protective and/or amino-protective groups are split off again, or c) to prepare a compound corresponding to formula XXXIc

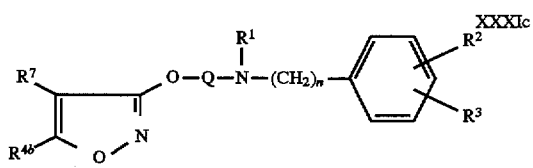

XXXIc wherein $R^1$, $R^2$, $R^3$, $R^{4b}$, $R^7$, Q, and n have the above meanings, a compound corresponding to the formula XXXVI

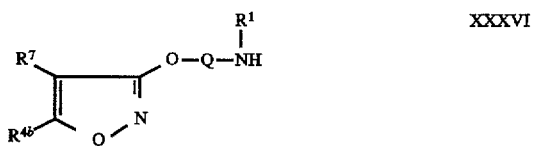

XXXVI wherein $R^1$, $R^7$ and $R^{4b}$ have the above meanings, is reacted with a compound of formula XXXVII

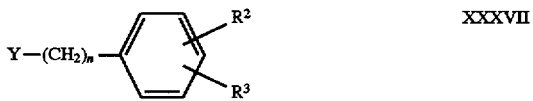

XXXVII wherein Y, n, $R^2$, and $R^3$ have the above meanings, with the proviso that free amino and/or hydroxy groups $R^2$ and/or $R^3$ are provided with a protective group, and then any hydroxy-protective and/or amino-protective groups are split off again, or d) to prepare a compound corresponding to formula XXXId

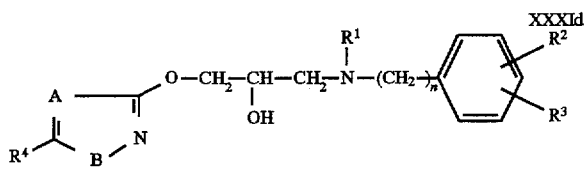

wherein $R^1$, $R^2$, $R^3$, $R^{4b}$, A, B, and n have the above meanings, a compound corresponding to the formula XXXIV

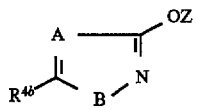

wherein $R^{4b}$, A, and B have the above meanings, and Z represents a 2,3-epoxypropyl group or, if A is an $R^7$—C group, Z may also represent hydrogen, is reacted with a compound of formula XXXIII

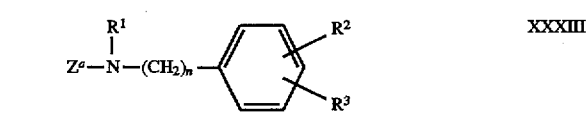

wherein $R^1$, $R^2$, $R^3$, and n have the above meanings, with the proviso that any free hydroxy and/or amino groups are provided with a protective group, and $Z^a$ represents hydrogen or, if Z is hydrogen in the compound of formula XXXIV, $Z^a$ may also represents a 2,3-epoxypropyl group, and then any hydroxy-protective and/or amino-protective groups are split off again, or e) to prepare a compound corresponding to formula XXXIe

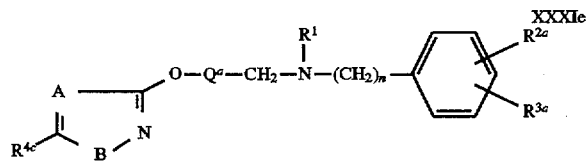

wherein $R^1$, n, A, and B have the above meanings, $R^{4c}$ has the meaning given for $R^{4b}$ with the exception of residues containing a nitro and/or a lower alkanoyloxy group, $R^{2a}$ and $R^{3a}$ have the meanings given for $R^2$ and $R^3$ with the exception of nitro, lower alkanoyloxy, and lower alkanoylamino, and $Q^a$ represents a $(CH_2)_{m^a}$ group in which $m^a$ represents 3 or 4 and which may optionally be substituted by a lower alkyl group, a compound corresponding to the formula XXXVIII

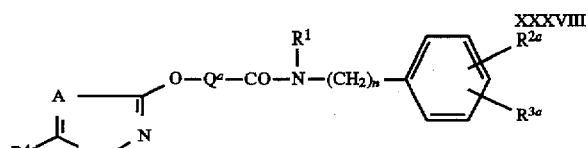

wherein $R^1$, $R^{2a}$, $R^{3a}$, $R^{4c}$, A, B, $Q^a$, and n have the above meanings, with the proviso that any free hydroxy and/or amino groups are provided with a protective group, are reduced, and then any hydroxy-protective and/or amino-protective groups are split off again, or f) to prepare a compound corresponding to formula XXXIf

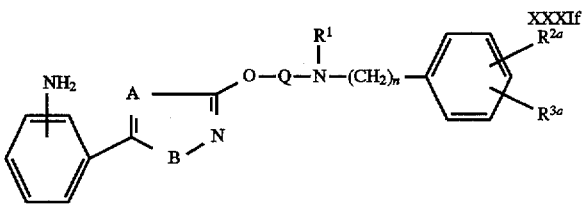

wherein $R^1$, $R^{2a}$, $R^{3a}$, A, B, Q, and n have the above meanings, a compound corresponding to the formula XXXIg

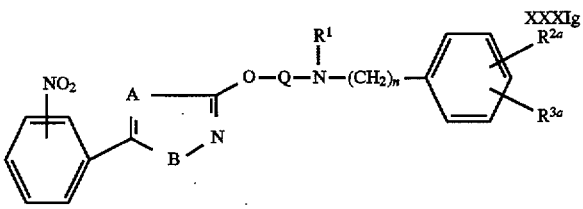

wherein $R^1$, $R^{2a}$, A, B, Q, and n have the above meanings, and $R^{3b}$ has the meaning given for $R^3$ with the exception of residues containing alkanoyl, are reduced, or g) to prepare a compound corresponding to formula XXXIh

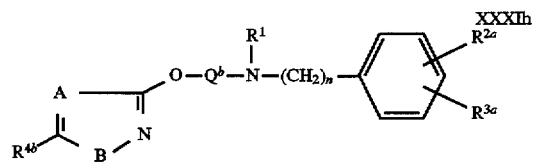

wherein $R^1$, $R^{4b}$, A, B, and n have the above meanings, $Q^b$ has the meaning given for Q with the exception of the 2-hydroxypropylene chain, and $R^{2b}$ and $R^{3c}$ have the meanings given for $R^2$ and $R^3$ with the exception of OH groups, with the proviso that at least one of the substituents $R^{2b}$ and $R^{3c}$ and/or of substituents $R^5$ and $R^6$ contained in $R^{4b}$, represents a lower alkanoyloxy or a lower alkanoylamino group, a compound corresponding to the formula XXXIX

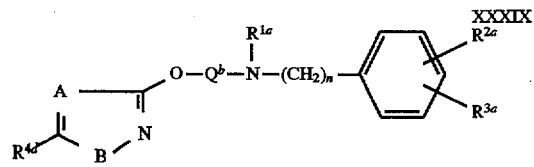

wherein $R^{2a}$, $R^{3b}$, A, B, $Q^b$, and n have the above meanings, $R^{1a}$ represents a lower alkyl or an aminoprotective group, and $R^{4d}$ has the meaning given for $R^4$ with the exception of residues containing a lower alkanoyl group, and which may optionally contain hydroxy-protective and/or amino-protective groups, with the proviso that at least one of the substituents $R^{2a}$ and $R^{3b}$ and/or of the substituents $R^5$ and $R^6$ contained in $R^{4d}$, represents a free OH or $NH_2$ group, are acylated, and then any protective groups are split off again, or h) to prepare a compound corresponding to formula XXXIi

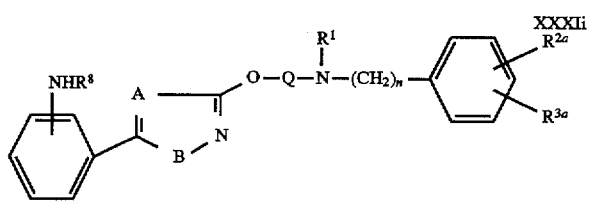

wherein A, B, Q, $R^1$, $R^{2a}$, $R^{3a}$, and n have the above meanings, and $R^8$ represents a lower alkyl group, a compound corresponding to the formula XXXIj

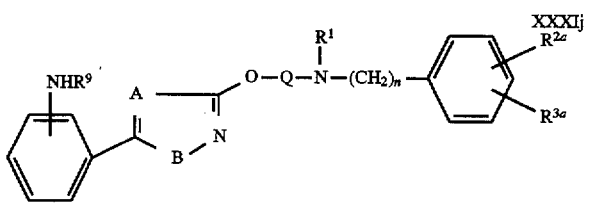

wherein $R^1$, $R^{2a}$, $R^{3a}$, A, B, and n have the above meanings, and $R^9$ represents a lower alkanoyl group, are reduced, and, if desired, in a compound of formula XXXI in which $R^2$, $R^3$, $R^5$, and/or $R^6$ is methoxy, demethylating the methoxy group to form a hydroxy group, and/or, if desired, in a compound of formula XXXI in which $R^1$ represents hydrogen, alkylating the compound to form a corresponding compound of formula XXXI in which $R^1$ represents a lower alkyl group, and/or, if desired, converting a free compounds of formula XXXI into a corresponding acid addition salt or converting an acid addition salt to a corresponding free base of formula XXXI.

The reactions of compounds of formula XXXII with compounds of formula XXXIIIa according to method version a) and the reaction of compounds of formula XXXVI with compounds of formula XXXVII according to method version c) can be performed by methods conventionally employed for alkylating amines. As the aminolytically splittable residue Y in the compounds of formulas II and VII, halogens are suitable, such as chlorine, bromine, or iodine, preferably bromine or chlorine, as well as organic sulfonic acid residues, for example residues of lower alkanesulfonic acids such as for example methanesulfonic acid or aromatic sulfonic acids such as benzenesulfonic acid or benzenesulfonic acids substituted by a lower alkyl or by halogen, e.g. toluenesulfonic acids or bromobenzenesulfonic acids. The reactions can be conducted in an organic solvent that is inert under the reaction conditions, under basic conditions. Advantageously, an at least equivalent quantity of an acid-binding base is added to the reaction mixture. Inorganic or organic alkali metal compounds are suitable as bases for example. Examples of suitable bases include alkali metal carbonates such as, for example, potassium carbonate or also alkali metal hydroxides, alkali metal hydrides such as sodium hydride or a lower alkali metal alcoholates such as, for example, potassium tert-butylate or alkali metal amides such as e.g. lithium amide. Suitable inert organic solvents include dimethylformamide, tetramethylurea, or depending on the nature of the base added as the acid-bonding agent, cyclic ethers such as tetrahydrofuran, lower alcohols or aromatic hydrocarbons such as benzene or toluene or mixtures of the foregoing solvents. In the reaction of compounds in which A represents nitrogen, it can be advantageous for the solvent to be added to the reaction mixture only after deprotonization has taken place by reacting the reactants with the base. The reaction can be conducted at elevated temperatures, for example temperatures between 60° C. and the boiling point of the reaction mixture. Advantageously, the reaction is conducted, for example, using an inorganic base such as potassium carbonate or sodium hydride in an inert solvent such as dimethylformamide, preferably at temperatures between 80° and 120° C. Any free hydroxy groups in the Q group and/or free hydroxy and/or amino substituents of the phenyl rings can be protected during the reaction by protective groups that can be readily split off again later. Method version a) is especially suitable for making compounds of formula XXXI in which A represents nitrogen.

The reaction of compounds of formula XXXIVa with compounds of formula XXXV according to method version b) can be performed in a known manner for forming heteroarylether compounds by alkylation of hydroxyheteroaryl compounds. Halogens such as chlorine, bromine, or iodine or even organic sulfonic acid residues can preferably be used as the volatile group X in the compounds of formula XXXV, for example residues of lower alkanesulfonic acids such as for example methanesulfonic acid or of aromatic sulfonic acids such as benzenesulfonic acid or benzenesulfonic acids substituted by a lower alkyl or halogen, e.g. toluenesulfonic acids or bromosulfonic acids. In general, roughly equivalent amounts of compounds of formulas XXXIVa and XXXV are used. If $R^1$ represents hydrogen or the compounds have free amino groups as substituents, it is advantageous to protect the latter with an aminoprotective group that can be split off later in order to avoid secondary reactions. Any free hydroxy groups in the compounds can be protected during the reaction by a hydroxyprotective group that can be readily split off again later. The reaction is advantageously conducted in an organic solvent that is inert under the reaction conditions, under basic conditions. The solvents, bases, and reaction conditions listed above for method versions a) and c) can be used. If desired, catalytic amounts of an iodide salt, an alkali metal or ammonium iodide such as potassium iodide or tert-butylammonium iodide can be used to accelerate the reaction. The reaction can be conducted at temperatures between room temperature and the boiling point of the reaction mixture. Advantageously, the reaction is conducted, for example, using an inorganic base such as potassium carbonate or sodium hydride in an inert solvent such as dimethylformamide, preferably at temperatures between 80° and 120° C.

The reaction of compounds of formula XXXIV with compounds of formula XXXIII in accordance with method version d) can be performed in a known manner employing the usual methods for reacting alcohols or amines with epoxides. Thus, compounds of formula XXXIV can be reacted with compounds of formula XXXIII in an organic solvent which is inert under the reaction conditions, under basic conditions. The solvents and bases used for method versions a), b), and c) may be used. The reaction temperature can be in the range from 60° to 120° C. Depending on the nature of the reaction conditions, the reaction time may range between 4 and 12 hours. Advantageously, the reaction is conducted, for example, in an inert solvent such as dimethylformamide in the presence of an organic base such as potassium carbonate at temperatures of approximately 100° C.

Reduction of compounds of formula XXXVIII in accordance with method version e) can take place according to the usual methods employed for reduction of amides. Complex metal hydrides capable of amide reduction are suitable as reducing agents, especially aluminum hydrides such as lithium aluminum hydride or lower alkylaluminum hydrides, for example diisobutylaluminum hydride. The reaction takes place in an anhydrous solvent which is sufficiently inert under the reaction conditions. Cyclic ethers such as tetrahydrofuran or dioxane or open-chain ethers such as ethylene glycol dimethyl ether or diethylene glycol dimethyl ether, optionally mixed with aromatic hydrocarbons such as benzene or toluene, are suitable as solvents. Depending on the nature of the reducing agent used, the reaction can be conducted at elevated temperatures, for example the boiling point of the reaction mixture. For example, the reaction with lithium aluminum hydride at the boiling point of the reaction mixture has proven to be satisfactory. The reaction time can be between 1 and 10 hours.

The compounds of formula XXXIf can be prepared in a known manner from compounds of formula XXXIg and according to method version f). Thus, the nitro compounds of formula XXXIg can be reduced in a known manner to corresponding amino compounds of formula XXXIf. The reduction can be conducted according to the usual methods employed for making aniline derivatives from corresponding nitrophenol derivatives in an organic solvent which is inert under the reaction conditions, with the reaction conditions being chosen so that the heterocyclic ring is not split. Thus, for example, reduction can take place by catalytic hydration in the presence of catalytic amounts of Raney nickel or using hydrazine compounds as reducing agents.

The acylation of compounds of formula XXXIX according to method version g) can be conducted according to the usual known methods for the formation of amides and/or phenol esters by reacting compounds of formula XXXIX with a reactive derivative of a corresponding lower carboxylic acid, for example a lower carboxylic acid halide or anhydride. For example, the reaction can take place in the presence of an acid-binding medium, for example an organic base such as a tri(lower alkyl)amine or pyridine in an organic solvent which is inert under the reaction conditions, for example halogenated hydrocarbons such as dichloromethane or cyclic ethers such as tetrahydrofuran or pyridine.

Reduction of compounds of formula XXXIi according to method version h) can be conducted under conventional conditions for reduction of amides and, for example, can be conducted under the conditions specified for the reduction of compounds of formula XXXVIII in accordance with method version e).

If the Q group contains a hydroxy group and/or there are free hydroxy substituents on phenyl residues of the compounds and/or the compounds contain free amino groups which should not participate in the reaction, these groups must be protected in a known manner during the reactions described above and during the preparation of the starting materials by means of protective groups that can be split off again easily. Suitable protective groups for hydroxyl groups, which can be readaily removed again after the reaction, are known, for example, from E. McOmie "*Protective Groups in Organic Chemistry,*" Plenum Press 1971. For example, esters, for example acetates, readily cleavable carbonates such as benzylcarbonate and readily clearable ethers such as tetrahydropyranyl ether or trimethylsilyl ether for example are suitable for protecting a hydroxy group. In each case, protective groups must be chosen that are not affected during the reactions that are conducted and which can be removed off later under conditions under which the products that are formed are not affected. Preferably, etherprotective groups such as trimethylsilyl ether can be used. The free NH groups can also be protected in a known manner, if desired, by means of protective groups that can be readily removed again. Suitable protective groups that can be split off again readily after the reaction for NH groups are known, for example, from E. McOmie "*Protective Groups in Organic Chemistry,*" Plenum Press 1971. For example, the protective groups known from peptide chemistry are suitable for protection of a NH function, for example carbamates that can be split off readily. In each case, aminoprotective groups must be selected that are not affected during the reactions conducted and which then can be removed under conditions under which the products that are formed are not affected.

In compounds of formula XXXI containing methoxy substituents, the hydroxy group can be released later if desired. Methoxy groups can be split using methods suitable for cleaving methoxyaryl ethers in known manner to produce hydroxy groups. For example, the ether can be cleaved by treatment with hydrogen iodide or hydrogen bromide in a solvent which is inert under the reaction conditions, for example acetane hydride or acetic acid, or with iodine trimethylsilane or boron tribromide in a halogenated hydrocarbon such as dichloromethane. Any lower alkanoyloxy groups are likewise split under ether-splitting conditions.

The compounds of formula XXXI can be isolated and purified from the reaction mixture in a known manner. Acid addition salts can be converted in the usual manner to the free bases, and the free bases can be converted in known manner, if desired, into pharmacologically acceptable acid addition salts.

Suitable pharmacologically acceptable acid addition salts of the compounds of formula XXXI include, for example, their salts with, for example, inorganic acids, e.g. hydrohalic acids especially hydrochloric acid, sulfuric acid, or phosphoric acids, or with organic acids, for example. lower aliphatic monocarboxylic or dicarboxylic acids such as maleic acid, fumaric acid, lactic acid, tartaric acid, or acetic acid, N-acetylglutaminic acid, or sulfonic acids, for example lower alkanesulfonic acids such as methanesulfonic acid or benzenesulfonic acids, optionally substituted in the benzene ring by halogen or lower alkyl, such as p-toluenesulfonic acid or cyclohexylaminosulfonic acid.

If the Q group in the compounds of formula XXXI represents a hydroxypropylene chain or an alkylene chain substituted by a lower alkyl, the compounds contain an asymmetric center and can occur in two optically active forms or as a racemate. The present invention comprises both the racemic mixtures and the optical isomers of these compounds of formula XXXI. The optically active compounds can be obtained in a known manner from the racemic mixtures by conventional separating procedures, for example by chromatographic separation on chiral separating materials or fractional crystallization of suitable salts with optically active acids. Compounds free of enantiomers can also be prepared by synthesis from suitable starting compounds free of enantiomers.

The starting compounds of formula XXXII can be obtained in a known manner by reacting suitable compounds of formula XXXIVa with compounds of formula XL $$X^a\text{---}Q\text{---}T \qquad\qquad XL$$

wherein Q has the meaning given above, $X^a$ represents halogen, and T represents an aminolytically cleavable group Y or hydroxy, and then converting group T, to the extent the latter is hydroxy, into an aminolytically cleavable group Y and/or converting any methoxy substituents that are present in residue $R^{4b}$ if desired in a known manner into hydroxy. The reaction of the compounds of formula XXXIVa with the compounds of formula XL can be performed under the conditions specified for reacting compounds of formula XXXIVa with compounds of formula XXXV according to method version b). To avoid secondary reactions, it is advantageous to use an excess of compounds of formula XL. To the extent that the residue T in compounds of formula XL represents an aminolytically cleavable volatile group Y, it is advantageous for the two volatile groups contained in the compound of formula XL to have different reactivities. If compounds of formula XL are used, the hydroxy group in the resulting product compound can then be converted in a known manner to a group Y. Thus, to introduce a halogen residue Y, the hydroxy compounds can be reacted, for example, with thionyl chloride or with phosphorus halides in a known manner. Sulfonic acid residues Y can be introduced in a known manner, with the hydroxy compounds being acylated with a corresponding sulfonic acid halide. The cleaving of methoxy substituents to hydroxy can be carried out in a known manner, for example under the conditions given above for releasing hydroxy groups from methoxy substituents of the compounds of formula XXXI.

Compounds corresponding to the formula XXXIVc

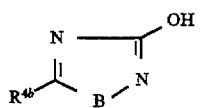
XXXIVc wherein $R^{4b}$ and B have the meanings given above, are known, or can be obtained in a known manner from compounds corresponding to the formula XLI

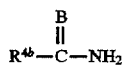
XLI wherein $R^{4b}$ and B have the meanings given above, with the amides or thioamides of formula XLI being reacted with oxalyl chloride of formula XLII

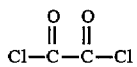
XLII and the resulting reaction products being reacted further with trimethylsilylazide. If B represents sulfur, the thioamides of formula XLI are initially reacted with oxalyl chloride at temperatures between −30° and +30° C. in an organic solvent which is inert under the reaction conditions, for example an aromatic hydrocarbon or acetone. The cyclic dione compounds corresponding to the formula XLIII then form

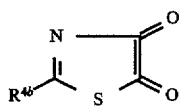
XLIII where $R^{4b}$ has the meaning given above, which can be reacted further, if desired, either in isolation or directly in situ with heating with trimethylsilylazide. Reaction with trimethylsilylazide takes place in an organic solvent which is inert under the reaction conditions, for example an aromatic hydrocarbon, at temperatures between 90° and 130° C. The cyclic dione is changed in an intermediary fashion into an unstable thioacylisocyanate by splitting off CO, which reacts with the azide with cyclization into corresponding compounds of formula XXXIVc. If B represents oxygen, the reaction of amides of formula XLI with oxalyl chloride may take place in an inert organic solvent, for example a halogenated hydrocarbon, at temperatures between 30° and 50° C. The corresponding acylisocyanates of formula many of which are known,

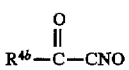
XLIV are obtained directly, where $R^{4b}$ has the meaning given above. The acylisocyanates of formula XLIV can be isolated or reacted directly in situ with trimethylsilylazide. When the acylisocyanates are heated with the trimethylsilylazide to temperatures between 40° and 60° C., preferably the boiling point of the reaction mixture, the acylisocyanates react with the azide with cyclization into the corresponding compounds of formula XXXIVc.

The amides and thioamides of formula XLI are known or can be obtained by known methods. For example, acid chlorides corresponding to the formula XLV

XLV can be reacted in a known manner into corresponding amides of formula XLI, with $R^{4b}$ having the meaning given above. Thioamides of formula XLI can be prepared from the corresponding amides using conventional methods used for exchanging oxygen for sulfur, for example according to the method described by Lawesson et al. (see Tetrahedron 35, 2433 to 2437) by reacting with, 2,4-bis(methoxyphenyl)-1,3-dithia-2,4-diphosphetane-2,4-disulfide (known as Lawesson's reagent).

Compounds corresponding to the formula XXXIVb

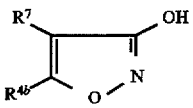
XXXIVb wherein $R^{4b}$ and $R^7$ have the meanings given above, can be obtained in a known manner starting from compounds corresponding to the formula XLVIa or XLVIb

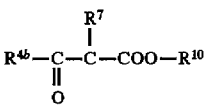
XLVIa and

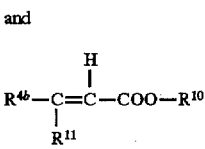
XLVIb wherein $R^{4b}$ and $R^7$ have the meanings given above, $R^{10}$ represents a lower alkyl group, and $R^{11}$ represents the imidazolyl residue, by cyclizing the compounds of formulas XLVIa or XLVIb into compounds of formula XXXIVb by reacting with hydroxylamine followed by acid treatment. The reaction with hydroxylamine advantageously takes place in a lower alkanol in the presence of a strong base, for example an alkali metal hydroxide or alcoholate. During the cyclization of compounds of formula XLIVa, mixtures of isooxazole-3-ole compounds of formula XXXIVb with corresponding regioisomeric isooxazole-5-ones and their tantomers can occur, whose composition can vary depending on the nature of the residues $R^{4b}$ and $R^7$. In order to keep the yield of compounds of formula XXXIVb as high as possible, it is advantageous to process the β-ketoesters of formula XLIVa at low temperatures, e.g. temperatures in the range from −50° to −75° C., and then to add the reaction mixture rapidly to the acid, for example concentrated hydrochloric acid.

The compounds of formulas XLVIa and XLVIb are known or can be prepared in a known manner. For example, compounds of formula XLVIb can be prepared in a known manner by adding the $R^{11}$ residue to unsaturated esters corresponding to the formula XLVII

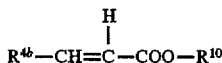 XLVII wherein $R^{4b}$ and $R^{10}$ have the meanings given above. The unsaturated esters can first be brominated to produce the corresponding dibromocarboxylic acid esters and these can then be reacted under HBr-splitting conditions with the imidazole.

Compounds corresponding to the formula XXXIVd

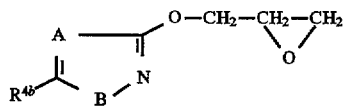 XXXIVd wherein $R^{4b}$, A, and B have the meanings given above, can be obtained in a known manner from compounds of formula XXXIVa by reacting with epichlorohydrin. The reaction can be conducted under the conditions specified for the reaction of compounds of formula XXXIV with compounds of formula XXXIII. An excess of epichlorohydrin is advantageous in this regard.

The compounds of formula XXXIIIa are known or can be prepared in accordance with known methods or analogously to known methods. For example, compounds of formula XXXIIIa can be obtained from corresponding acids of formula XLVIII

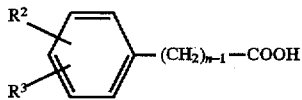 XLVIII wherein $R^2$, $R^3$, and n have the meanings given above. Thus, for example, acid derivatives of the acids of formula XLVIII that are capable of reaction are reacted with amines corresponding to the formula IL

 IL $R^1$—$NH_2$ wherein $R^1$ has the meaning given above to form corresponding amides, and these are then reduced to compounds of formula XXXIIIa. This reduction can be carried out, for example, under the conditions that are specified for the reduction of compounds of formula XXXVIII according to method version e). Acids of formula XLVIII are known or can be obtained in a known manner.

The compounds of formula XXXIII in which $Z^a$ represents a 2,3-epoxypropyl residue can be obtained in a known manner from corresponding compounds of formula XXXIIIa by reacting with epichlorohydrin.

The compounds of formula XXXV are known or can be prepared by known methods or analogously to known methods. For example, compounds of formula XXXV can be obtained by reacting amines of formula XXXIIIa with compounds corresponding to the formula XLa

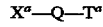 XLa $X^a$—Q—$T^a$ wherein $X^a$ and Q have the meanings given above, and $T^a$ represents a volatile group X or hydroxy, and then the group $T^a$, if desired, is converted in a known manner to another volatile group X. The reaction can be conducted using the methods that are conventionally employed for aminoalkylation, for example under the conditions specified for reacting compounds of formula XXXII with compounds of formula XXXIIIa according to method version a). To avoid secondary reactions it is advantageous to use an excess of compounds of formula XLa. To the extent that the residue $T^a$ in the compounds is a volatile group X, it is advantageous for the two volatile groups contained in the compound of formula XLa to have different reactivities in order to avoid simultaneous reaction of the two volatile groups with compounds of formula XXXIIIa. To the extent the compounds of formula XXXIIIa are reactive with halogen alcohols of formula XLa, the hydroxy group can then be exchanged in the reaction product in a known manner for a residue X. This can be done for example in the manner described above for the preparation of compounds of formula XXXII.

The compounds of formula XXXVI can be obtained by reacting compounds of formula XXXIVb with compounds with general formula L

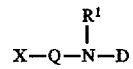 L

X—Q—N—D wherein $R^1$, X, and Q have the meanings given above, and D is a removable aminoprotective group, and the protective group D is split off again from the reaction products obtained. Reaction of compounds of formula XXXIVb with compounds of formula L can be carried out a known manner, for example under the reaction conditions specified for the reaction of compounds of formula XXXIVb with compounds of formula XXXV according to method version b).

The compounds of formula L are known or can be obtained in a known manner, for example analogously to the preparation of compounds of formula XXXV. Thus, for example, compounds of formula L can be obtained by introducing an aminoprotective group D into amines of formula IL followed by reaction of the protected amines with compounds of formula XLa, optionally followed by an exchange of a hydroxy group $T^a$ for a residue X.

The starting compounds of formula XXXVIII are novel compounds that represent valuable intermediates for the preparation of pharmacologically active compounds, for example the compounds of formula XXXIe.

The compounds of formula XXXVIII can be obtained according to conventional methods for amide formation in which amines of formula XXXIIIa are reacted with acids corresponding to the formula LI

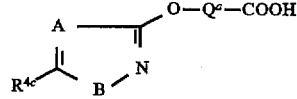 LI wherein $R^{4c}$, A, B, and $Q^a$ have the meanings given above, or their reactive acid derivatives, are reacted under conditions that are conventional for aminoacylation. Thus, the amines of formula XXXIIIa can be reacted advantageously with reactive derivatives of the acids of formula LI in an organic solvent that is inert under the reaction conditions and in the presence of an acid-binding reagent. As a reactive derivative of acids of formula LI, acid halides in particular and optionally mixed acid anhydrides or esters may be employed. Suitable solvents include halogenated hydrocarbons such as dichloromethane, aromatic hydrocarbons such as benzene, toluene, or chlorobenzene, cyclic ethers such as tetrahydrofuran or dioxane, dimethylformamide or mixtures of these solvents. Suitable acid-binding reagents include organic or inorganic bases. Examples of suitable organic bases include tertiary organic amines, especially tertiary lower alkylamine such as triethylamine, tripropylamine, or N-(lower alkyl)piperidine. Suitable inorganic bases include, in particular, alkali metal carbonates or bicarbonates. If the acids themselves or their esters are used as acylating agents, the reaction of the compounds of formula XXXIIIa with the acids of formula LI can advantageously be carried out in the presence of a dehydrating reagent, for example a coupling reagent known from peptide chemistry to be suitable for amide formation. Examples of such reagents that promote acylation by virtue of the fact that they react with the acid in situ to form a reactive acid derivative include, in particular, alkyl, preferably cycloalkylcarbodiimides such as dicyclohexylcarbodiimide, carbonylimidazole, or N-(lower alkyl)-2-halogenpyridinium salts, especially halides or tosylates, preferably N-methyl-2-chloropyridinium iodide (=Mukajama reagent). The reaction in the presence of such a coupling reagent can advantageously be conducted at temperatures of −30° C. to +50° C. under neutral reaction conditions in solvents such as halogenated hydrocarbons and/or aromatic hydrocarbons.

The acids of formula LI can be obtained in accordance with known methods by reacting suitable compounds of formula XXXIVa with halogen carboxylic acid esters or nitriles corresponding to the formulas LIIa and LIIb

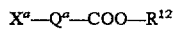   LIIa and

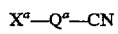   LIIb wherein $X^a$ and $Q^a$ have the meanings given above, and $R^{12}$ is a lower alkyl group, then hydrolyzing the resulting esters or nitriles to the acids of formula LI. The reaction of the compounds of formula IVa with the compounds of formula LIIa or LIIb can be conducted in a known manner, for example under the conditions specified for method version b). Advantageously, the reaction is carried out in dimethylformamide in the presence of a strong base, for example sodium hydride, at elevated temperatures, for example temperatures between 80° and 100° C. The subsequent hydrolysis to the acids of formula LI is preferably conducted under alkaline conditions. The acids of formula LI can be converted in a known manner into their reactive acid derivatives.

The compounds of formula XXXIX, with the exception of those compounds in which $R^{1a}$ represents an aminoprotective group, constitute corresponding compounds of formula XXXI. Compounds of formula XXXIX in which $R^{1a}$ represents an aminoprotective group can be obtained from corresponding compounds of formula XXXI in which $R^1$ represents hydrogen by introducing an aminoprotective group in a known manner.

The compounds of the invention and their pharmacologically acceptable acid addition salts are characterized by advantageous pharmacological properties. In particular the compounds act on the cardiac circulation and are characterized by pronounced heart rate lowering effects. Thus they have an activity profile which is advantageous for treating ischaemic conditions such as, for example, coronary heart disease, since cytoprotective effects are also present in the group of substances.

The cardioactive properties of the compounds can be demonstrated in vitro and in vivo in standard pharmacological test methods.

Description of the pharmacological test methods:
1. Determination of the minimum toxic dose.

Maximum doses of 300 mg of test substance per kg are administered perorally to male mice weighing 20 to 25 g. The animals are carefully observed for 3 hours for symptoms of toxicity. In addition, over a period of 72 hours following administration all symptoms and fatalities are recorded. Concomitant symptoms are likewise observed and recorded. If death or severely toxic symptoms are observed, increasingly smaller doses are administered to further mice until no further toxic symptoms appear. The lowest dose which induces death or severely toxic symptoms is reported in the following Table A as the minimum toxic dose. The example numbers given in Table A relate to the subsequent preparation examples.

TABLE A

| Test Substance Example No. | Minimum toxic dose mg/kg mouse p.o. |
| --- | --- |
| 1 | >300 |
| 7 | >300 |
| 8 | >300 |
| 9 | >300 |
| 15 | >300 |
| 17 | >300 |
| 18 | >300 |
| 21 | >300 |
| 26 | >300 |
| 44 | 300 |
| 46 | >300 |
| 47 | >300 |
| 54 | 100 |
| 55 | 100 |
| 57 | 100 |
| 61 | 300 |
| 73 | 300 |
| 74 | 300 |
| 75 | 100 |
| 76 | 300 |
| 78 | 100 |
| 79 | 100 |
| 80 | 300 |

2. In vitro demonstration of heart rate-lowering effect.

The direct influence of the active substances on the heart rate (FRQ) was tested on spontaneously beating, isolated right atria of male Pirbright-white guinea-pigs weighing 250–300 g. In the following Table B, FRQ 75 denotes that concentration, in µmol/liter, at which 20 minutes after the adminstration of the substance there is a reduction in the rate to 75% of the initial value. The example numbers given for the test substances in Table B relate to the subsequent preparation examples.

TABLE B

| Test substance Example No. | Heart rate-lowering effect Effective concentration in µmol/liter to attain FRQ 75% |
| --- | --- |
| 1 | 1.6 |
| 3 | 1.7 |
| 6 | 6.1 |
| 7 | 2.6 |
| 8 | 2.5 |
| 9 | 5.7 |
| 12 | 3.5 |
| 13 | 0.9 |
| 15 | 4.3 |
| 17 | 4.0 |
| 18 | 1.3 |
| 21 | 3.4 |
| 26 | 5.6 |
| 27 | 1.9 |
| 32 | 9.1 |
| 44 | 1.6 |
| 46 | 7.0 |

TABLE B-continued

| Test substance Example No. | Heart rate-lowering effect Effective concentration in μmol/liter to attain FRQ 75% |
|---|---|
| 47 | 6.4 |
| 51 | 3.0 |
| 52 | 3.5 |
| 53 | 4.9 |
| 54 | 1.5 |
| 65 | 1.3 |
| 66 | 2.8 |
| 89 | 1.5 |
| 90 | 2.3 |
| 91 | 1.4 |
| 92 | 1.3 |
| 93 | 2 |
| 96 | 2.0 |
| 97 | 1.6 |
| 98 | 0.68 |
| 99 | 2.1 |
| 100 | 2.8 |
| 107 | 0.64 |
| 111 | 1.2 |
| 113 | 1.6 |

3. In vitro demonstration of the cytoprotective effect.

The cytoprotective effect was tested on isolated left atria of male Pirbright-white guinea-pigs weighing 250 to 300 g. The atria were maintained in a nutrient solution and electrically stimulated. A temporary hypoxia was induced by gassing the nutrient solution with nitrogen for 60 minutes. As a result of the hypoxia, the atria contracted. The measurement parameter used was the integral of the contraction over the period of hypoxia. In the following Table C the effective concentration is given in μmol/liter at which the integral of the contraction was reduced to 50% of the control value.

TABLE C

| Test Substance Example No. | Cytoprotective effect on atrial contraction induced by hypoxia. Effective concentration in μmole/liter | Corresponding Force Recovery after Hypoxia in % of the Initial Value of the Contractile Force |
|---|---|---|
| 21 | 3.0 | |
| 26 | 2.8 | |
| 44 | 0.27 | |
| 54 | 1.0 | 80 |
| 55 | 0.55 | 80 |
| 56 | 3.2 | 68 |
| 57 | 2 | 65 |
| 58 | 0.63 | 70 |
| 59 | 1.4 | 65 |
| 60 | 2.7 | 62 |
| 62 | 2.5 | 80 |
| 65 | 3.2 | 78 |
| 66 | 0.91 | 77 |
| 68 | 1.5 | 78 |
| 69 | 2.6 | 70 |
| 70 | 1.48 | 77 |
| 71 | 2.3 | 63 |
| 73 | 3.8 | 68 |
| 76 | 1.6 | 65 |
| 78 | 1.1 | 75 |
| 85 | 2.3 | 76 |
| 86 | 0.85 | 77 |
| 87 | 0.63 | 60 |
| 91 | 1.07 | 64 |
| 93 | 3.2 | 74 |
| 95 | 1.7 | 73 |
| 96 | 1.6 | 65 |
| 97 | 3.2 | 71 |

TABLE C-continued

| Test Substance Example No. | Cytoprotective effect on atrial contraction induced by hypoxia. Effective concentration in μmole/liter | Corresponding Force Recovery after Hypoxia in % of the Initial Value of the Contractile Force |
|---|---|---|
| 99 | 0.85 | 74 |
| 100 | 1.3 | 76 |
| 101 | 0.81 | 78 |
| 103 | 3.2 | 70 |
| 104 | 2.4 | 74 |
| 106 | 1.7 | 70 |
| 109 | 1.5 | 79 |
| 111 | 1 | 75 |
| 113 | 1.55 | 74 |

In in vitro experiments on isolated heart muscle cells the compounds exhibited cytoprotective effects with regard to cytotoxic substances such as veratridine or a combination of oligomycin and deoxyglucose.

Because of their above-described effects the compounds of the formula I are suitable as cardioactive medicaments for large mammals, especially humans, for the treatment of ischaemic conditions such as, for example, in coronary heart disease and its consequences such as, for example, cardiac insufficiency. The doses to be employed may be different individually and of course may vary depending on the condition to be treated, on the substance used and on the form of administration. For example, parenteral formulations generally contain less active substance than oral preparations. In general, however, medicament forms containing from 1 to 200 mg of active substance per individual dose are suitable for administration to large mammals, especially humans.

As medicaments, the compounds of formula I may be present with usual pharmaceutical adjuvants in pharmaceutical formulations such as, for example, tablets, capsules, suppositories or solutions. These pharmaceutical preparations may be prepared by known methods using conventional solid or liquid excipients such as, for example, lactose, starch or talc or liquid paraffins and/or using conventional pharmaceutical adjuvants, for example tablet disintegrants, solubilizers or preservatives.

The following examples are intended to illustrate the invention in more detail without in any way restricting its scope.

The structures of the novel compounds were ascertained by spectroscopic analyses, in particular by analysis of the NMR, mass, IR and/or UV spectra.

EXAMPLE 1

3-{3-[N-(2-(3,4-Dimethoxyphenyl)-ethyl)-N-methylamino] -propyloxy}-5-(3,4-dimethoxyphenyl)-pyrazole.

A) 32 ml of ethyl acetoacetate were added dropwise with ice cooling to 100 ml of 21% strength sodium ethylate solution in ethanol (=solution I). After 20 minutes 75 ml of a solution of 50 g of 3,4-dimethoxybenzoyl chloride in 150 ml of tetrahydrofuran (=solution II) were added dropwise to the reaction mixture. Subsequently further quanities of solutions I and II were added dropwise to the reaction mixture alternately, each at intervals of 20 minutes, until the reaction mixture contained a total of 190 ml of solution I and 176 ml of solution II. After 16 hours the precipitated salts were filtered out, washed with tetrahydrofuran and then suspended in water. The aqueous mixture was acidified to pH 1 with ice cooling and was extracted with methyl tert-butyl ether. The extract was evaporated to dryness, and 45 g of ethyl 2-acetyl-2-(3,4-dimethoxybenzoyl)-acetoacetate were obtained as a yellow oil.

B) 45 g of the product obtained in A) were boiled at reflux in 197 ml of aqueous ethanol with the addition of 0.72 g of sodium acetate. The reaction mixture was subsequently evaporated to dryness three times with the addition of ethanol. The residue was dissolved in dichloromethane and dried with sodium sulfate. The solution was subsequently evaporated to dryness, and 33 g of ethyl 3,4-dimethoxybenzoylacetate were obtained as a yellow oil.

C) 33 g of the product obtained above were placed in 250 ml of ethanol, and 10 ml of hydrazine hydrate were added dropwise to the reaction mixture with ice cooling. The mixture was allowed to stand for 16 hours at room temperature, and then the crystallized reaction product was filtered out, washed with isopropanol and dried. 24 g of 5-(3,4-dimethoxyphenyl)-pyrazolin-3-one were obtained.

D) 29 ml of 1-bromo-3-chloropropane were dissolved in 300 ml of dimethylformamide, and 24 g of potassium carbonate were added to the solution. A solution of 18 g of 2-(3,4-dimethoxyphenyl)-ethyl-N-methylamine in 50 ml of dimethylformamide was added dropwise with stirring to the reaction mixture over the course of 2 hours. Subsequently the reaction mixture was stirred for a further hour. The salts which formed were then filtered out. The filtrate was concentrated at a bath temperature of max. 50° C.; the residue was dissolved in 200 ml of 0.5M citric acid solution, and the solution was extracted with tert-butyl methyl ether in order to remove unreacted bromochloropropane. The aqueous phase was then rendered slightly alkaline by addition of sodium hydrogen carbonate and was extracted several times with ethyl acetate. The combined ethyl acetate extracts were subsequently dried with magnesium sulfate and concentrated. The residue obtained was 21 g of 3-[N-(2-(3,4-dimethoxyphenyl)-ethyl)-N-methylamino]-propylchloride.

E) 17 g of 5-(3,4-dimethoxyphenyl)-pyrazolin-3-one were dissolved in 200 ml of dimethylformamide. 11 g of potassium carbonate were added to the solution and the reaction mixture was heated at 100° C. under a nitrogen atmosphere for 0.5 hours. A solution of 21 g of 3-[N-(2-(3, 4-di-methoxyphenyl)-ethyl)-N-methylamino]-propylchloride in 150 ml of dimethylformamide was then added dropwise. After 2 hours the salts which formed were filtered out, the filtrate was evaporated to dryness, and the residue was dissolved in ethyl acetate. The solution was subsequently washed with 7% strength aqueous sodium hydroxide solution in order to remove unreacted 5-(3,4-dimethoxyphenyl)-pyrazolin-3-one, dried with sodium sulfate and evaporated to dryness. The residue which remained was 35 g of oily crude product. This product was purified by chromatography over finely particulate silica gel under slightly elevated pressure (flash chromatography) using tert-butyl methyl ether/methanol 10:1 as eluent. 22.3 g of the title compound were obtained as an oil. IR spectrum of the base (as film): 1513 $cm^{-1}$, 1260 $cm^{-1}$, 1236 $cm^{-1}$.

To form a salt, 2.6 g of the oily title compound obtained above were dissolved in isopropanol, 3.7 ml of a 2N solution of hydrochloric acid in isopropanol were added to this solution, and the reaction mixture was evaporated to dryness under reduced pressure. The salt which remained as a residue was recrystallized from isopropanol and dried at 80° C. under a high vacuum. 2.1 g of 3-{3-[N-(2-(3,4-dimethoxyphenyl)-ethyl)-N-methylamino]-propyloxy}-5-(3,4-dimethoxyphenyl)-pyrazole hydrochloride were obtained, having a melting point of 189° to 192° C.

EXAMPLE 2

3-{3-[N-(2-(3,4-Dimethoxyphenyl)-ethyl)-N-methylamino]-propyloxy}-5-(3,4-dimethoxyphenyl)-pyrazole 1.31 g of triphenylphosphine were dissolved in 15 ml of tetrahydrofuran. 1.6 ml of a solution of 0.8 ml of ethyl azodicarboxylate in 0.8 ml of toluene were added dropwise to the solution at a temperature of 5° C. After 5 minutes a solution of 1.1 g of 5-(3,4-dimethoxyphenyl)-pyrazolin-3-one in 10 ml of dimethylformamide was added dropwise. After 20 minutes a solution of 1.26 g of 3-[N-(2-(3,4-dimethoxyphenyl)-ethyl)-N-methylamino]-propanol in 10 ml of tetrahydrofuran was added dropwise. The reaction mixture was subsequently stirred at 20° C. for 48 hours. The reaction mixture was then evaporated to dryness. The resulting crude product was purified by flash chromatography in accordance with the method described in Example 1E). 1.14 g of the title compound were obtained as an oily base. This base was converted as described in Example 1E), to the hydrochloride having a melting point of from 189° to 192° C.

EXAMPLE 3

3-{[N-(2-(3,4-Dimethoxyphenyl)-ethyl)-piperid-3-yl]-methoxy}-5-(3,4-dimethoxyphenyl)-pyrazole.

A) A mixture of 5.75 g of 3-(hydroxymethyl)-piperidine, 13.8 ml of triethylamine and 10 g of 2-(3,4-dimethoxyphenyl)-ethyl chloride was heated under reflux for 4 hours. After the reaction mixture had cooled, it was acidified with about 30 ml of aqueous 2N hydrochloric acid solution, and unreacted 2-(3,4-dimethoxyphenyl)-ethyl chloride was separated by extraction with tert-butyl methyl ether. The aqueous phase was then rendered alkaline by addition of sodium hydroxide solution and was extracted with dichloromethane. The organic phase was separated, dried and concentrated. 5.3 g of N-[2-(3,4-dimethoxyphenyl)-ethyl]-3-hydroxymethyl)-piperidine were obtained.

B) 5.3 g of the product obtained above were dissolved in 70 ml of dichloromethane to which 0.1 ml of dimethylformamide had been added, and 5 ml of thionyl chloride were added to the solution. The reaction mixture was stirred at room temperature for 12 hours, concentrated and evaporated to dryness twice with toluene. The residue which remained was dissolved in a mixture of saturated sodium carbonate solution and ethyl acetate. The organic phase was separated, dried with sodium sulfate and evaporated. The residue obtained was 6.6 g of N-[2-(3,4-dimethoxyphenyl)-ethyl]-3-(chloromethyl)-piperidine.

C) 6.6 g of the product obtained above were reacted with 4.4 g of 5-(3,4-dimethoxyphenyl)-pyrazolin-3-one in accordance with the method described in Example 1E). The crude title compound obtained was purified as described in Example 1E). 4.1 g of the title compound were obtained as an oily base.

To form a salt, 4.1 g of the title compound were dissolved in ethanol, and 1.07 g of oxalic acid in ethanol were added to the solution. 3.4 g of 3-{[N-(2-(3,4-dimethoxyphenyl)-ethyl)-piperidin-3-yl]-methoxy}-3,4-dimethoxyphenyl)-pyrazole monohydrogen oxalate were obtained, having a melting point of from 147° to 150° C.

EXAMPLE 4

3-{3-[N-(2-(3-Methylphenyl)-ethyl)-N-methyl-amino]-propyloxy}-2-methyl-5-(2-fluorophenyl)-pyrazole.

A) 32 g of methylhydrazine were added dropwise with ice cooling to a solution of 100 g of ethyl 2-fluorobenzoylacetate in 400 ml of ethanol. The reaction mixture was allowed to stand at room temperature for 2 days in order to complete the reaction. The crystalline precipitate of 2-methyl-5-(2-fluorophenyl)-pyrazolin-3-one was then filtered out.

B) 5 g of the product obtained above were dissolved in 60 ml of dimethylformamide. 0.86 g of sodium hydride (as an 80% strength solution in paraffin) was added to the solution, and the reaction mixture was stirred at 80° C. for 1 hour. It was then cooled to room temperature, 4.1 g of 1-bromo-3-chloropropane were added, and the reaction mixture was stirred at room temperature for 12 hours. The reaction mixture was subsequently concentrated, and the residue was taken up in water and extracted with diethyl ether. The ethereal solution was separated and purified by flash chromatography over silica gel. 4.8 g of 3-(3-chloropropyloxy)-2-methyl-5-(2-fluorophenyl)-pyrazole were obtained.

C) 2.4 g of the product obtained above and 1.5 g of N-methyl-2-(3-methylphenyl)-ethylamine were dissolved in 75 ml of dimethylformamide. 2.5 g of finely ground anhydrous potassium carbonate were added to the solution. The reaction mixture was stirred at a bath temperature of 100° C. for 11 hours. The mixture was subsequently concentrated, the residue was taken up in water, and the reaction product was extracted with ethyl acetate. The organic phase was separated and extracted twice with aqueous 2M citric acid solution. Subsequently the aqueous solution of the product, containing citric acid, was rendered alkaline by addition of sodium carbonate, and the reaction product was extracted with ethyl acetate. The ethyl acetate phase was dried with magnesium sulfate and concentrated. 1.0 g of the title compound was obtained as an oily base. IR spectrum of the base (as film): 1555 cm$^{-1}$, 1508 cm$^{-1}$, 1464 cm$^{-1}$.

To form a salt 0.9 g of the title compound was dissolved in ethanol, an equimolar quantity of L-(+)-tartaric acid was added to the solution, and the mixture was concentrated. 1.25 g of 3-{3-[N-(2-(3-Methylphenyl)-ethyl)-N-methylamino]-propyloxy}-2-methyl-5-(2-fluorophenyl)-pyrazole× 1.1 hydrogen tartrate were obtained as an amorphous solid.

EXAMPLE 5

3-{3-[N-(2-(4-Nitrophenyl)-ethyl)-N-methylamino]-propyloxy}-5-(2-fluorophenyl)-2-methyl-pyrazole A) 260 ml of 1-bromo-3-chloropropane were dissolved in 400 ml of acetone. 230 g of potassium carbonate were added to the solution. A solution of 115 ml of N-methyl-N-benzylamine in 115 ml of acetone was added dropwise to the reaction mixture with stirring at a bath temperature of 40° C., the addition being distributed over a period of 30 minutes. The reaction mixture was subsequently stirred at a temperature of 40° C. for 4 hours. The precipitated salts were then filtered out. The filtrate was concentrated under reduced pressure at a temperature of 40° C. The residue was acidified to a pH of 1 using 16% strength aqueous hydrochloric acid solution and was washed 3 times with tert-butyl methyl ether in order to remove unreacted 1-bromo-3-chloropropane. The aqueous phase was subsequently brought to a pH of 8 by addition of 16% strength sodium hydroxide solution and was extracted repeatedly with ethyl acetate. The combined ethyl acetate phases were dried with magnesium sulfate and concentrated. 71 g of 3-(N-benzyl-N-methylamino)-propyl chloride were obtained.

B) 3.3 g of 2-methyl-5-(2-fluorophenyl)-pyrazolin-3-one were dissolved in 50 ml of 1,3-dimethyl-3,4,5,6-tetrahydro-2(1H)-pyrimidone. 0.55 g of sodium hydride (as an 80 % strength solution in paraffin) was added to this solution and the reaction mixture was stirred at 80° C. for 30 minutes. 3.3 g of 3-(N-benzyl-N-methylamino)-propyl chloride were added to the reaction mixture which was stirred at 80° C. for a further 2 hours. After the reaction mixture had cooled, 10 ml of a 2N solution of hydrochloric acid in isopropanol were added to it, and the mixture was then added dropwise to 2 liters of a 1:3 mixture of acetone and tert-butyl methyl ether. The resulting precipitate was filtered out and dissolved in a mixture of saturated aqueous sodium carbonate solution and ethyl acetate. The organic phase was separated and the aqueous phase was subsequently extracted repeatedly with ethyl acetate. The combined ethyl acetate extracts were dried with sodium sulfate and evaporated. The crude base obtained was purified by chromatography on silica gel. 4.4 g of 3-[3-(N-benzyl-N-methylamino)-propyloxy]-2-methyl-5-(2-fluorophenyl)-pyrazole were obtained.

C) 4.4 g of the product obtained above were dissolved in aqueous methanol. The solution was acidified with hydrochloric acid. Then a catalytic quantity of on palladium on charcoal was added and the reaction mixture was hydrogenated at room temperature with hydrogen at a pressure of 6 bar for 24 hours. Subsequently the catalyst was filtered out, and the filtrate was evaporated under reduced pressure. The residue which remained was dissolved in a mixture of saturated aqueous sodium carbonate solution and ethyl acetate. The organic phase was separated, and the aqueous phase was subsequently extracted repeatedly with ethyl acetate. The combined ethyl acetate phases were dried and evaporated. 3.2 g of 3-[3-(N-methylamino)-propyloxy]-2-methyl-5-(2-fluorophenyl)-pyrazole were obtained.

D) 3.1 g of the product obtained above were dissolved in 30 ml of 1,3-dimethyl-3,4,5,6-tetrahydro-2(1H)-pyrimidone. 3 g of potassium carbonate were added to the solution, and the reaction mixture was stirred at a temperature of 80° C. for 30 minutes. Then 2.5 g of 2-(4-nitrophenyl)-ethyl bromide were added, the reaction mixture was stirred at 50° C. for 5 hours, then a further 0.25 g of 2-(4-nitrophenyl)-ethyl bromide was added, and the mixture was stirred at 80° C. for 13 more hours. Subsequently the reaction mixture was worked up as described in Example 5B). 2.6 g of the title compound were obtained as an oily base. IR spectrum (as film): 1555 cm$^{-1}$, 1515 cm$^{-1}$, 1345 cm$^{-1}$.

The title compound was subsequently converted into its hydrogen tartrate as described in Example 4C). 3.54 g of the monohydrogen tartrate of the title compound were obtained as an amorphous solid.

EXAMPLE 6

3-{3-[N-(3,4-Dimethylbenzyl)-N-methylamino]-2-hydroxypropyloxy}-5-(2-fluorophenyl)-2-methylpyrazole.

A) 78 g of thionyl chloride were added to 50 g of 3,4-dimethylbenzoic acid and the reaction mixture was heated at reflux for 3 hours. The reaction mixture was subsequently concentrated, and the residue was taken up twice in toluene and concentrated again. 53 g of 3,4-dimethylbenzoyl chloride were obtained.

B) 108 ml of a 40 % strength aqueous solution of methylamine were dissolved in 300 ml of tetrahydrofuran. 53 g of 3,4-dimethylbenzoyl chloride were added dropwise to this solution with ice cooling. The reaction mixture was subsequently stirred at room temperature for 1 hour. Then the reaction mixture was concentrated to half its volume under reduced pressure, saturated sodium chloride solution was added, and the mixture was acidified with concentrated hydrochloric acid. The product which then precipitated was filtered out with suction and dried at 40° C. over potassium hydroxide in a drying cabinet. 47 g of N-methyl-3,4-dimethylbenzamide were obtained.

C) 6.4 g of lithium aluminium hydride were placed in 200 ml of tetrahydrofuran and heated to boiling. Over the course of one hour a solution of 25 g of the amide prepared in B) in tetrahydrofuran was added dropwise and the reaction mixture was heated at reflux for a further 3 hours. The reaction mixture was subsequently decomposed with aqueous sodium hydroxide solution in order to remove excess lithium aluminium hydride and was diluted with water and ethyl acetate. The precipitated salts were filtered out, and the organic phase was separated, dried over magnesium sulfate and concentrated. 22.55 g of N-methyl-(3,4-dimethylbenzyl)amine were obtained.

D) 10 g of the product obtained above and 0.2 ml of water were added dropwise at a temperature of 28 to 30° C. to 5.25 ml of epichlorohydrin. The reaction mixture was stirred at about 30° C. for 5 hours. After the reaction mixture had cooled to room temperature, 60% strength aqueous sodium hydroxide solution was added dropwise to it and it was stirred subsequently for a further 40 minutes. In order to work up the reaction mixture, it was poured into 26 ml of water. The oil which separated out was isolated and dried with potassium hydroxide. The aqueous phase was extracted with ethyl acetate, the ethyl acetate extract was dried and concentrated, and the oil which remained as a residue was combined with the major proportion of the product, which had separated out as an oil. A total of 11.3 g of 2-[N-(3,4-dimethylbenzyl)-N-methyl-aminomethyl]-oxirane were obtained.

E) 500 mg of 5-(2-fluorophenyl)-2-methylpyrazol-3-one were stirred with 360 mg of anhydrous potassium carbonate in 10 ml of dimethylformamide at a temperature of 100° C. for 15 minutes. After the reaction mixture had cooled to 60° C., 535 mg of the oxirane obtained in D) were added. The reaction mixture was subsequently stirred at 100° C. for 8 hours. In order to work up the reaction mixture, it was concentrated and the residue was taken up in water and extracted with ethyl acetate. The organic phase was separated and concentrated. The crude product which remained as a residue was purified by flash chromatography. 0.11 g of the title compound was obtained as an oily base. IR spectrum (as film): 1556 cm$^{-1}$, 1462 cm$^{-1}$, 754 cm$^{-1}$.

To form a salt, 320 mg of the title base obtained above were dissolved in a 1:1 mixture of ethanol/ethyl acetate, and an equimolar quantity of fumaric acid was added to the solution. The reaction mixture was concentrated to dryness and the resulting salt was dried at 50° C. 540 mg of 3-{3-[N-(3,4-dimethylbenzyl)-N-methylamino]-2-hydroxypropyloxy}-5-(2-fluorophenyl)-2-methylpyrazole monohydrogen fumarate were obtained as an amorphous solid.

EXAMPLE 7

3-{2-[N-(2-(3,4-Dimethoxyphenyl)-ethyl)-N-methylamino]-1,1-dimethylethoxy}-5-(3,4-dimethoxyphenyl)-pyrazole.

A) 8.8 g of 5-(3,4-dimethoxyphenyl)-pyrazolin-3-one were dissolved in 50 ml of dimethylformamide, and 5.5 g of potassium carbonate were added. The reaction mixture was heated under nitrogen at 100° C. for 0.5 hours. Subsequently 8.9 g of ethyl 2-bromo-2-methylpropionate were added dropwise at 80° C. The mixture was stirred at 80° C. for 1 hour and cooled, and the precipitated salts were filtered out. The filtrate was concentrated in vacuo, and the residue was dissolved in tert-butyl methyl ether. After filtration to remove insoluble fractions, the product was washed with saturated sodium chloride solution and concentrated. 10 g of 3-(2-ethoxycarbonylpropyl-2-oxy)-5-(3,4-dimethoxyphenyl)-pyrazole were obtained as an oil.

B) 10 g of the product obtained above were dissolved in a mixture of 20 ml of 20% strength sodium hydroxide solution and 40 ml of ethanol and the reaction mixture was heated under reflux for 2 hours. After the reaction mixture had been cooled, it was acidifed to a pH of 1 using concentrated hydrochloric acid and extracted repeatedly with tert-butyl methyl ether. The combined extracts were dried with magnesium sulfate and concentrated. 9 g of 3-(2-hydroxycarbonylpropyl-2-oxy)-5-(3,4-dimethoxyphenyl)-pyrazole were obtained.

C) 5 g of the product obtained above were suspended in dichloromethane, 4.5 ml of triethylamine were added at room temperature, the mixture was cooled to −30° C., and 1.28 ml of methanesulfonyl chloride were added. The reaction mixture was stirred at −30° C. for 1 hour, and then a spatula-tipful of pyrrolidinopyridine was added and the mixture was heated to room temperature. After 12 hours it was diluted with dichloromethane. After removing the basic constituents by extraction with a solution of sodium chloride containing citric acid, the organic phase was washed free of acid with concentrated sodium carbonate solution, dried with sodium sulfate and concentrated. 3.7 g of 2,2-dimethyl-6-(3,4-dimethoxyphenyl)-pyrazolo(5,1)oxazole were obtained. Melting point 120° to 130° C.

D) 3.5 g of the product obtained above and 4.2 g of N-methyl-2-(3,4-dimethoxyphenyl)-ethylamine were dissolved in diglyme and heated under nitrogen at 150° C. for 2 hours. After the mixture had been cooled, it was diluted with methyl tert-butyl ether, washed free of base with sodium chloride solution containing citric acid and then washed free of acid with saturated sodium carbonate solution. The organic phase was dried with magnesium sulfate and concentrated by evaporation. 6 g of 3-{2-[N-(2-(3,4-dimethoxyphenyl)-ethyl)-N-methylaminocarbonyl]-propyl-2-oxy}-5-(3,4-dimethoxyphenyl)-pyrazole were obtained.

E) A solution of 6 g of the product obtained above in dry tetrahydrofuran was added dropwise to 20 ml of a boiling 1 molar solution of lithium aluminium hydride in tetrahydrofuran. The reaction mixture was heated at reflux for 2 hours. In order to work up the reaction mixture, 0.57 ml of water, 0.75 ml of 15% strength sodium hydroxide solution and a further 2.5 ml of water were added in succession with ice cooling. The precipitated aluminium hydroxide was filtered out, and the filtrate was concentrated. The residue was dissolved in aqueous 1M citric acid solution. The solution was washed with ethyl acetate. Subsequently the solution, which contained citric acid, was separated and rendered alkaline by addition of aqueous sodium carbonate solution, and the reaction product was extracted with ethyl acetate. The ethyl acetate phase was dried and concentrated by evaporation. 4.1 g of crude product were obtained which was purified by chromatography on silica gel. 2.7 g of the title compound were obtained as an oily base. IR spectrum (as film): 1512 cm$^{-1}$, 1464 cm$^{-1}$, 1261 cm$^{-1}$.

To form a salt, the title compound was subsequently reacted with an equimolar quantity of L-(+)-tartaric acid in accordance with the method described in Example 4C). 3.56 g of 3-{2-[N-(2-(3,4-Dimethoxyphenyl)-ethyl)-N-methylamino]-1,1-dimethylethoxy}-5-(3,4-dimethoxyphenyl)-pyrazole×1.2 hydrogen tartrate were obtained as an amorphous solid.

EXAMPLE 8

3-{6-[N-(2-(3,4-Dimethoxyphenyl)-ethyl)-N-methylamino]-hexyloxy}-5-(3,4-dimethoxyphenyl)-pyrazole.

A) 10 ml of 6-bromohexanoyl chloride were dissolved in a mixture of 100 ml of absolute dichloromethane and 100 ml of absolute toluene. A solution of 13.6 g of N-methyl-N-[2-(3,4-dimethoxyphenyl)-ethyl]-amine and 9.5 ml of triethylamine in 25 ml of absolute toluene was added dropwise to the solution with ice cooling. The reaction mixture was subsequently stirred at room temperature for 12 hours. In order to work it up, the precipitated salts were filtered out and washed with toluene. The filtrate was washed first with 1 molar citric acid solution and then with sodium bicarbonate solution, dried with magnesium sulfate and concentrated. 19.3 g of 5-{N-[2-(3,4-dimethoxyphenyl)-ethyl]-N-methylaminocarbonyl}-pentyl bromide were obtained as an oil.

B) 3.85 g of 5-(3,4-dimethoxyphenyl)-pyrazolin-3-one were dissolved in 50 ml of anhydrous dimethylformamide. 3.15 g of finely ground potassium carbonate were added to the solution, and the reaction mixture was heated under a nitrogen atmosphere to 100° C. with stirring. A solution of 5.6 g of 5-{N-[2-(3,4-dimethoxyphenyl)-ethyl]-N-methylaminocarbonyl}-pentyl bromide in 10 ml of anhydrous dimethyl formamide was slowly added dropwise to the solution, and the reaction mixture was stirred at 100° C. for a further 2 hours. In order to work up the reaction mixture, it was cooled and then the precipitated salts were filtered out and the filtrate was concentrated by evaporation. The oily residue which remained was dissolved in ethyl acetate and washed with 7% strength sodium hydroxide solution in order to remove unreacted 5-(3,4-dimethoxyphenyl)-pyrazolin-3-one. The organic phase was separated, dried with sodium sulfate and concentrated by evaporation. 6.5 g of 3-{5-[N-(2-(3,4-dimethyloxyphenyl)-ethyl)-N-methylaminocarbonyl]-pentyloxy}-5-(3,4-dimethoxyphenyl)-pyrazole were obtained as an oil.

C) 6.5 g of the product obtained above were reduced using lithium aluminium hydride in accordance with the method described in Example 7B). Subsequently the reaction mixture was worked up in accordance with the method described in Example 7E). 2.5 g of the title compound were obtained as an oily base. The IR spectrum (as film) showed bands at 1509 cm$^{-1}$, 1465 cm$^{-1}$, 1261 cm$^{-1}$.

The title compound was subsequently reacted in accordance with the method described in Example 4C) with an equimolar quantity of L-(+)-tartaric acid to form a salt. 3.25 g of 3-{6-[N-(2-(3,4-dimethoxyphenyl)-ethyl)-N-methylamino]-hexyloxy}-5-(3,4-dimethoxyphenyl)-pyrazole×1.1-hydrogen tartrate were obtained as an amorphous solid.

EXAMPLE 9

3-{2-[N-(2-(4-Chlorophenyl)-ethyl)-N-methylamino]-ethyloxy}-5-(4-hydroxyphenyl)-2-methylpyrazole.

1.8 g of 3-(2-[N-(2-(4-chlorophenyl)-ethyl)-N-methylamino]-ethyloxy}-5-(-4-methoxyphenyl)-2-methylpyrazole (see Example 24) were dissolved in 100 ml of dichloromethane. 10 ml of a 1 molar solution of boron tribromide in dichloromethane were added to the solution. The reaction mixture was allowed to stand for 12 hours and then placed in water and extracted with dichloromethane. The aqueous phase was separated, rendered alkaline and extracted three times with a mixture of dichloromethane and methanol, and the combined organic phases were dried and concentrated. The crude title compound obtained as an oil was purified by chromatography on silica gel using dichloromethane/methanol. The purified title compound was reacted in accordance with the method described in Example 4C) with an equimolar quantity of L-(+)-tartaric acid to form a salt, and the resulting salt was crystallized from a mixture of diethyl ether and isopropanol. 1.15 g of 3-{2-[N-(2-(4-chlorophenyl)-ethyl)-N-methylamino]-ethyloxy}-5-(4-hydroxyphenyl)-2-methylpyrazole x 1.3 hydrogen tartrate were obtained having a melting point of 90° to 91° C.

EXAMPLE 10

3-{2-[N-(2-(4-Chlorophenyl)-ethyl)-N-methylamino]-ethyloxy}-5-(4-acetoxyphenyl)-2-methylpyrazole.

100 mg of 3-{2-[N-(2-(4-chlorophenyl)-ethyl)-N-methylamino]-ethyloxy}-5-(4-hydroxyphenyl)-2-methylpyrazole (preparation see Example 9) were dissolved in 2 ml of dichloromethane. 0.15 ml of pyridine and 1 ml of acetic anhydride were added to the solution and the reaction mixture was stirred at room temperature for 24 hours. The reaction mixture was subsequently evaporated under reduced pressure, and the residue was taken up in aqueous sodium bicarbonate solution and extracted with dichloromethane. The organic phase was separated, dried and concentrated. The crude title compound which remained as a residue was taken up in tert-butyl methyl ether. To form a salt, a 2N solution of hydrochloric acid in isopropanol was added. The precipitated salt was separated. 80 mg of the hydrochloride of the title compound were obtained having a melting point of from 160° to 175° C.

EXAMPLE 11

3-{3-[N-(2-(3,4-Dimethoxyphenyl)-ethyl)-amino]-propyloxy}-2-benzyl-5-(3,4-dimethoxyphenyl)-pyrazole.

A) 6.6 g of ethyl 3,4-dimethoxybenzoylacetate were suspended in ethanol, and 3.5 g of benzylhydrazine were added dropwise with ice cooling over the course of 1.5 hours. The reaction mixture was stirred at room temperature for 12 hours. Then the precipitated product was filtered out and washed first with ethanol and then with tert-butyl methyl ether. 4.36 g of 5-(3,4-dimethoxyphenyl)-2-benzylpyrazolin-3-one were obtained. Melting point: 164°–166° C.

B) 5.5 g of the above product were dissolved in 50 ml of dimethylformamide. 0.5 g of sodium hydride was added to the solution, and the mixture was stirred under a nitrogen atmosphere at 80° C. for 0.5 hour. Then 1.97 ml of 1-bromo-3-chloropropane were added dropwise at room temperature and the reaction mixture was stirred for 14 hours. The reaction mixture was then concentrated by evaporation under reduced pressure and taken up in tert-butyl methyl ether and the insoluble residue was filtered out. The filtrate was concentrated and purified by chromatography over finely divided silica gel under slightly elevated pressure (=flash chromatography). 7 g of 3-(3-chloropropyloxy)-5-(3,4-dimethoxyphenyl)-2-benzylpyrazole were obtained.

C) 6 g of the product obtained above and 7 g of homoveratrylamine were dissolved in 20 ml of dimethylformamide, 10 ml of triethylamine were added, and the mixture was heated at 120° C. for 4 hours. The reaction mixture was concentrated by evaporation, and the residue was taken up in ethyl acetate and extracted with 2M citric acid. Subsequently the aqueous solution, containing citric acid, of the product was rendered alkaline by addition of sodium hydrogen carbonate, and the reaction product was extracted with ethyl acetate. The extract was purified by chromatography over finely divided silica gel under slightly elevated pressure (=flash chromatography). 4.9 g of 3-{3-[N-(2-(3,4-dimethoxyphenyl)-ethyl)-amino]-propyloxy}-2-benzyl-5-(3,4-dimethoxyphenyl)-pyrazole were obtained.

The IR spectrum of the base (as film) showed bands at 1524 cm$^{-1}$, 1260 cm$^{-1}$, 1236 cm$^{-1}$.

EXAMPLE 12

3-{3-[N-(2-(3,4-Dimethoxyphenyl)-ethyl)-amino]-propyloxy}-5-(3,4-dimethoxyphenyl)-pyrazole.

4.9 g of 3-{3-[N-(2-(3,4-dimethoxyphenyl)-ethyl)-amino]-propyloxy}-2-benzyl-5-(3,4-dimethoxyphenyl)-pyrazole were dissolved in glacial acetic acid, 0.5 g of palladium on charcoal was added, and the reaction mixture was hydrogenated at 80 bar hydrogen pressure and at 80° C. for 24 hours. After removal of the catalyst by filtration, the reaction mixture was concentrated by evaporation and rendered alkaline (pH=10) with sodium hydroxide solution, and the product was extracted with ethyl acetate. The organic phase was separated, concentrated and purified by flash chromatography over silica gel. 1.1 g of 3-{3-[N-(2-(3,4-dimethoxyphenyl)-ethyl)-amino]-propyloxy}-5-(3,4-dimethoxyphenyl)-pyrazole were obtained. The IR spectrum of the base (as film) showed bands at 1511 cm$^{-1}$, 1465 cm$^{-1}$, 1262 cm$^{-1}$.

To form a salt, 1.1 g of the title compound were dissolved in ethanol, an equimolar quantity of L-(+)-tartaric acid was added to the solution, and the mixture was concentrated. 1.46 g of 3-{3-[N-(2-(3,4-Dimethoxyphenyl)-ethyl)-amino]-propyloxy}-5-(3,4-dimethoxyphenyl)-pyrazole monohydrogen tartrate were obtained as an amorphous solid.

EXAMPLE 13

3-{3-[N-(2-(3,4-Dimethoxyphenyl)-ethyl)-N-methylamino]-propyloxy}-5-(3,4-dimethoxyphenyl)-2-benzylpyrazole.

A) 5 g of 5-(3,4-dimethoxyphenyl)-pyrazolin-3-one, prepared according to Example 1C, were suspended in 100 ml of toluene. First 3 ml of collidine and subsequently 3.6 ml of benzyl bromide were added dropwise to the suspension. After heating for 6 hours under reflux, the reaction mixture was cooled, and the precipitated crystals were filtered out and washed with isopropanol. The crystals obtained were dissolved in dichloromethane and washed with 2M citric acid. The organic phase was dried with magnesium sulfate and concentrated. For purification the residue was recrystallized from isopropanol. 4 g of 5-(3,4-dimethoxyphenyl)-2-benzyl-pyrazolin-3-one were obtained having a melting point of 165° C.

B) 62 g of the product obtained above were dissolved in 500 ml of dimethylformamide. 31 g of potassium carbonate were added to the solution and the reaction mixture was heated under nitrogen at 100° C. for 0.5 hours. Following the dropwise addition of a solution of 56 g of 3-[N-(2-(3,4-dimethoxyphenyl)-ethyl)-N-methylamino]-propyl chloride in 70 ml of dimethylformamide, the reaction mixture was heated at 100° C. for a further 4 hours. The precipitated salts were filtered out, and the filtrate was concentrated to dryness. The residue was taken up in 350 ml of 0.75N hydrochloric acid and extracted with ethyl acetate. The aqueous acidic phase was rendered alkaline by addition of aqueous sodium hydroxide solution and was extracted with ethyl acetate. The crude product obtained after drying and concentration by evaporation of the organic phase was purified by flash chromatography. 68 g of 3-{3-[N-(2-(3,4-Dimethoxyphenyl)ethyl) -N-methylamino]-propyloxy}-5-(3,4-dimethoxyphenyl)-2-benzyl-pyrazole were obtained. The IR spectrum of the base (as film) showed bands at 1524 cm$^{-1}$, 1260 cm$^{-1}$, 1236 cm$^{-1}$.

1.63 g of oxalic acid dihydrate dissolved in 20 ml of acetone were added dropwise to 7.1 g of the base, dissolved in 100 ml of acetone. The precipitated crystals were filtered out and dried. 7.7 g of the hydrogen oxalate of 3-{3-[N-(2-(3,4-Dimethoxyphenyl)-ethyl)-N-methylamino]-propyloxy}-5-(3,4-dimethoxyphenyl)-2-benzyl-pyrazole were obtained having a melting point of 135° to 137° C.

EXAMPLE 14

3-{3-[N-(2-(3,4-Dimethoxyphenyl)-ethyl)-N-methylamino)-propyloxy}-5-(3,4-dimethoxyphenyl)-pyrazole.

A) 2 g of 3-{3-[N-(2-(3,4-Dimethoxyphenyl)-ethyl)-N-methylamino]-propyloxy}-5-(3,4-dimethoxyphenyl)-2-benzyl-pyrazole prepared according to Example 13 were dissolved in 10 ml of methanol and added to 2 g of palladium black under nitrogen. 5.5 ml of 98% strength formic acid were added to the solution, which was stirred under nitrogen. After the mixture had been stirred for 3 hours under nitrogen the catalyst was filtered out, and the filtrate was concentrated by evaporation. The oily residue was taken up in saturated sodium carbonate solution and extracted repeatedly with ethyl acetate. The combined organic phases were dried with sodium sulfate and concentrated by evaporation. 1.6 g of 3-{3-[N-(2-(3,4-Dimethoxyphenyl)-ethyl)-N-methylamino]-propyloxy}-5-(3,4-dimethoxyphenyl)-pyrazole were obtained as an oily base. This base was converted analogously to Example 1E) into the hydrochloride having a melting point of 189° to 192° C.

Following the methods described in the foregoing examples it was also possible to prepare the compounds of formula I listed in the following table. The IR bands given in the table in cm$^{-1}$ are the characteristic bands of the IR spectra of the respective free bases (measured as a film unless otherwise stated).

| Example No. | $R^2$ | $R^3$ | $R^4$ | $R^5$ | $R^6$ | $R^7$ | n | A | Remarks mp. in °C.; IR bands in cm$^{-1}$ |
|---|---|---|---|---|---|---|---|---|---|
| 15 | 3-CH$_3$O | 4-CH$_3$O | H | 2-CH$_3$ | 3-CH$_3$O | 4-CH$_3$O | 1 | —NH—(CH$_2$)$_3$— | 1.1 TA; am; base; oily; IR: 1513, 1262, 1235 |
| 16 | 3-Cl | 4-Cl | H | 2-CH$_3$ | 3-CH$_3$O | 4-CH$_3$O | 1 | —NH—(CH$_2$)$_3$— | 1.1 TA; am; base; oily; IR: 1553, 1523, 1257 |
| 17 | 3-CH$_3$O | H | H | 2-CH$_3$ | 3-Cl | 4-Cl | 2 | —NH—(CH$_2$)$_3$— | 1.3 TA; am; base; oily; IR: 1564, 1550, 1498 |
| 18 | 3-CH$_3$O | 4-CH$_3$O | H | H | 4-NO$_2$ | H | 2 | —N(CH$_3$)—(CH$_2$)$_3$— | 0.5 FU; am; base; oily; IR: 1512, 1342, 1261 |
| 19 | 3-CH$_3$O | 4-CH$_3$O | H | H | 3-Cl | 4-Cl | 2 | —N(CH$_3$)—(CH$_2$)$_2$— | 1 FU; am; base; oily; IR: 1511, 1462, 1142 |
| 20 | 4-CH$_3$ | H | H | 2-CH$_3$ | 3-CH$_3$O | 4-CH$_3$O | 1 | —NH—(CH$_2$)$_3$— | 1 TA; am; base; oily; IR: 1553, 1524, 1258 |
| 21 | H | H | H | 2-CH$_3$ | 2-F | H | 2 | —N(CH$_3$)—(CH$_2$)$_3$— | 0.9 TA; am; base, oily; |

-continued

| Example No. | R² | R³ | R⁴ | R⁵ | R⁶ | R⁷ | n | A | Remarks mp. in °C.; IR bands in cm⁻¹ |
|---|---|---|---|---|---|---|---|---|---|
| 22 | 3-CH₃O | 4-CH₃O | H | 2-CH₃ | 3-CH₃ | 4-CH₃ | 1 | —N(CH₃)—(CH₂)₃— | 1.1 TA; am; base; oily; IR: 1553, 1463, 752 |
| 23 | 3-Cl | 4-Cl | H | 2-CH₃ | 3,4-O—CH₂—O— | | 1 | —N—(CH₃)—(CH₂)₂— | 1 TA; am; base; oily; IR: 1554, 1513, 1262 |
| 24 | 4-Cl | H | H | 2-CH₃ | 4-CH₃O | H | 2 | —N—(CH₃)—(CH₂)₂— | 1.1 TA; m.p. 94° C. IR: 1560, 1460, 1240 |
| 25 | H | H | H | 1-CH₃ | 2-F | H | 2 | —N(CH₃)—(CH₂)₃— | 0.9 TA; am; base; oily; IR: 1508, 1458, 759 |
| 26 | H | H | H | 2-CH₃ | 2-F | H | 5 | —N(CH₃)—(CH₂)₃— | 1 OX; 142; base; oily; IR: 1555, 1509, 1464 |
| 27 | 3-CH₃O | 4-CH₃O | H | H | 3-CH₃O | 4-CH₃O | 2 | —N(CH₃)—(CH₂)₄— | 2.4 HCl; m.p. 158–160° C. |
| 28 | 3,4-O—CH₂—O— | | H | 2-CH₃ | 2-F | H | 1 | —N(CH₃)—(CH₂)₂— | 1.1 TA; am; base; oily; IR: 1554; 1488; 1039 |
| 29 | 2-F | H | H | 2-CH₃ | 2-F | H | 2 | —N(CH₃)—(CH₂)₂— | 1 OX; mp 152–53; base; oily; IR: 1555; 1492; 1463 |
| 30 | 4-NO₂ | H | H | 2-CH₃ | 3-CH₃O | 4-CH₃O | 2 | —N(CH₃)—(CH₂)₂— | 1 FU; am; base; oily; IR: 1517, 1346, 1258 |
| 31 | 3-CH₃O | 4-CH₃O | CH₃(CH₂)₂ | H | H | H | 2 | —N(CH₃)—(CH₂)₃— | 1 OX; m.p. 169 |
| 32 | 3-CH₃O | 4-CH₃O | H | H | 3-CH₃O | 4-CH₃O | 2 | —N(CH₃)—(CH₂)₈— | 0.9 OX; m.p. 92; base; oily; IR: 1513, 1260, 1028 |
| 33 | 4-NO₂ | H | H | H | 3-CH₃O | 4-CH₃O | 2 | —N—(CH₃)—(CH₂)₂— | 1 OX; m.p. 140–41° C. |
| 34 | 3-CH₃O | 4-CH₃O | H | H | 4-CF₃ | H | 2 | —N(CH₃)—(CH₂)₃— | 1 FU; am; base; oily; IR: 1512, 1465, 1326 |
| 35 | 3-CH₃O | H | H | 2-CH₃ | 4-CH₃ | H | 2 | —N(CH₃)—(CH₂)₃— | 1.1 TA; am; base; oily; IR: 1584, 1554, 1529 |
| 36 | 3-CH₃O | H | CH₃ | 1-CH₃ | 4-Cl | H | 2 | —N(CH₃)—(CH₂)₃— | 1 TA; am; base; oily; IR: 1508, 1466, 1260 |
| 37 | 3-CH₃O | 4-CH₃O | H | 1-CH₃ | H | H | 2 | —N(CH₃)—(CH₂)₃— | 1 FU; am; base; oily; IR: 1512, 1463, 1263 |
| 38 | 3-CH₃O | 4-CH₃O | H | 2-CH₃ | H | H | 2 | —N(CH₃)—(CH₂)₃— | 1.1 FU; am; base; oily; IR: 1554, 1513, 1263 |
| 39 | 3-CH₃COO | H | H | 2-CH₃ | 4-CH₃ | H | 2 | —N(CH₃)—(CH₂)₃— | base; oily; IR: 1765, 1554, 1208 |
| 40 | 3-OH | H | H | 2-CH₃ | 4-CH₃ | H | 2 | —N(CH₃)—(CH₂)₃— | 2.1 HCl; m.p. 165–70° C. |
| 41 | 4-CF₃ | H | H | H | 4-NO₂ | H | 2 | —N(CH₃)—(CH₂)₃— | 1 OX; m.p. 89° C.; base; oily; IR: 1670, 1514, 1327 |
| 42 | H | H | H | H | H | H | 2 | —N(CH₃)—(CH₂)₃— | 1 OX; m.p. 157; IR: 1507, 1465, 1374 |
| 43 | H | H | H | H | 4-NO₂ | H | 2 | —N(CH₃)—(CH₂)₂— | 0.9 OX; m.p. 160–61° C.; IR: 1604, 1517, 1343 |
| 44 | 3-CH₃O | 4-CH₃O | H | H | H | H | 2 | —N(CH₃)—(CH₂)₃— | 1 TA; am; base, m.p. 95° C.; IR: 1513, 1463, 1265 |
| 45 | 4-Cl | H | H | H | 4-F | H | 2 | —N(CH₃)—(CH₂)₃— | 1 OX; m.p. 103° C. |
| 46 | 3-CH₃O | 4-CH₃O | CH₃ | H | 4-Cl | H | 2 | —N(CH₃)—(CH₂)₃— | 1.2 TA; am; base; oily; IR: 1501, 1463, 1262 |
| 47 | 3-CH₃O | 4-CH₃O | H | H | 3-CH₃O | 4-CH₃O | 2 | —N(CH₃)—(CH₂)₂— | 1.1 TA; am; base; oily; IR: 1512, 1260, 1027 |
| 48 | H | H | H | H | 4-F | H | 2 | —N(CH₃)—(CH₂)₃— | 1 OX; m.p. 149° C. |
| 49 | H | H | H | H | 3-CH₃O | 4-CH₃O | 2 | —N(CH₃)—(CH₂)₃— | 1.2 FU; am; base; oily; IR: 1518, 1464, 1262 |
| 50 | 4-CF₃ | H | H | H | 4-F | H | 2 | —N(CH₃)—(CH₂)₃— | 1 OX; m.p. 90° C. |
| 51 | 3-CH₃O | 4-CH₃O | H | H | 3-CH₃O | 4-OH | 2 | —N(CH₃)—(CH₂)₃— | 1.1 TA; am; IR: 1517, 1466, 1265 |
| 52 | 3-CH₃O | 4-CH₃O | H | H | 3-CH₃O | 4-CH₃O | 2 | —NH—(CH₂)₃— | 1 TA; am; IR: 1511, 1465, 1262 |
| 53 | 3-CH₃O | 4-OH | H | H | 3-CH₃O | 4-CH₃O | 2 | —N(CH₃)—(CH₂)₃— | 1 TA; am; IR: 1259, 1374, 1517, 1595 |

EXAMPLE 54

3-{3-[N-(2-(3,4-Dimethoxyphenyl)-ethyl)-N-methylamino]-propyloxy}-5-phenyl-1,2,4-thiadiazole.

A) 38.7 g of thiobenzamide were suspended in 380 ml xylol. The suspension was cooled to 5° C. and then 24.8 ml of oxalylchloride was added dropwise, keeping the temperature at 4° to 6° C. After 30 minutes stirring at 40° C. followed by 90 minutes stirring at 90° C., 58 ml of azidotrimethylsilane was added dropwise in such fashion that the temperature did not exceed 110° C. Then the mixture was stirred for another 2 hours at 100° C. and then cooled to room temperature. Then 200 ml of isopropanol was added for workup and the reaction mixture was allowed to crystallize for several hours. The crystal formed was drawn off, washed with isopropanol, and dried. 35 g of 5-phenyl-1,2,4-thiadiazole-3-ole was obtained as a yellow solid.

B) 20.6 g of the substance obtained above were dissolved in 275 ml dimethylformamide. 14.3 g potassium tert-butylate were added to the solution and the reaction mixture was then heated at 80° C. and stirred for 2 hours at this temperature. Then it was cooled to 60° C. and 12.6 ml of 1-bromo-3-chloropropane were added. Addition was conducted in such fashion that the temperature of 60° C. was not exceeded. Then the solution was stirred for another 2 hours at 60° C. Then the reaction mixture was poured into ice water for workup and extracted twice with methyl-tert-butyl ether. The organic phases were washed with water and concentrated by evaporation. The oil which remained as a residue was then stirred with 100 ml of a 1:1 mixture of petroleum ether/methyl-tert-butyl ether and 20 g of silica gel. After filtering off the silica gel, the solution was concentrated by evaporation. 28 g of 3-(5-phenyl-1,2,4-thiadiazole-3-yloxy)-propyl chloride were obtained as the oil.

C) 28 g of the substance obtained above were reacted with 21.4 g of N-methylhomoveratrylamine and the mixture was heated at 100° C. After stirring for 15 minutes, 15.2 ml of triethylamine and 15.2 ml of dimethylformamide were added and the reaction mixture was stirred for another 2 hours at 120° C. For workup, the reaction mixture was cooled and reacted with 100 ml of a 9:1 mixture of ethyl acetate/methanol and 100 ml of water and stirred for 30 minutes at room temperature. Then the organic phase was separated, the aqueous phase was suspended in 50 ml of a 9:1 mixture of ethyl acetate/methanol, the organic phases were combined, dried, and concentrated by evaporation to dryness. 33 g of the title compound were obtained as an oil.

In order to form a salt, the oily title compound was dissolved in 200 ml isopropanol and hydrochloric acid gas was introduced into the solution while cooling with ice. The crystal obtained was filtered off and dried. 23.6 g of 3-{3-[N-(2-(3,4-dimethoxyphenyl)-ethyl)-N-methylamino]-propyloxy}-5-phenyl-1,2,4-thiadiazole hydrochloride were obtained as a colorless crystal with a melting point of 156° to 158° C.

EXAMPLE 55

3-{3-[N-(2-(3,4-Dimethoxyphenyl)-ethyl)-N-methylamino]-propyloxy)-5-phenyl-1,2,4-oxadiazole.

A) 26 g of benzoylisocyanate were reacted with 40 g of azidotrimethylsilane and the reaction mixture was refluxed for 7 hours while stirring, then allowed to stand for several hours at room temperature and refluxed for another 7 hours. For workup, the reaction mixture was concentrated by evaporation to dryness and the remaining residue was dissolved in 30 ml of methanol. Crystallization occurred spontaneously. The crystals that settled out were drawn off and dried. 20.2 g of 5-phenyl-1,2,4-oxadiazole-3-ole were obtained as a colorless solid.

B) 1.6 g of the product obtained above were dissolved in 16 ml of dimethylformamide. 0.5 g of sodium hydride were added to the solution batchwise and the reaction mixture was heated at 80° C. and stirred for 30 minutes. Then 2 ml of 1-bromo-3-chloropropane were added dropwise and the mixture stirred for another 30 minutes at 80° C. For workup, the reaction mixture was then cooled to room temperature, mixed with a little water, and suspended in ethyl acetate. The combined organic phases were dried over sodium sulfate and then concentrated by evaporating to dryness. The oil that remained as a residue was purified by medium pressure chromatography on fine-grained silica gel (Lichroprep Si 60®) at a pressure of 20 bars using 9:1 cyclohexane/ethyl acetate as the eluent. 1 g of 3-(5-phenyl-1,2,4-oxadiazole-3-yloxy)-propyl chloride were obtained as an oil.

C) 1 g of the product obtained above was reacted with 1.5 g of N-methylhomoveratrylamine and the reaction mixture was heated for 1 hour at 130° C. and for another 30 minutes at 140° C. For workup, the reaction mixture was cooled to room temperature, mixed with a small amount of water, and separated out by shaking with ethyl acetate. The organic phases were combined, dried over sodium sulfate, and concentrated by evaporation to dryness. The resultant crude oily title compound was purified by medium pressure chromatography on fine-grained silica gel (Lichroprep Si 60®) at a pressure of 12 bars using 99:1 ethyl acetate/methanol as the eluent. 1.07 g of the title compound were obtained as an oil.

In order to form a salt, the oily title compound was dissolved in methanol and the solution was adjusted to pH 1 by adding hydrochloric acid gas. Then diethylether was added until the solution became cloudy and the mixture was allowed to stand until it crystallized. The crystals that settled out were drawn off and dried. 1 g of 3-{3-[N-(2-(3,4-dimethoxyphenyl)-ethyl)-N-methylamino]-propyloxy}-5-phenyl-1,2,4-oxadiazole hydrochloride were obtained as a colorless solid with a melting point of 160° to 162° C.

EXAMPLE 56

3-{3-[N-(2-(3,4-Dimethoxyphenyl)-ethyl)-N-methylamino]-2-hydroxypropyloxy}-5-phenyl-1,2,4-thiadiazole.

A) 5 g of 5-phenyl-1,2,4-thiadiazole-3-ole (for preparation see Example 54A) were dissolved in 100 ml of dimethylformamide. The solution was reacted batchwise with 1 g of sodium hydride and heated at 60° C. Then a solution of 2.4 ml epichlorohydrin in 10 ml of dimethylformamide was added dropwise and the reaction mixture was stirred for 3 hours at 80° C. For workup, the reaction mixture was cooled to room temperature, poured into water, and extracted twice with ethyl acetate. The organic phase was separated, dried over sodium sulfate, and concentrated by evaporating to dryness. The oil obtained as the residue was purified by chromatography over fine-grained silica gel at a slightly elevated temperature (flash chromatography) using 1:4 methyl-tert-butyl ether/petroleum ether as the eluent. 4 g of 2-(5-phenyl-1,2,4-thiadiazole-3-yloxymethyl)-oxiran were obtained.

B) 3 g of the product obtained above were dissolved in 30 ml of ethanol. 2 g of N-methylhomoveratrylamine and 0.2 ml of pyridine were added to the solution and the reaction mixture was stirred for 2 hours at 80° C. For workup, the reaction mixture was poured into water, extracted twice with dichloromethane, the organic phases were purified, dried, and then concentrated. The crude oily title compound that remained as a residue was purified by chromatography over fine-grained silica gel at a slightly elevated pressure (flash chromatography) using 20:1 ethyl acetate/methanol as the eluent. 7 g of the title compound were obtained as an oil.

In order to form a salt, the oily title compound was dissolved in isopropanol and the solution was saturated with hydrochloric acid gas. The crystal that settled out was drawn off and dried. 5.9 g of 3-{3-[N-(2-(3,4-dimethoxyphenyl)-ethyl)-N-methylamino]-2-hydroxypropyloxy}-5-phenyl-1,2,4-thiadiazole hydrochloride were obtained as a colorless solid with a melting point of 143° C.

EXAMPLE 57

3-{3-[N-(2-(3,4-Methylenedioxyphenyl)-ethyl)-N-methylamino]-propyloxy}-5-phenyl-1,2,4-thiadiazole.

A) 25 g of methylenedioxyphenylacetic acid were mixed with 25 ml of thionyl chloride and the reaction mixture was stirred for 2 hours at 80° C. Then the excess thionyl chloride was distilled off and the residue was taken up twice in toluene and concentrated again. 25 g of crude 3,4-methylenedioxyphenylacetic acid chloride was obtained as a yellow oil.

B) A solution of 25 g of the acid chloride obtained above in 50 ml tetrahydrofuran was added dropwise with ice cooling to a mixture of 100 ml of a 40% aqueous methyl amine solution and 200 ml of tetrahydrofuran. After the addition process was complete, the reaction mixture was stirred for another 2 hours at room temperature and then concentrated to 10% of its original volume. The remaining residue was extracted three times with ethyl acetate. The combined ethyl acetate extracts were concentrated and the residue was added to methyl-tert-butyl ether. After a time, crystallization occurred. The crystals were drawn off, washed, and dried. 17 g of N-methyl-3,4-methylenedioxyphenylacetic acid amide were obtained.

C) 17 g of sodium tetrahydridoborate were added batchwise to a solution of 17 g of the product obtained above in 300 ml of tetrahydrofuran. Then the reaction mixture was stirred for 20 minutes after which 26 ml of glacial acetic acid were added dropwise and the mixture was stirred for another 3 hours at 80° C. For workup, the reaction mixture was cooled to room temperature, poured into water, and rendered alkaline to pH 1 with 20% hydrochloric acid solution. The mixture was stirred for 30 minutes and then rendered alkaline by adding 20% aqueous sodium hydroxide solution and extracted three times with dichloromethane. The organic phases were combined, dried, and concentrated. 13 g of N-[2-(3,4-methylenedioxyphenyl)-ethyl]-N-methylamine were obtained as an oil.

D) 4.5 g of the product obtained above were reacted with 6 g of 3-(5-phenyl-1,2,4-thiadiazole-3-yloxy)-propyl chloride (for preparation, see Example 54B)) using the method described in Example 54C). The crude oily title compound obtained was purified by chromatography over fine-grained silica gel at slightly elevated pressure (flash chromatography) using 1:1 ethyl acetate/cyclohexane as the eluent. 5 g of the title compound were obtained as an oil.

In order to form a salt, the oily title compound was dissolved in isopropanol and the solution was saturated with hydrochloric acid gas. The crystal that settled out was drawn off and dried. 2.71 g of 3-{3-[N-(2-(3,4-methylenedioxyphenyl)-ethyl) -N-methylamino]-propyloxy}-5-phenyl-1,2,4-thiadiazole hydrochloride were obtained as a colorless solid with a melting point of 153° C.

EXAMPLE 58

3-{3-[N-(2-(3,4-Dimethoxyphenyl)-ethyl)-N-methylamino]-propyloxy}-5-phenyl-isoxazole.

A) At 0° C., 91 g of bromine were added to a solution of 100 g of trans-ethylcinnamate in 500 ml of dichloromethane so slowly over a period of 7 hours, dropwise, that large bromine concentrations were avoided. The reaction mixture was allowed to stand for several hours at room temperature, then another 2 ml of bromine were added slowly and the reaction mixture was stirred for another 3 hours at room temperature. Then it was concentrated under reduced pressure. 193 g of 2,3-dibromo-3-phenyl-propionic acid ethyl ester were obtained.

B) 164.5 g of the product obtained above, 46.6 g of imidazole, and 339 ml of triethylamine were dissolved in 2 l of toluene and the solution was stirred for several hours at 100° C. Then the salts that settled out were filtered off, the organic phase was washed with saturated aqueous sodium chloride solution, dried over magnesium sulfate, and concentrated. The residue obtained was crystallized out of diethyl ether. 81.2 g of 3-(imidazole-1-yl)-ethylcinnamate were obtained.

C) 72 g of hydroxyl ammonium chloride and 550 g of a 30% sodium methylate solution were dissolved in 2.5 l of methanol and the solution was refluxed for 1 hour. Then 82 g of 3-(imidazole-1-yl)-ethylcinnamate were added and the reaction mixture was refluxed for another 3 hours. Next the reaction mixture was cooled and a pH value of 1 was set by adding 3 n hydrochloric acid solution. The reaction product was extracted with dichloromethane, the organic phase was dried with magnesium sulfate, and concentrated. During concentration, 30.3 g of 3-hydroxy-5-phenyl-isoxazole crystallized out.

D) 29 ml of 1-bromo-3-chloropropane were dissolved in 300 ml of dimethylformamide and 24 g of potassium carbonate were added to the solution. A solution of 18 g N-[2-(3,4-dimethoxyphenyl)-ethyl]-N-methylamine in 50 ml of dimethylformamide were added to the reaction mixture with stirring, dropwise within 2 hours. Then the reaction mixture was stirred for another hour. Then the salts formed were filtered off. The filtrate was concentrated at a maximum bath temperature of 50° C. The residue was dissolved in 200 ml of 0.5 m citric acid solution and the solution was extracted to remove unreacted bromochloropropane with methyl-tert-butyl ether. The aqueous phase was then made slightly alkaline by adding sodium hydrogen carbonate and extracted several times with ethyl acetate. Then the combined ethyl acetate extracts were dried with magnesium sulfate and concentrated. 21 g of 3-[N-(2-(3,4-dimethoxyphenyl)-ethyl)-N-methylamino]-propyl chloride were obtained as the residue.

E) 3.5 g of 3-hydroxy-5-phenyl-isoxazole were dissolved in 100 ml of dimethylformamide. The solution was reacted with 3 g of finely powdered potassium carbonate and the reaction mixture was heated for 15 minutes at 100° C. in a nitrogen atmosphere. Then 5.8 g of 3-[N-(2-(3,4-dimethoxyphenyl)-ethyl)-N-methylamino]-propyl chloride were added batchwise. The reaction mixture was stirred for 4 hours at 100° C., after which the salts that formed were filtered off, the filtrate was concentrated to dryness, and the residue dissolved in methyl-tert-butyl ether. The solution was then washed with aqueous sodium carbonate solution, dried with magnesium sulfate, and concentrated to dryness. The remaining crude oily title compound that was left as a residue was purified by flash chromatography using ethyl acetate as the eluent. 4.75 g of the title compound were obtained.

In order to form a salt, the oily title compound obtained above was dissolved in acetone and an ethereal hydrochloric acid solution was added dropwise to the solution. The mixture was allowed to stand for several hours at 5° C. and the crystal that formed was drawn off and dried. 4.6 g of 3-{3-[N-(2-(3,4-dimethoxyphenyl)-ethyl)-N-methylamino]-propyloxy}-5-phenyl-isoxazole hydrochloride with a melting point of 156° C. were obtained.

EXAMPLE 59

3-{3-[N-(2-(4-(Methylsulfonylamino)-phenyl)-ethyl)-N-methylamino]-propyloxy}-5-phenyl-1,2,4-thiadiazole.

A) 30 ml of methanesulfonyl chloride were added dropwise with ice cooling to a solution of 25 g of 2-(4-aminophenyl)-ethanol in 200 ml pyridine. After addition was complete, the solution was stirred for 6 hours at room temperature. Then the pyridine was drawn off in a rotary evaporator and the remaining oily residue was poured into water and extracted with dichloromethane. The organic phase was dried and concentrated. The oil that remained as a residue was purified by flash chromatography using 1:1 ethyl acetate/cyclohexane as the eluent. 29.9 g of an oil were obtained that was dissolved for crystallization in methyl-tert-butyl ether. The crystals that settled out were drawn off and dried. 25.2 g of 2-[4-(methylsulfonyl)-phenyl]-ethyl-methylsulfate were obtained.

B) 33% ethanolic methylamine solution was added in laboratory autoclaves to a solution of 14 g of the product obtained above in 27 ml absolute ethanol. Then the reaction mixture was heated twice for 8 hours to a solution temperature of 85° C. The reaction mixture was concentrated for workup and the oil obtained was purified by flash chromatography using dichloromethane/methanol/concentrated aqueous ammonia solution, ratio 35:15:2, as the eluent. The purified product was dissolved in isopropanol for crystallization. The precipitated crystals were drawn off and dried. 9.8 g of N-[2-(4-(methylsulfonylamino)-phenyl)-ethyl]-N-methylamine were obtained.

C) 3.5 g of the product obtained above were reacted with 3.5 g of 3-(5-phenyl-1,2,4-thiadiazole-3-yloxy)-propyl chloride [for preparation, see Example 54B)]using the method described in Example 54C). The oily crude title compound thus obtained was purified by flash chromatography using 10:3 ethyl acetate/methanol as the eluent. 3 g of the title compound were obtained.

In order to form a salt, the oily title compound obtained was dissolved in 200 ml of isopropanol and hydrochloric acid gas was added to the solution with ice cooling. The crystal formed was drawn off and dried. 1.15 g of 3-{3-[N-(2-(4-(methylsulfonylamino)-phenyl)-ethyl)-N-methylamino]-propyloxy}-5-phenyl-1,2,4-thiadiazole hydrochloride was obtained as a colorless solid with a melting point of 186° C.

EXAMPLE 60

3-{3-[N-(2-(3,5-Dimethoxyphenyl)-ethyl)-N-methylamino]-propyloxy}-5-phenyl-1,2,4-thiadiazole.

A) 22 g of 3,5-dimethoxybenzyl alcohol were reacted with 50 ml of phosphorus tribromide with ice cooling and the reaction mixture was heated for 30 minutes at 80° C. For workup, the reaction mixture was poured into ice water and extracted with methyl-tert-butyl ether. The organic phases were combined, dried, and concentrated. 23 g of 3,5-dimethoxybenzyl bromide were obtained as an oil.

B) 23 g of the product obtained above were reacted with 100 ml of triethylene glycol and 10 g of potassium cyanide. The reaction mixture was heated for 1 hour at 140° C. Then the reaction mixture was cooled and poured into water for workup, and extracted with ethyl acetate; the organic phase was dried and concentrated. The oil obtained was purified by flash chromatography using 2:1 ethyl acetate/cyclohexane as the eluent. 18 g of crude 3,5-dimethoxybenzyl cyanide were obtained as an oil.

C) 18 g of the product obtained above were dissolved in 100 ml of ethanol. 100 ml of 20% aqueous sodium hydroxide solution were added to the solution. The reaction mixture was refluxed for 3 hours. For workup, the reaction mixture was then cooled and concentrated. The residue was made acid by adding 20% aqueous hydrochloric acid solution and extracted with dichloromethane. The organic phase was concentrated to dryness. 15 g of 3,5-dimethoxyphenylacetic acid were obtained as a colorless solid.

D) 15 g of the product obtained above were dissolved in 150 ml of dichloromethane and the solution was reacted with a catalytic quantity of dimethylformamide. Then 6.7 ml of oxalyl chloride were added dropwise with ice cooling. The reaction mixture was boiled for 2 hours with reflux and then concentrated. The remaining residue was added to 100 ml of ethyl acetate and added dropwise to a mixture of 450 ml of ethyl acetate and 100 ml of a 40% aqueous methylamine solution. The reaction mixture was stirred for 2 hours at room temperature and then concentrated. Water, ethyl acetate, and a few drops of methanol were added in succession to the remaining residue and the reaction mixture was stirred at room temperature. Then the organic phase was separated, dried, and concentrated. The residue was recrystallized from methyl-tert-butyl ether. 14 g of N-methyl-3,5-dimethoxyphenylacetic acid amide were obtained as a colorless solid.

E) 14 g of the product obtained above were dissolved in 200 ml of tetrahydrofuran. 12 g of sodium borohydride were added to the solution and then 19 ml of glacial acetic acid were added slowly dropwise. The reaction mixture was boiled for 3 hours with reflux and then cooled to room temperature. For workup, the reaction mixture was poured into water and extracted three times with ethyl acetate, containing a few drops of methanol. The ethyl acetate extract was concentrated and the residue rendered alkaline to pH 1 by adding 20% aqueous hydrochloric acid solution. Then it was stirred for 30 minutes and the mixture made alkaline by adding sodium carbonate. Then it was extracted three times with dichloromethane, and the organic phases were combined, dried, then concentrated. The remaining oil was purified by flash chromatography using ethyl acetate/methanol/concentrated aqueous ammonia solution, ratio 15:3:0.1, as the eluent. 4.3 g of N-[2-(3,5-dimethoxyphenyl)-ethyl]-N-methylamine was obtained as a yellow oil.

F) 2.5 g of the product obtained above were reacted with 3.3 g of 3-(5-phenyl-1,2,4-thiadiazole-3-yloxy)-propyl chloride [for preparation, see Example 54B)] using the method described in Example 54C). The crude oily title compound obtained was purified by flash chromatography using ethyl acetate/methanol/concentrated aqueous ammonia solution, ratio 45:5:0.1, as the eluent. 4 g of the title compound were obtained as an oil.

In order to form a salt, the oily title compound was dissolved in isopropanol and a sufficient quantity of hydrochloric acid gas was added to the solution. Then the solution was concentrated to dryness and the oil obtained was stirred with diethylether and a small amount of isopropanol. The resultant crystals were drawn off and dried. 2 g of 3-{3-[N-(2-(3,5-dimethoxyphenyl)-ethyl)-N-methylamino]-propyloxy}-5-phenyl-1,2,4-thiadiazole hydrochloride were obtained as a colorless crystal with a melting point of 129° C.

EXAMPLE 61

3-{3-[N-(2-(4-Nitrophenyl)-ethyl)-N-methylamino]-propyloxy}-5-phenyl-1,2,4-thiadiazole.

A) 25 g of 2-(4-nitrophenyl)-ethylamine hydrochloride were suspended in 500 ml of dichloromethane and reacted with 33 ml of triethylamine. 52 g of trifluoroacetic acid anhydride were added slowly dropwise to the reaction mixture at 0° C. After addition was complete, the reaction mixture was stirred for 2 hours at room temperature and then extracted by shaking twice, each time with 200 ml of 5% aqueous hydrochloric acid solution and twice with saturated aqueous sodium hydrogen carbonate solution. Then the dichloromethane phase was dried with sodium sulfate and concentrated. The residue was added to 500 ml tetrahydrofuran and reacted with 44 ml of methyl iodide. Then 10 g of sodium hydride were added batchwise and the reaction mixture was stirred for 2 hours at room temperature. After the reaction was complete, the reaction mixture was filtered and concentrated over silica gel. The residue obtained was purified by flash chromatography using 2:1 methyl-tert-butyl ether/cyclohexane as the eluent. The oil obtained was dissolved in 300 ml of methanol. 50 ml of a 20% aqueous sodium hydroxide solution were added to the solution and the mixture was stirred for 2 hours at room temperature. Then the main quantity of methanol was distilled off and 100 ml of water were added. The solution was shaken twice with 240 ml of dichloromethane each time. The organic phases were combined, dried, and concentrated. The remaining oily reaction product was purified by flash chromatography using dichloromethane/methanol/concentrated aqueous ammonia solution as the eluent. 8.9 g of N-[2-(4-nitrophenyl)-ethyl]-N-methylamine were obtained as an oil.

B) 3.5 g of the product obtained above were reacted with 3.5 g of 3-(5-phenyl-1,2,4-thiadiazole-3-yloxy)-propyl chloride [for preparation, see Example 54B)] using the method described in Example 54C). The crude oily title compound obtained was purified by flash chromatography, initially using 1:2 ethyl acetate/cyclohexane and then using 25:1 ethyl acetate/methanol as the eluent. 5 g of the title compound were obtained as an oil.

In order to form a salt, the oily title compound was dissolved in isopropanol and an ethereal hydrochloric acid solution was added dropwise to the solution. The crystal that settled out was drawn off and dried. 3.11 g of 3-{3-[N-(2-(4-nitrophenyl)-ethyl)-N-methylamino]-propyloxy}-5-phenyl-1,2,4-thiadiazole hydrochloride were obtained.

EXAMPLE 62

3-{3-[N-(2-(4-Aminophenyl)-ethyl-N-methylamino]-propyloxy}-5-phenyl-1,2,4-thiadiazole.

2.1 g of 3-{3-[N-(2-(4-nitrophenyl)-ethyl-N-methylamino]-propyloxy}-5-phenyl-1,2,4-thiadiazole for preparation, see Example 8)), were dissolved in a mixture of 75 ml ethanol and 75 ml methanol and reacted with a catalytic quantity of Raney nickel. The reaction mixture was then hydrogenated for 2.5 hours at room temperature with hydrogen at a hydrogen pressure of 5 bars. The catalyst was filtered off and the filtrate concentrated to dryness. The oily crude title compound obtained was purified by medium-pressure chromatography over fine-grained silica gel (Lichroprep Si 60®) using 95:5 ethyl acetate/methanol as the eluent. 1.1 g of the title compound were obtained as an oil.

In order to form a salt, the oily title compound was dissolved in ethanol and ethereal hydrochloric acid solution was added to the solution. The crystals that settled out were drawn off and dried. 0.48 g of 3-{3-[N-(2-(4-aminophenyl)-ethyl)-N-methylamino]-propyloxy}-5-phenyl-1,2,4-thiadiazole hydrochloride were obtained as a colorless solid with a melting point of 183° to 186° C.

EXAMPLE 63

3-{3-[N-(2-(4-Acetaminophenyl)-ethyl)-N-methylamino]-propyloxy}-5-phenyl-1,2,4-thiadiazole.

300 mg of 3-{3-[N-(2-(4-aminophenyl)-ethyl)-N-methylamino]-propyloxy}-5-phenyl-1,2,4-thiadiazole (for preparation, see Example 62) were dissolved in 4 ml pyridine. 1 ml of acetic acid anhydride was added to the solution and the reaction mixture was stirred for 2 hours at room temperature. For workup, it was poured over ice and the mixture made alkaline by adding sodium carbonate solution. Then extraction was performed with ethyl acetate, the organic phase was separated, and concentrated to dryness. The crude oily title compound obtained was purified by medium-pressure chromatography over fine-grained silica gel (Lichroprep Si 60®) using 95:5 ethyl acetate/methanol as the eluent. 0.12 g of the title compound were obtained as an oil.

In order to form a salt, the oily title compound was dissolved in isopropanol and the solution was rendered alkaline to pH 1 by adding ethereal hydrochloric acid solution. The crystals that settled out were drawn off and dried. 150 mg of 3-{3-[N-(2-(4-acetaminophenyl)-ethyl)-N-methylamino]-propyloxy}-5-phenyl-1,2,4-thiadiazole hydrochloride were obtained with a melting point of 211° to 213° C.

EXAMPLE 64

3-{3-[N-(2-(3,4-Dimethoxyphenyl)-ethyl)-N-methylamino]-propyloxy}-4-methyl-5-phenylisoxazole.

A) 28.2 g of 2-benzoylpropionic acid ethyl ester were added to a solution of 5.2 g sodium hydroxide in a mixture of 5 ml water and 100 ml methanol at 70° C., dropwise while stirring. Then a filtered solution, cooled to −70° C., of 10.3 g sodium hydroxide and 17.1 g hydroxylamine hydrochloride in a mixture of 10 ml water and 100 ml methanol were added dropwise to the solution. Then the cooling agent was removed and the solution was stirred for another 2 hours whereupon the temperature rose to approximately 10° C. Then 9 ml of acetone were added to the reaction mixture and the reaction mixture was added at a temperature of 80° C. to 90 ml of concentrated hydrochloric acid solution. The mixture was stirred for another 30 minutes at 80° C. and then concentrated to half its original volume and stirred for several hours more at 5° C. The crystals that settled out were filtered off, added to dichloromethane, and reacted with dilute aqueous hydrochloric acid solution. The organic phase was separated, dried with magnesium sulfate, and concentrated. 18 g of crystalline 4-methyl-5-phenylisoxazole-3-ole were obtained.

B) 5.2 g of the product obtained above were dissolved in 100 ml of dimethylformamide. The solution was reacted with 4.15 g of finely powdered anhydrous potassium carbonate and the reaction mixture was then heated for 1 hour at 100° C. in a nitrogen atmosphere. Then, at 60° C., a solution of 8.4 g of 3-[N-(2-(3,4-dimethoxyphenyl)-ethyl)-N-methylamino]-propyl chloride [for preparation, see Example 58 D)] was added dropwise in approximately 50 ml dimethylformamide. The reaction mixture was stirred for 5 hours at 100° C. Then the salts that were formed were filtered off and the filtrate was concentrated to dryness and the residue dissolved in methyl-tert-butyl ether. The solution was then washed with aqueous sodium carbonate solution, dried with magnesium sulfate, and concentrated to dryness. The crude oily title compound that remained as a residue was purified by flash chromatography using a mixture of diethyl ether and hexane in a ratio of 1:1, to which 5% triethylamine and 1 to 5% methanol were added, as the eluent. 8.8 g of the title compound were obtained as an oil.

In order to form a salt, the oily title compound obtained above were dissolved in ethanol and an ethanolic oxalic acid solution was added dropwise to this solution. The crystal that formed was separated. 9.9 g of 3-{3-[N-(2-(3,4-dimethoxyphenyl)-ethyl)-N-methylamino]-propyloxy}-4-methyl-5-phenyl-isoxazole hydrogen oxalate were obtained with a melting point of 183° C.

EXAMPLE 65

3-{3-[N-(2-(3,4-Dimethoxyphenyl)-ethyl)-N-methylamino]-propyloxy}-5-(3-methoxyphenyl)-1,2,4-thiadiazole.

A) 17 g of 3-methoxybenzoyl chloride were dissolved in 200 ml acetone. 15.5 g of ammonium acetate were added to the solution and the reaction mixture was stirred for several hours at room temperature. Then it was dissolved in dichloromethane. The dichloromethane phase was dried by adding sodium carbonate and concentrated. 7.5 g of 3-methoxybenzamide were obtained as a colorless solid.

B) 15 g of 3-methoxybenzamide [preparation similar to Example 65A)] were dissolved in 80 ml toluene. 20.4 g of Lawesson's reagent (=2,4-bis(methoxyphenyl)-1,3-dithia-2,4-diphosphetane-2,4-disulfide) were added to the solution. The reaction mixture was then heated for 3 hours at 100° C. under a nitrogen atmosphere. Then the reaction mixture was concentrated for workup and the oily residue was purified by flash chromatography using dichloromethane as the eluent. 2.7 g of 3-methoxyphenyl-thiobenzamide were obtained as a yellow solid.

C) 7.3 g of 3-methoxyphenylthiobenzamide [preparation similar to Example 65B)] were dissolved in 50 ml acetone and cooled to −20° C. in a nitrogen atmosphere. A solution of 4 ml oxalyl chloride in 40 ml acetone were added slowly dropwise to this solution. Then it was stirred for 1 hour at 20° C. The crystals that settled out were drawn off and the mother liquor concentrated to approximately one-third of the original volume. A further crystal fraction was obtained. In all, 5 g of 2-(3-methoxyphenyl)-1,3-thiazole-4,5-dione were obtained as a yellow solid.

D) 5 g of the product obtained above were dissolved in 60 ml xylene. Then 5.3 g of azidotrimethylsilane were added slowly dropwise to the solution, after which the reaction mixture was heated for 4 hours at 120° C. Then the reaction mixture was cooled by allowing it to stand at room temperature whereupon crystallization occurred. The crystals that settled out were drawn off and dried. The mother liquor was reduced to one-third of the original volume, with an additional crystal fraction being obtained. In all, 2.7 g of 5-(3-methoxyphenyl)-1,2,4-thiadiazole-3-ole were obtained as a yellow solid.

E) 2.7 g of the product obtained above were reacted with 1.3 ml of 1-bromo-3-chloropropane similarly to Example 54B). The oil obtained was purified by flash chromatography using 4:1 petroleum ether/methyl-tert-butyl ether as the eluent. 2 g of crude 3-[5-(3-methoxyphenyl)-1,2,4-thiadiazole-3-oxy]-propyl chloride were obtained as an oil.

F) 2.7 g of the product obtained above were reacted with 1.9 g of N-methylhomoveratrylamine using the method described in Example 54C). The crude oily title compound obtained was purified by flash chromatography using 9:1 ethyl acetate/methanol as the eluent. 2.9 g of the title compound were obtained as an oil.

In order to form a salt, the oily title compound was dissolved in isopropanol and a sufficient quantity of gaseous hydrogen chloride was added to the solution. The crystals that settled out were drawn off and dried. 2.3 g of 3-{3-[N-(2-(3,4-dimethoxyphenyl)-ethyl)-N-methylamino]-propyloxy}-5-(3-methoxyphenyl)-1,2,4-thiadiazole hydrochloride were obtained as a colorless solid with a melting point of 175° C.

EXAMPLE 66

3-{3-[N-(2-(3,4-dimethoxyphenyl)-ethyl)-N-methylamino]-propyloxy}-5-(3-hydroxyphenyl)-1,2,4-thiadiazole.

A) 2 g of 3-[5-(3-methoxyphenyl)-1,2,4-thiadiazole-3-oxy]-propyl chloride [for preparation, see Example 65E)] were dissolved in 100 ml dichloromethane. A solution of 20 ml borotribromide in dichloromethane was added to the solution and the reaction mixture was stirred for 8 hours at room temperature under a nitrogen atmosphere. Then the reaction mixture was poured into water for workup and made alkaline by adding sodium carbonate. Then extraction was performed with dichloromethane and the organic phase was dried and concentrated. 1.9 g of crude 3-[5-(3-hydroxyphenyl)-1,2,4-thiadiazole-3-yloxy]-propyl chloride was obtained as a yellow oil.

B) 1.9 g of the product obtained above were reacted with 1.9 g of N-methylhomoveratrylamine according to the method described in Example 54C). The oily title compound obtained was purified by flash chromatography on silica gel using 9:1 dichloromethane/methanol as the eluent. 2.9 g of the title compound were obtained as an oil.

In order to form a salt, the oily title compound obtained was dissolved in ethanol and a sufficient quantity of gaseous hydrogen chloride was added to the solution. The crystals that settled out were drawn off and dried. 2.3 g of 3-{3-[N-(2-(3,4-dimethoxyphenyl)-ethyl)-N-methylamino]-propyloxy}-5-(3-hydroxyphenyl)-1,2,4-thiadiazole hydrochloride were obtained as a colorless solid with a melting point of 152° C.

EXAMPLE 67

3-{3-[N-(2-(3,4-Dimethoxyphenyl)-ethyl)-N-methylamino]-propyloxy}-5-(4-nitrophenyl)-1,2-4-oxadiazole.

A) 48 ml of oxalyl chloride were added batchwise to a solution of 50 g of 4-nitrobenzamide in 1.2 l of 1,2-dichloroethane and the reaction mixture was boiled for 17 hours with reflux. For workup, the reaction mixture was concentrated and the remaining residue distilled under a high vacuum. 56 g of 4-nitrobenzoylisocyanate were obtained as colorless crystals.

B) 56 g of the product obtained above were reacted with 67 g of azidotrimethylsilane and the reaction mixture was refluxed for 7 hours. Then the reaction mixture was processed by the method described in Example 55A). 49.8 g of crude 5-(4-nitrophenyl)-1,2,4-oxadiazole-3-ole were obtained.

C) 15 g of the product obtained above were dissolved in 300 ml of dimethylformamide and reacted with 9.7 g of potassium-tert-butylate and 7.8 ml of 1-bromo-3-chloropropane similarly to the method described in Example 55B). The crystalline crude product obtained was stirred with methanol, the crystal formed was drawn off and dried. 10.2 g of 3-[5-(4-nitrophenyl)-1,2,4-oxadiazole-3-yloxy]-propyl chloride were obtained as a colorless crystal.

D) 10.2 g of the product obtained above were reacted with 7 g of N-methylhomoveratrylamine and 5 ml of triethylamine and the reaction mixture was heated in an oil bath for 20 minutes to an oil bath temperature of 140° C. For workup, the reaction mixture was cooled, poured into ice water, and shaken with ethyl acetate. The combined organic phases were concentrated and the crude title compound that remained as a residue was purified by medium-pressure chromatography on fine-grained silica gel using 9:1 ethyl acetate/methanol as the eluent. 6.8 g of the title compound were obtained as a light yellow oil. Thin layer chromatography on silica gel: Rf value=05 (eluent: 1:9 methanol/ethyl acetate).

EXAMPLE 68

3-{3-[N-(2-(3,4-Dimethoxyphenyl)-ethyl)-N-methylamino]-propyloxy}-5-(4-aminophenyl)-1,2,4-oxadiazole.

5 g of 3-{3-[N-(2-(3,4-dimethoxyphenyl)-ethyl)-N-methylamino]-propyloxy}-5-(4-nitrophenyl)-1,2,4-oxadiazole (for preparation, see Example 67) were dissolved in 500 ml ethanol. 4 ml of hydrazinium hydroxide and a catalytic quantity of Raney nickel were added to the solution and the reaction mixture was heated at 50° C. for 30 minutes. The catalyst was then filtered off and the filtrate was concentrated to dryness. The remaining residue was reacted with 10% aqueous sodium carbonate solution and shaken with ethyl acetate. The organic phase was dried with sodium sulfate, filtered, and concentrated. The crude oily title compound that remained as a residue was purified by medium-pressure chromatography over silica gel (Lichroprep Si 60®) using 99:1 ethyl acetate/methanol as the eluent. 1.1 g of the title compound were obtained as an oil.

In order to form a salt, 270 mg of the oily title compound and 246 mg of N-acetyl-L-glutaminic acid were dissolved in a small amount of methanol. The solution was filtered and then concentrated to dryness. 240 mg of 3-{3-[N-(2-(3,4-dimethoxyphenyl)-ethyl)-N-methylamino]-propyloxy}-5-(4-aminophenyl)-1,2,4-oxadiazole-N-acetyl-L-glutamate were obtained with a melting point of 107° to 110° C.

EXAMPLE 69

3-{3-[2-(3,4-Dimethoxyphenyl)-ethylamino]-propyloxy}-5-phenyl-1,2,4-oxadiazole.

A) 17.5 g of benzoylisocyanate were reacted with 27 ml of azidotrimethylsilane according to the method described in Example 55A). 21 g of 5-phenyl-1,2,4-oxadiazole-3-ole were obtained as a colorless solid.

B) 10.7 g of the product obtained above were reacted in 300 ml dimethylformamide with 2.4 g sodium hydride and 10.9 g of 3-bromo-1-chloropropane according to the method described in Example 55B). For workup, the reaction mixture was then concentrated to dryness, the remaining residue was added to methyl-tert-butyl ether and shaken with water. The combined organic phases were dried with sodium sulfate, filtered, and concentrated. The remaining residue was dissolved in diethyl ether and refined under medium-pressure chromatography on fine-grained silica gel using 9:1 cyclohexane/ethyl acetate as the eluent. 6.7 g of 3-(5-phenyl-1,2,4-thiadiazole-3-yloxy)-propyl chloride as a colorless crystal were obtained.

C) 6.7 g of the product obtained above were reacted with 4.75 g of 2-(3,4-dimethoxyphenyl)-ethylamine using the method described in Example 55C). For workup, the reaction mixture was then concentrated to dryness and the residue dissolved in ethyl acetate. A sufficient quantity of water was added to this solution for a clear phase separation to occur. The mixture was shaken and the ethyl acetate phase was discarded. The remaining aqueous phase was acidified with citric acid and extracted with ethyl acetate. This ethyl acetate phase was likewise discarded and the remaining aqueous phase was made alkaline by adding sodium carbonate and then extracted twice with dichloromethane. The combined dichloromethane extracts were dried with sodium sulfate, filtered, and concentrated. The oily crude title compound obtained was purified using medium-pressure chromatography on fine-grained silica gel using ethyl acetate/methanol/concentrated aqueous ammonia solution, ratio 9:1:0.1, as the eluent. 3.3 g of the title compound were obtained as an oil.

In order to form a salt, 1.1 g of the above title compound were dissolved in isopropanol and reacted with ethereal hydrochloric acid solution until it became cloudy. The crystal that settled out was drawn off, rinsed initially with 1:1 isopropanol/diethylether and then with isopropanol, and dried. 1.2 g of 3-{3-[2-(3,4-dimethoxyphenyl)-ethylamino]-propyloxy}-5-phenyl-1,2,4-oxadiazole hydrochloride were obtained as a colorless crystal with a melting point of 158°–160° C.

EXAMPLE 70

3-{3-[N-(2-(3,4-Dimethoxyphenyl)-ethyl)-N-ethylamino]-propyloxy}-5-phenyl-1,2,4-oxadiazole.

2 g of 3-{3-[2-(3,4-dimethoxyphenyl)-ethylamino]-propyloxy}-5-phenyl-1,2,4-oxadiazole (for preparation, see Example 69) were dissolved in 20 ml dimethylformamide. 0.9 ml of diethylamine and 0.6 g ethyl bromide were added to the solution and the reaction mixture was heated at 50° C. for 3.5 hours. For workup, the reaction mixture was then concentrated to dryness and the residue dissolved in dichloromethane. A sufficient quantity of water was added to the solution for a clear phase separation to occur. The mixture was shaken and the organic phase separated out, dried with sodium sulfate, filtered, and concentrated. The crude oily title compound obtained was refined by medium-pressure chromatography on fine-grained silica gel using ethyl acetate/methanol/concentrated aqueous ammonia solution, ratio 9:1:0.05, as the eluent. 1.3 g of the title compound were obtained as a yellow oil.

In order to form a salt, the oily title compound was dissolved in isopropanol and the solution was reacted with an ethereal hydrochloric acid solution. The crystal that settled out was drawn off, washed with diethyl ether, and dried. 0.65 g of 3-{3-[N-(2-(3,4-dimethoxyphenyl)-ethyl)-N-ethylamino]-propyloxy}-5-phenyl-1,2,4-oxadiazole hydrochloride were obtained as a colorless crystal with a melting point of 137° to 139° C.

EXAMPLE 71

3-{4-[N-(2-(3,4-Dimethoxyphenyl)-ethyl-N-methylamino]-butyloxy}-5-phenyl-1,2,4-oxadiazole.

A) 10 g of 5-phenyl-1,2,4-oxadiazole-3-ole [for preparation, see Example 55A)] were dissolved in 150 ml of dimethylformamide. 3 g of sodium hydride were added batchwise to the solution. The reaction mixture was heated at 80° C. for 90 minutes. Then 17.22 ml of 4-chlorobutyric acid ethyl ester were added dropwise and the reaction mixture was then heated first for 30 minutes at 90° C. and then for another 45 minutes at 100° C. For workup, the dimethylformamide was then distilled off and the residue poured into ice water and extracted with ethyl acetate. The organic phase was separated, dried, and concentrated. The oil obtained was purified by chromatography over fine-grained silica gel at slightly elevated pressure (flash chromatography) using 4:1 cyclohexane/ethyl acetate as the eluent. 11.29 g of 4-(5-phenyl-1,2,4-oxadiazole-3-yloxy)-butyric butyric acid ethyl ester were obtained as an oil.

B) 11.29 g of the product obtained above were reacted with 14.32 g sodium hydroxide and 20.4 ml ethanol. The reaction mixture was heated for 30 minutes at 90° C. For workup, the reaction mixture was concentrated, then the residue dissolved in a small amount of water. Then the solution was adjusted to pH 1 by adding dilute aqueous hydrochloric acid solution. The crystals that settled out were drawn off, washed with a small amount of water, and dried. 4.04 g of 4-(5-phenyl-1,2,4-oxadiazole-3-yloxy)-butyric acid were obtained as a colorless solid.

C) Initially, 1.85 ml of triethylamine and then 2.77 g of the product produced previously under Example 71B) were added to a solution of 3.42 g of 2-chloro-N-methylpyridinium iodide in 123 ml dichloromethane. The reaction mixture was stirred for 15 minutes at room temperature. Then 2.19 g of N-methylhomoveratrylamine were added and the reaction solution was stirred once again for 30 minutes at room temperature. For workup, the reaction mixture was concentrated to dryness and the residue added to water and shaken with ethyl acetate. The organic phase was separated, dried with sodium sulfate, and concentrated. The oil obtained was refined by chromatography over fine-grained silica gel at a slightly elevated pressure (flash chromatography) using ethyl acetate as the eluent. 3.96 g of 4-(5-phenyl-1,2,4-oxadiazole-3-yloxy)-butyric acid N-[2-(3,4-dimethoxyphenyl)-ethyl]-N-methylamide were obtained as a colorless solid.

D) 3.96 g of the product obtained above were dissolved in 150 ml of tetrahydrofuran. 5 ml of diisobutylaluminum hydride were added to the solution. The reaction mixture was stirred for 30 minutes at room temperature. Then 5 ml of diisobutylaluminum hydride were added dropwise again, twice. Next, the reaction mixture was slowly heated at 50° C. and stirred for 1 hour at this temperature. Then 100 ml of concentrated aqueous citric acid solution were added and the solution was stirred for another 30 minutes at 50° C. Then the tetrahydrofuran was distilled off and the remaining aqueous solution was shaken with ethyl acetate. The organic phase was discarded and the aqueous phase was then neutralized by adding aqueous sodium hydroxide solution and shaken with ethyl acetate. This ethyl acetate phase was dried and concentrated. The crude title compound that remained as a residue was purified by chromatography over fine-grained silica gel at a slightly elevated pressure (flash chromatography) using 1:1 ethyl acetate/methanol as the eluent. 1.9 g of the title compound were obtained.

In order to form a salt, 1.9 g of the title compound were dissolved in ethanol and the solution was reacted with ethereal hydrochloric acid solution. Then it was concentrated to dryness and the residue added to isopropanol. The crystals that settled out were drawn off and dried. 0.8 g of 3-{4-[N-(2-(3,4-dimethoxyphenyl)-ethyl)-N-methylamino]-butyloxy}-5-phenyl-1,2,4-oxadiazole hydrochloride were obtained as a colorless solid with a melting point of 148.5° to 150.5° C.

EXAMPLE 72

3-{3-[N-(2-(4-hydroxy-3-methoxyphenyl)-ethyl)-N-methylamino]-propyloxy}-5-phenyl-1,2,4-thiadiazole.

A) 5 g of 4-hydroxy-3-methoxyphenyl ethyl acetate were dissolved in 25 ml dichloromethane. 15.3 g of N-(ethyl)-diisopropylamine and 12.65 ml of 2-(trimethylsilyl)-ethoxymethyl chloride were added to the solution. The reaction mixture was stirred for 1.5 hours at room temperature. For workup, the reaction mixture was then shaken with water. The dichloromethane phase was separated and concentrated to dryness. The oil obtained was dissolved in methyl-tert-butyl ether and shaken with water once more. The organic phase was dried with sodium sulfate, filtered, and concentrated. 7.8 g of 4-[2-(trimethylsilyl)-ethoxymethyl]-3-methoxyphenyl ethyl acetate were obtained as an oil.

B) 7.8 g of the product obtained above were dissolved in 100 ml ethanol. 11.2 ml of 40% aqueous sodium hydroxide solution were added to the solution and the reaction mixture was stirred for 1 hour at 42° C. For workup, the reaction mixture was concentrated to dryness and the residue dissolved in ethyl acetate. A sufficient quantity of water was added to this solution for a clear phase separation to occur. The mixture was shaken and the ethyl acetate phase was discarded. The remaining aqueous phase was rendered alkaline to pH 4 by adding citric acid and extracted twice with dichloromethane. The combined dichloromethane extracts were dried with sodium sulfate, filtered, and concentrated. 6.7 g of 4-[2-(trimethylsilyl)-ethoxymethoxy]-3-methoxyphenyl acetic acid were obtained.

C) 6.6 g of the product obtained above were dissolved in 105 ml of absolute tetrahydrofuran. 3.8 g of 1,1'-carbonyldimidazole were added to the solution and the reaction mixture was stirred for 1 hour at room temperature. Then 5.7 g of methylamine hydrochloride and 11.7 ml of triethylamine were added and the reaction mixture was stirred for another 3.5 hours at room temperature. For workup, the reaction mixture was concentrated to dryness and the residue dissolved in methyl-tert-butyl ether. The solution was initially shaken with water and then in succession with aqueous sodium carbonate solution, dilute aqueous citric acid solution, and water. Then the organic phase was dried with sodium sulfate, filtered, and concentrated. 5.9 g of 4-[2-(trimethylsilyl)-ethoxymethoxy]-3-methoxyphenyl acetic acid N-methylamide were obtained as a colorless solid.

D) 5.8 g of the product obtained above were dissolved in 200 ml of dried dioxane. 3.4 g of sodium borohydride were added to the solution batchwise under a nitrogen atmosphere and subjected to ice cooling. 5.1 ml of glacial acetic acid were carefully added dropwise to the resultant suspension and the reaction mixture was stirred for 2.5 hours and refluxed. Then the reaction mixture was concentrated to dryness, the remaining residue dissolved in 50 ml methanol, and 1 ml of 10% aqueous hydrochloric acid solution were added. The mixture was stirred for 15 minutes at room temperature and then concentrated to dryness. The residue was dissolved in dilute aqueous citric acid solution and extracted with ethyl acetate. The ethyl acetate phase was dried with sodium sulfate, filtered, and concentrated. The remaining oil was dissolved in 50 ml methanol. 2 ml of a 10% aqueous hydrochloric acid solution were added to the solution and the reaction mixture was boiled for 5 hours with reflux. Then an acid/base separation of the reaction mixture was performed, the aqueous phase was separated and concentrated to dryness. The remaining residue was extracted with a dilute aqueous citric acid solution. This extract was rendered alkaline by adding aqueous sodium hydroxide solution and extracted with dichloromethane. The dichloromethane phase was dried with sodium sulfate, filtered, and concentrated. 0.95 g of N-{2-[4-(2-(trimethylsilyl)-ethoxymethoxy)-3-methoxyphenyl]-ethyl}-N-methylamine were obtained as an oil.

E) 0.85 g of the product obtained above were reacted with 0.7 g of 3-(5-phenyl-1,2,4-thiadiazole-3-yloxy)-propyl chloride [for preparation, see Example 54B)] and the reaction mixture was stirred for 10.5 hours at 65° C. Then the reaction mixture was dissolved in dichloromethane and the solution shaken with water. The dichloromethane phase was separated, dried, and concentrated. The crude product obtained was purified by medium-pressure chromatography on fine-grained silica gel (Lichroprep Si 60®) using 9:1 ethyl acetate/methanol as the eluent. 0.5 g of 3-{3-[N-[2-(4-(2-trimethylsilyl)-ethoxymethoxy)-3-methoxyphenyl)-ethyl]-N-methylamino]-propyloxy}-5-phenyl-1,2,4-thiadiazole were obtained as a colorless oil.

F) 0.5 g of the product obtained above were reacted with 5 ml of a 1-molar solution of tetrabutylammonium fluoride in tetrahydrofuran. The reaction mixture was concentrated to dryness and the remaining residue was admixed with 0.5 g of molecular sieve which had been ground in a mortar (specification: A4, pore size 4–8 mesh) and 5 ml 1,3-dimethyltetrahydro-2-(1H)-pyrimidinone (=DMPU). The mixture was then stirred for 1 hour at room temperature. For workup, it was then diluted with water and the mixture was extracted twice with dichloromethane. The combined dichloromethane phases were dried with sodium sulfate, filtered, and concentrated. The crude title compound obtained was purified by medium-pressure chromatography on fine-grained silica gel (Lichroprep Si 60®) using 9:1 ethyl acetate/methanol as the eluent. After the eluate fractions containing the product had been concentrated, the title compound was obtained in the form of a crude yellow oil that was still slightly contaminated. This oil was then distilled in a bulb tube at 150° C. and 1 mbar pressure. 320 mg of the title compound were obtained as a yellow oil.

In order to form a salt, the oily title compound was dissolved in ethyl acetate and shaken first with water and then with citric acid. The citric acid phase was rendered alkaline to pH 9 with sodium carbonate solution and extracted twice with ethyl acetate. The extract was dried with sodium sulfate and concentrated. The residue was dissolved in methanol and reacted with a sufficient quantity of ethereal hydrochloric acid solution. For crystallization, it was cooled with ice water. The crystals that settled out were drawn off, washed with methanol/diethyl ether 1:1 and dried. 167 mg of 3-{3-[N-2-(4-hydroxy-3-methoxyphenyl)-ethyl)-N-methylamino]-propyloxy}-5-phenyl-1,2,4-thiadiazole were obtained as a colorless crystal with a melting point of 137°–138° C.

The compounds of formula XXXI listed in the following table could also be produced using the methods described in the foregoing examples. The IR bands listed in the table in $cm^{-1}$ are the characteristic bands in the IR spectra of the respective free bases (as films unless otherwise stated).

| Example No. | $R^1$ | $R^2$ | $R^3$ | n | Q | A | B | $R^4$ | Remarks mp. in °C.; IR bands in $cm^{-1}$ |
|---|---|---|---|---|---|---|---|---|---|
| 73 | $CH_3$ | H | 4-F | 2 | —$(CH_2)_3$— | N | O | phenyl | 1 HCl; mp. 148–150 |
| 74 | $CH_3$ | H | 4-F | 2 | —$(CH_2)_3$— | N | O | 4-F-phenyl | 1 HCl; mp. 149–151 |
| 75 | $CH_3$ | H | H | 2 | —$(CH_2)_3$— | N | O | phenyl | 1 HCl; mp. 128–130 |
| 76 | $CH_3$ | H | 4-F | 2 | —$(CH_2)_3$— | N | S | phenyl | 1 HCl; mp. 131 |
| 77 | $CH_3$ | H | 4-F | 2 | —$(CH_2)_3$— | CH | O | phenyl | 1 Fu; mp. 135 |
| 78 | $CH_3$ | 3,4-O—$CH_2$—O | | 2 | —$(CH_2)_3$— | N | O | phenyl | 1 HCl; mp. 162–164 |
| 79 | $CH_3$ | 3-$OCH_3$ | 4-$OCH_3$ | 2 | —$(CH_2)_3$— | N | O | 3,4-O—$CH_2$—O-Ph | 1 HCl; mp. 194–197 |
| 80 | $CH_3$ | H | 4-$NO_2$ | 2 | —$(CH_2)_3$— | N | O | phenyl | 1 HCl; mp. 171–173 |
| 81 | $CH_3$ | H | H | 2 | —$(CH_2)_3$— | CH | O | phenyl | 1 Ox; mp. 190 |
| 82 | $CH_3$ | 3-$OCH_3$ | 4-$OCH_3$ | 2 | —$(CH_2)_3$— | N | S | 4-$CH_3$-phenyl | 1 HCl; mp. 171–173 |
| 83 | $CH_3$ | H | H | 2 | —$(CH_2)_3$— | CH | O | 4-F-phenyl | 1 Ox; mp. 138 |
| 84 | $CH_3$ | 4-F | H | 2 | —$(CH_2)_3$— | CH | O | 4-F-phenyl | 1 Ta = amorph.; base = oil IR: 1624, 1524, 1510, 1455 |
| 85 | $CH_3$ | 3-$OCH_3$ | 4-$OCH_3$ | 2 | —$(CH_2)_2$— | N | O | phenyl | 1 HCl; mp. 163–165 |
| 86 | $CH_3$ | H | 4-$NHSO_2CH_3$ | 2 | —$(CH_2)_3$— | N | O | phenyl | 1 HCl; mp. 150–152 |
| 87 | $CH_3$ | 3-$OCH_3$ | 4-$OCH_3$ | 2 | —$(CH_2)_5$— | O | O | phenyl | 1 HCl; mp. 162–164 |
| 88 | $CH_3$ | 3-$OCH_3$ | 4-$OCH_3$ | 3 | —$(CH_2)_3$— | N | O | phenyl | 1 HCl; mp. 230–232 |
| 89 | $CH_3$ | H | 4-F | 2 | —$(CH_2)_3$— | N | S | 4-F-phenyl | 1 HCl; mp. 151 |
| 90 | $CH_3$ | 3-$OCH_3$ | 4-$OCH_3$ | 2 | —$(CH_2)_3$— | N | S | 4-F-phenyl | 1 HCl; mp. 163 |
| 91 | $CH_3$ | 3-$OCH_3$ | 4-$OCH_3$ | 2 | —$(CH_2)_3$— | N | S | 3-F-phenyl | 1 HCl; mp. 153 |
| 92 | $CH_3$ | 3-$OCH_3$ | 4-$OCH_3$ | 2 | —$(CH_2)_3$— | N | S | 4-$OCH_3$-phenyl | 1 HCl; mp. 170 |
| 93 | $CH_3$ | 3-$OCH_3$ | 4-$OCH_3$ | 2 | —$(CH_2)_3$— | N | S | 3-$CH_3$-phenyl | 1 HCl; mp. 116 |
| 94 | $CH_3$ | 3-$OCH_3$ | 4-$OCH_3$ | 4 | —$(CH_2)_3$— | N | O | phenyl | 1 HCl; mp. 110–111 |
| 95 | $CH_3$ | 3-$OCH_3$ | 4-$OCH_3$ | 2 | —$(CH_2)_3$— | N | S | 2-F-phenyl | 1 HCl; mp. 187 |
| 96 | $CH_3$ | 3-$OCH_3$ | 4-$OCH_3$ | 2 | —$(CH_2)_3$— | N | S | thien-2-yl | 1 HCl; mp. 173–175 |
| 97 | $CH_3$ | 3-$OCH_3$ | 4-$OCH_3$ | 2 | —$(CH_2)_3$— | N | O | thien-3-yl | 1 HCl; mp. 148–149 |
| 98 | $CH_3$ | 3-$OCH_3$ | 4-$OCH_3$ | 2 | —$(CH_2)_3$— | N | S | 3,4-di($OCH_3$)-ph | 1 HCl; mp. 167–169 |
| 99 | $CH_3$ | 3-$OCH_3$ | 4-$OCH_3$ | 2 | —$(CH_2)_3$— | N | O | 2-Cl-phenyl | 1 HCl; mp. 166–168 |
| 100 | $CH_3$ | 3-$OCH_3$ | 4-$OCH_3$ | 2 | —$(CH_2)_3$— | N | O | 2-F-phenyl | 1 HCl; mp. 170–172 |
| 101 | $CH_3$ | 3-$OCH_3$ | 4-$OCH_3$ | 2 | —$(CH_2)_3$— | N | S | 2-$CH_3$-phenyl | 1 HCl; mp. 146 |
| 102 | $CH_3$ | 3-F | 4-F | 2 | —$(CH_2)_3$— | N | S | phenyl | 1 HCl; mp. 168–170 |
| 103 | $CH_3$ | 3-$OCH_3$ | 4-$OCH_3$ | 2 | —$(CH_2)_3$— | N | S | 2-$OCH_3$-phenyl | 1 HCl; mp. 176 |
| 104 | $CH_3$ | 3-F | 4-$OCH_3$ | 2 | —$(CH_2)_3$— | N | S | phenyl | 1 HCl; mp. 158 |
| 105 | $CH_3$ | 3-$OCH_3$ | 4-$OCH_3$ | 2 | —$(CH_2)_3$— | C-Et | O | phenyl | 1 Ox = amorph.; base = oil IR: 1636, 1591, 1508 |
| 106 | H | 3-$OCH_3$ | 4-$OCH_3$ | 2 | —$(CH_2)_3$— | N | S | phenyl | 1 HCl; mp. 168 |
| 107 | $CH_3$ | 3-$OCH_3$ | 4-$OCH_3$ | 2 | —$(CH_2)_3$— | N | O | 3,4-di($OCH_3$)-ph | 1 HCl; mp. 183–185 |
| 108 | $CH_3$ | 3-$OCH_3$ | 4-$OCH_3$ | 3 | —$(CH_2)_3$— | C-Me | O | phenyl | 1 Ox = amorph.; base = oil IR: 1644, 1516, 1469, 1454 |
| 109 | n-$C_3H_7$ | 3-$OCH_3$ | 4-$OCH_3$ | 2 | —$(CH_2)_3$— | N | O | phenyl | 1 Ox; mp. 110–114 |
| 110 | $CH_3$ | 3-$OCH_3$ | 4-$OCH_3$ | 2 | —$(CH_2)_3$— | N | S | 4-Cl-phenyl | 1 HCl; mp. 186–188 |
| 111 | $CH_3$ | 3-$OCH_3$ | 4-$OCH_3$ | 2 | —$(CH_2)_3$— | N | S | 2-Cl-phenyl | 1 HCl; mp. 182 |
| 112 | $CH_3$ | 3-$OCH_3$ | 4-$OCH_3$ | 2 | —$(CH_2)_3$— | N | S | 2,3-di(Cl)-ph | 1 HCl; mp. 179 |
| 113 | $CH_3$ | 3-$OCH_3$ | 4-$OCH_3$ | 2 | —$(CH_2)_3$— | N | S | 3-Cl-phenyl | 1 HCl; mp. 179 |
| 114 | $CH_3$ | 3-$OCH_3$ | 4-$OCH_3$ | 2 | —$(CH_2)_3$— | CH | O | phenyl | 1 Ta = amorph.; base = oil IR: 1622, 1596, 1576, 1515 |
| 115 | $CH_3$ | 3-$OCH_3$ | 4-$OCH_3$ | 2 | —$(CH_2)_3$— | N | S | 2-5-di(Cl)-ph | 1 HCl; mp. 205 |
| 116 | $CH_3$ | 3-$OCH_3$ | 4-$OCH_3$ | 2 | $CH_2$—$CH(CH_3)$—$CH_2$ | N | S | phenyl | 1 HCl; mp. 142 |
| 117 | $CH_3$ | 3-$OCH_3$ | 4-$OCH_3$ | 2 | —$(CH_2)_3$— | N | O | 4-$NHCOCH_3$-ph | 1 Ag; mp. 77–80 |
| 118 | $CH_3$ | H | 4-$CH_3$ | 2 | —$(CH_2)_3$— | N | S | phenyl | 1 HCl; mp. 140 |
| 119 | $CH_3$ | 3-Cl | 4-Cl | 2 | —$(CH_2)_3$— | N | S | phenyl | 1 HCl; mp. 183 |
| 120 | $CH_3$ | 3-$OCH_3$ | 4-$OCH_3$ | 2 | —$(CH_2)_3$— | N | S | 3-$CF_3$-phenyl | 1 HCl; mp. 152 | ph = phenyl;
HCl = hydrochloride;
Fu = hydrogen fumarate;
Ox = hydrogen oxalate;
Ta = hydrogen tartrate;
Ag = acetyl glutamate;
Et = ethyl;
Me = methyl

Example I

Tablets containing 3-{3-[N-(2-(3,4-dimethoxyphenyl)-ethyl)-N-methylamino]-propyloxy}-5-(3,4-dimethoxyphenyl)-pyrazole hydrochloride.

Tablets were produced having the following composition per tablet:

| | |
|---|---|
| 3-{3-[N-(2-(3,4-dimethoxyphenyl)-ethyl)-N-methylamino]-propyloxy}-5-(3,4-dimethoxy-phenyl)-pyrazole hydrochloride | 20 mg |
| Corn starch | 60 mg |
| Lactose | 135 mg |
| Gelatine (as 10% solution) | 6 mg |

The active substance, the corn starch and the lactose were thickened with the 10% gelatine solution. The paste was comminuted, and the resulting granules were deposited on a suitable metal sheet and dried at 45° C. The dried granules were passed through a comminution machine and mixed in a mixer with the following further adjuvants:

| | |
|---|---|
| Talc | 5 mg |
| Magnesium stearate | 5 mg |
| Corn starch | 9 mg | and then pressed into 240 mg tablets.

Example II

Tablets containing 3-{3-[N-(2-(3,4-dimethoxyphenyl)-ethyl)-N-methylamino]-propyloxy)-5-phenyl-1,2,4-thiadiazole. hydrochloride.

Tablets were prepared having the following composition per tablet:

| | |
|---|---|
| 3-{3-[N-(2-(3,4-Dimethoxyphenyl)-ethyl)-N-methylamino]-propyloxy}-5-phenyl-1,2,4-thiadiazole hydrochloride | 20 mg |
| Corn starch | 60 mg |
| Lactose | 35 mg |
| Gelatin (as 10% solution) | 6 mg |

The active compound, corn starch, and lactose were thickened with the 10% gelatin solution. The paste was crushed and the resulting granulate was placed on a suitable sheet and dried at 45° C. The dried granulate was fed through a crusher and mixed in a mixer with the following additives:

| | |
|---|---|
| Talc | 5 mg |
| Magnesium stearate | 5 mg |
| Corn starch | 9 mg | and then pressed into 240 mg tablets.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A compound corresponding to the formula I:

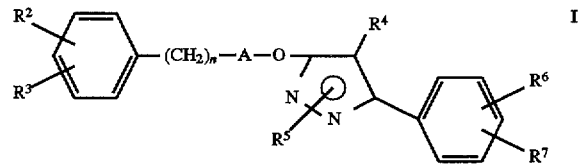

wherein n is an integer from 1 to 5,

A represents a group corresponding to the formula a

in which $R^1$ denotes hydrogen or a lower alkyl group, and

Q is bonded to the oxygen atom of Formula I and denotes a $(CH_2)_m$ group in which m denotes 2 to 6 and which may optionally be substituted in the α position to the oxygen atom by 1 or 2 lower alkyl groups;

or a group corresponding to the formula b

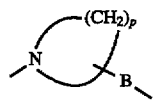

in which p denotes 5, and

B represents a $(CH_2)_r$ group in which r denotes 1 to 3 and which may optionally be substituted in the α position to the oxygen atom by 1 to 2 lower alkyl groups;

$R^2$ denotes hydrogen, halogen, lower alkyl, lower alkoxy, hydroxyl, trifluoromethyl or nitro or, $R^3$, $R^6$ and $R^7$ are other than hydroxyl, $R^2$ may be a lower alkanoyloxy group; and $R^3$ denotes hydrogen, halogen, lower alkyl, lower alkoxy, hydroxyl or, if $R^2$, $R^6$ and $R^7$ are other than hydroxyl, $R^3$ may be a lower alkanoyloxy group; or $R^2$ and $R^3$ are attached to two adjacent carbon atoms and together represent an alkylenedioxy group with 1 or 2 carbon atoms;

$R^4$ denotes hydrogen or lower alkyl;

$R^5$ is disposed in the 1 or 2 position and denotes hydrogen, lower alkyl or a phenyl-lower alkyl group;

$R^6$ denotes hydrogen, lower alkyl, lower alkoxy, hydroxyl, halogen, trifluoromethyl or nitro or, if $R^2$, $R^3$ and $R^7$ are other than hydroxyl, $R^6$ may be a lower alkanoyloxy group, and $R^7$ denotes hydrogen, lower alkyl, lower alkoxy, hydroxyl or halogen or, if a lower alkanoyloxy group, or $R^6$ and $R^7$ are attached to two adjacent carbon atoms and together form an alkylenedioxy group with 1 or 2 carbon atoms, or a physiologically acceptable acid addition salt thereof.

2. A compound according to claim 1, wherein n is 2 or 3;

A represents
  a group of formula a in which $R^1$ denotes hydrogen or lower alkyl, and Q denotes a $(CH_2)_m$ group in which m is 2 to 4, or
  a group of formula b;

$R^2$ denotes hydrogen, lower alkoxy or hydroxyl;

$R^3$ denotes hydrogen or lower alkoxy;

$R^4$ denotes hydrogen;

$R^5$ denotes hydrogen or benzyl;

$R^6$ denotes hydrogen, lower alkoxy, hydroxyl or nitro; and $R^7$ denotes hydrogen or lower alkyl.

3. A compound according to claim 2, wherein n is 2;

A represents a group of formula a in which $R^1$ denotes methyl or hydrogen, and Q represents a $(CH_2)_m$ group in which m denotes 3 or 4;

$R^2$ denotes methoxy or hydroxyl;

$R^3$ denotes methoxy;

$R^6$ denotes methoxy, hydrogen or hydroxyl; and $R^7$ denotes methoxy or hydrogen.

4. A compound according to claim 3, selected from the group consisting of 3-{3-[N-(2-(3,4-Dimethoxyphenyl)-ethyl)-N-methylamino]-propyloxy}-5-(3,4-dimethoxyphenyl)-pyrazole, 3-{3-[N-(2-(3,4-dimethoxyphenyl)-ethyl)-N-methylamino]-propyloxy}-5-(4-hydroxy-3-methoxyphenyl)-pyrazole and physiologically acceptable acid addition salts thereof.

5. A compound according to claim 2, selected from the group consisting of 3-{[N-(2-(3,4-Dimethoxyphenyl)-ethyl)-piperid-3-yl]-methoxy}-5-(3,4-dimethoxyphenyl)-pyrazole and physiologically acceptable acid addition salts thereof.

6. A pharmaceutical composition comprising an effective cardioactive amount of a compound according to claim 1, and a conventional pharmaceutical carrier or adjuvant.

* * * * *